US011458126B2

(12) United States Patent
Cao et al.

(10) Patent No.: US 11,458,126 B2
(45) Date of Patent: Oct. 4, 2022

(54) DHODH INHIBITOR FOR USE IN TREATING HEMATOLOGIC CANCERS

(71) Applicant: PTC THERAPEUTICS, INC., South Plainfield, NJ (US)

(72) Inventors: Liangxian Cao, East Brunswick, NJ (US); Marla Weetall, Morristown, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 16/635,532

(22) PCT Filed: Aug. 1, 2018

(86) PCT No.: PCT/US2018/044862
§ 371 (c)(1),
(2) Date: Jan. 30, 2020

(87) PCT Pub. No.: WO2019/028171
PCT Pub. Date: Feb. 7, 2019

(65) Prior Publication Data
US 2020/0253940 A1 Aug. 13, 2020

Related U.S. Application Data

(60) Provisional application No. 62/617,180, filed on Jan. 13, 2018, provisional application No. 62/540,051, filed on Aug. 1, 2017.

(51) Int. Cl.
*A61K 31/437* (2006.01)
*A61P 35/02* (2006.01)
*A61K 31/53* (2006.01)
*A61K 9/00* (2006.01)

(52) U.S. Cl.
CPC .......... *A61K 31/437* (2013.01); *A61K 31/53* (2013.01); *A61P 35/02* (2018.01); *A61K 9/0053* (2013.01)

(58) Field of Classification Search
CPC .................. A61K 31/437; A61P 35/02
USPC ....................................... 514/292
See application file for complete search history.

(56) References Cited

U.S. PATENT DOCUMENTS

| | | | |
|---|---|---|---|
| 3,328,412 A | 6/1967 | Atkinson et al. | |
| 5,206,377 A | 4/1993 | McAfee | |
| 5,314,908 A | 5/1994 | McAfee | |
| 5,500,431 A | 3/1996 | Audia et al. | |
| 5,760,051 A | 6/1998 | Audia et al. | |
| 5,866,587 A | 2/1999 | de Nanteuil et al. | |
| 6,090,945 A | 7/2000 | Audia et al. | |
| 6,093,723 A | 7/2000 | Miao et al. | |
| 6,720,331 B2 | 4/2004 | Yeh et al. | |
| 6,987,115 B2 | 1/2006 | Seefeld | |
| 7,022,856 B2 | 4/2006 | Orme et al. | |
| 7,122,554 B2 | 10/2006 | Sawyer et al. | |
| 7,208,582 B2 | 4/2007 | Rosen et al. | |
| 7,341,749 B2 | 3/2008 | Hall et al. | |
| 7,601,840 B2 | 10/2009 | Moon et al. | |
| 7,696,227 B2 | 4/2010 | Diamond et al. | |
| 7,767,689 B2 | 8/2010 | Moon et al. | |
| 7,855,295 B2 | 12/2010 | Wang et al. | |
| 7,872,133 B2 | 1/2011 | Ohmoto et al. | |
| 8,076,352 B2 | 12/2011 | Cao et al. | |
| 8,076,353 B2 | 12/2011 | Cao et al. | |
| 8,143,257 B2 | 3/2012 | Choi et al. | |
| 8,349,853 B2 | 1/2013 | Bamdad | |
| 8,367,694 B2 | 2/2013 | Moon et al. | |
| 8,372,860 B2 | 2/2013 | Moon et al. | |
| 8,697,662 B2 | 4/2014 | Cao et al. | |
| 8,703,726 B2 | 4/2014 | Cao et al. | |
| 8,945,069 B2 | 2/2015 | Plumptre et al. | |
| 8,946,444 B2 | 2/2015 | Lennox et al. | |
| 9,271,960 B2 | 3/2016 | Lennox et al. | |
| 9,351,964 B2 | 5/2016 | Almstead et al. | |
| 2003/0040527 A1 | 2/2003 | Yeh et al. | |

(Continued)

FOREIGN PATENT DOCUMENTS

| CN | 1980672 A | 6/2007 |
|---|---|---|
| EP | 0357122 A2 | 3/1990 |

(Continued)

OTHER PUBLICATIONS

Fiedler, W. et al., "An open-label, Phase I study of cediranib (RECENTIN) in patients with acute myeloid leukemia", Leukemia Research 34(2), pp. 196-202, 2010; abstract only (1 page).

(Continued)

*Primary Examiner* — Charan J Au It Lakh
(74) *Attorney, Agent, or Firm* — Hoffman & Baron, LLP

(57) ABSTRACT

A method of use for Cpd 1 as an inhibitor of dihydroorotate dehydrogenase (DHODH) function in treating or ameliorating a hematological cancer in a subject in need thereof comprising, administering an effective amount of Cpd 1 to the subject, having the structure:

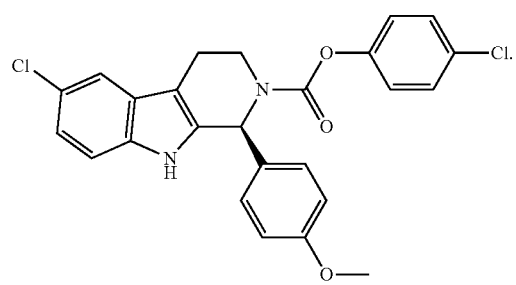

or a form or pharmaceutical composition thereof.

7 Claims, 12 Drawing Sheets

(56) References Cited

U.S. PATENT DOCUMENTS

| | | |
|---|---|---|
| 2003/0130293 A1 | 7/2003 | Bamdad |
| 2004/0053954 A1 | 3/2004 | Seefeld |
| 2004/0102438 A1 | 5/2004 | Brueckner et al. |
| 2004/0116458 A1 | 6/2004 | Sawyer et al. |
| 2004/0122035 A1 | 6/2004 | Orme et al. |
| 2005/0143371 A1 | 6/2005 | Meyers et al. |
| 2005/0215580 A1 | 9/2005 | Wang et al. |
| 2005/0272759 A1 | 12/2005 | Moon et al. |
| 2005/0276808 A1 | 12/2005 | Cedarbaum |
| 2005/0282849 A1 | 12/2005 | Moon et al. |
| 2006/0019923 A1 | 1/2006 | Davis et al. |
| 2006/0154944 A1 | 7/2006 | Ohmoto et al. |
| 2006/0241084 A1 | 10/2006 | Roifman et al. |
| 2007/0129320 A9 | 6/2007 | Davis et al. |
| 2007/0254878 A1 | 11/2007 | Cao et al. |
| 2007/0281962 A2 | 12/2007 | Moon et al. |
| 2008/0103164 A1 | 5/2008 | Gudmundsson et al. |
| 2008/0103213 A1 | 5/2008 | Kurzrock et al. |
| 2008/0261956 A1 | 10/2008 | Choi et al. |
| 2008/0293766 A1 | 11/2008 | Diamond et al. |
| 2009/0017021 A1 | 1/2009 | Davis et al. |
| 2009/0227618 A2 | 9/2009 | Moon et al. |
| 2010/0125065 A1 | 5/2010 | Moon et al. |
| 2010/0158858 A1 | 6/2010 | Cao et al. |
| 2010/0179132 A1 | 7/2010 | Moon et al. |
| 2011/0160190 A1 | 6/2011 | Moon et al. |
| 2012/0046643 A1 | 2/2012 | Plumptre et al. |
| 2012/0129841 A1 | 5/2012 | Cao et al. |
| 2012/0157400 A1 | 6/2012 | Cao et al. |
| 2012/0157401 A1 | 6/2012 | Cao et al. |
| 2012/0157402 A1 | 6/2012 | Cao et al. |
| 2012/0178707 A1 | 7/2012 | Cao et al. |
| 2012/0202763 A1 | 8/2012 | Almstead et al. |
| 2012/0202801 A1 | 8/2012 | Cao et al. |
| 2013/0171103 A1 | 7/2013 | Davis et al. |
| 2015/0141418 A1 | 5/2015 | Lennox et al. |
| 2015/0315182 A1 | 11/2015 | Lee et al. |
| 2016/0340354 A1 | 11/2016 | Davis et al. |
| 2017/0143712 A1 | 5/2017 | Lannutti et al. |
| 2019/0194188 A1 | 6/2019 | Davis et al. |

FOREIGN PATENT DOCUMENTS

| | | |
|---|---|---|
| EP | 0549916 A2 | 7/1993 |
| EP | 1637521 A1 | 3/2006 |
| EP | 2201972 A1 | 6/2010 |
| FR | 2662940 A1 | 12/1991 |
| JP | 3-287586 | 12/1991 |
| JP | 4275221 | 9/2002 |
| JP | 2004-518729 A | 6/2004 |
| JP | 2004-518730 A | 6/2004 |
| JP | 2004-532816 A | 10/2004 |
| JP | 2007-518822 A | 7/2007 |
| JP | 2007-529534 A | 10/2007 |
| JP | 2008-506683 A | 3/2008 |
| JP | 2008-508356 A | 3/2008 |
| JP | 2008-520742 A | 6/2008 |
| JP | 2008-536876 A | 9/2008 |
| JP | 2010-523682 A | 7/2010 |
| JP | 2012-513266 A | 6/2012 |
| WO | 1991/018604 | 12/1991 |
| WO | 1994/010175 | 5/1994 |
| WO | 1995/026723 | 10/1995 |
| WO | 1997/037658 | 10/1997 |
| WO | 2002/062339 A1 | 8/2002 |
| WO | 2002/064590 A2 | 8/2002 |
| WO | 2002/064591 A2 | 8/2002 |
| WO | 2003/020279 A2 | 3/2003 |
| WO | 2003/033496 A1 | 4/2003 |
| WO | 2003/099821 A1 | 12/2003 |
| WO | 2004/113300 A1 | 12/2004 |
| WO | 2004/113336 A1 | 12/2004 |
| WO | 2005/007672 A2 | 1/2005 |
| WO | 2005/009370 A2 | 2/2005 |
| WO | 2005/070930 A2 | 8/2005 |
| WO | 2005/089764 A1 | 9/2005 |
| WO | 2005/089765 A1 | 9/2005 |
| WO | 2005/115470 A2 | 12/2005 |
| WO | 2006/015035 A1 | 2/2006 |
| WO | 2006/058088 A2 | 6/2006 |
| WO | 2006/065479 A2 | 6/2006 |
| WO | 2006/065480 A2 | 6/2006 |
| WO | 2006/113703 A2 | 10/2006 |
| WO | 2006/134423 A2 | 12/2006 |
| WO | 2007/002051 A1 | 1/2007 |
| WO | 2008/127714 A1 | 10/2008 |
| WO | 2008/127715 A1 | 10/2008 |
| WO | 2008127715 A1 | 10/2008 |
| WO | 2010/072662 A1 | 7/2010 |
| WO | 2010/138758 A1 | 12/2010 |
| WO | 2011/150162 A1 | 12/2011 |
| WO | 2014/081906 A2 | 5/2014 |
| WO | 2017/073743 A1 | 4/2017 |
| WO | 2017/073743 A1 | 5/2017 |
| WO | 2019/018185 A1 | 1/2019 |
| WO | 2019/028171 A1 | 2/2019 |
| WO | 2020/028778 A1 | 2/2020 |

OTHER PUBLICATIONS

International Search Report issued in PCT/US2018/044862, dated Sep. 25, 2018 (2 pages).
Written Opinion of the International Searching Authority issued in PCT/US2018/044862, dated Sep. 10, 2018 (7 pages).
The Eyetech Study Group, 2002, "Preclinical and phase 1a clinical evaluation of an anti-VEGF pegylated aptamer (eye001) for the treatment of exudative age related macular degeneration," Retina 22(2) Abstract (1 page).
Thickett et al., 1999, "Vascular endothelial growth factor (VEGF) in inflammatory and malignant pleural effusions," Thorax, 54:707-710.
Tsuji et al., 2002, "Pictet-Spengler Reaction of Nitrones and Imines Catalyzed by Yb(OTf)3-TMSCI," Chem. Lett. 4:428-429.
Ueda et al., 2001, "Vascular Endothelial Growth Factor and its Receptors Expression in the Rat Eye," Acta Histochem. Cytochem. 34(5):329-335.
Uy et al., 2008, "Topical Bevacizumab and Ocular Surface Neovascularization in Patients With Stevens-Johnson Syndrome," Cornea, 27:70-73.
Venkov et al., 1999, "Synthesis of 2-acyltetrahydro-/3-carbolines by an intiamolecular a-amidoalkylation reaction", Synthetic Communications; 29(3):487-494.
Verheul et al., 2000, "Targeting Vascular Endothelial Growth Factor Blockade: Ascites and Pleural Effusion Formation," Oncologist, 5:45-50.
Wang et al., 1998, "Presence and possible role of vascular endothelial growth factor in thyroid cell growth and function," J. Endocrinol., 157:5-12.
Wasilewska et al., 2006, "Glucocorticoid receptor and vascular endothelial growth factor in nephrotic syndrome," Acta Paediatrica, 95:587-593.
Written Opinion of International Application PCT/US2010/036467, dated Jul. 28, 2010.
Written Opinion of the International Searching Authority dated Aug. 26, 2011 for International Application No. PCT/US11/38067, filed May 26, 2011.
Wu et al., 2002, "A Versatile Linkage Strategy for Solid-Phase Synthesis of N,N-Dimethyltryptamines and β-Carbolines," Organic Letters 4(23):4033-4036.
Xia et al., 2003, "Transgenic delivery of VEGF to mouse skin leads to an inflammatory condition resembling human psoriasis," Blood 102(1):161-168.
Kamada et al., 1998, "Chiral Lewis Acid-Mediated Enantioselective Pictet-Spengler Reaction of Nb-Hydroxytryptamine with Aldehydes," J. Org. Chem. 63(18):6348-6354.
Zheng et al., 2001, "Contribution of Vascular Endothelial Growth Factor in the Neovascularization Process during the Pathogenesis of Herpetic Stromal Keratitis," J. Virol. 75(20):9828-9835.

(56) References Cited

OTHER PUBLICATIONS

Padro et al., 2002, "Overexpression of vascular endothelial growth factor (VEGF) and its cellular receptor KDR (VEGFR-2) in the bone marrow of patients with acute myeloid leukemia," Leukemia 16:1302-1310.
Schuch et al., 2002, "In vivo administration of vascular endothelial growth factor (VEGF) and its antagonist, soluble neuropilin-1, predicts a role of VEGF in the progression of acute myeloid leukemia in vivo," Blood 100(13):4622-4628.
Ferrara et al., 2003, "The biology of VEGF and its receptors," Nature Medicine 9(6):669-676.
Giles, 2001, "The Vascular Endothelial Growth Factor (VEGF) Signaling Pathway: A Therapeutic Target in Patients with Hematologic Malignancies," The Oncologist 6(Suppl 5):32-39.
Moehler et al., 2004, "Antiangiogenic Therapy in Hematologic Malignancies," Current Pharmaceutical Design 10:1221-1234.
Acne Rosacea, http://www.webmd.com/skin-problems-and-treaLnients/ acne/acne-rosacea (last visited Sep. 14, 2014).
Adan et al., 2007, "Intravitreal bevacizumab as initial treatment for choroidal neovascularization associated with presumed ocular histoplasmosis syndrome," Graefes Arch. Clin. Exp. Ophthalmol., 245:1873-1875.
Ardill et al., 1990, "X=Y-ZH compounds as potential 1,3-dipoles. Part 29. The iminium ion route to azomethine y ides. Reaction of cyclic secondary amines with mono- and bi-functional aldehydes," Tetrahedron 46(18):6449-6466.
Audia et al., 1996, "Potent, Selective Tetrahydro-beta-carboline Antagonists of the Serotonin 2B (5HT2B) Contractile Receptor in the Rat Stomach Fundus," J. Med. Chem. 39:2773-2780.
Begum et al., 1996, "Chemistry and biological activity of a tryptamine and beta-carboline series of bases," Drug Research, 12(46):1163-1168.
Bello-Reuss et al., 2001, "Angiogenesis in autosomal-dominant polycyctic kidney disease," Kidney Int. 60:37-45.
Belzil, 2006, "Therapeutic Potential for Inhibition of HIV Activation," Lethbridge Undergrad. Res. J. 1(2):1-12.
Benevento et al., 2008, "Toxoplasmosis associated neovascular lesions treated successfully with ranibizumab and anti-parasitic therapy," Arch. Ophthalmol., 126(8); (8 Pages).
Berrougui et al., 2005, "Cytotoxic activity of methanolic extract and two alkaloids extracted from seeds of *Peganum harmala* L," Journal of Natural Remedies, 5(1):41-45.
Bhatnagar et al., 2007, "Intravitreal bevacizumab for the management of choroidal neovascularization in pseudoxanthoma elasticum," Retina, 27:897-902.
Boyer et al., 2002, "Small molecule inhibitors of KDR (VEGFR-2) kinase: an overview of structure activity relationships," Current Topics in Medicinal Chemistry, 2(9):973-1000.
Brown et al., 1995, "Increased expression of vascular permeability factor (vascular endothelial growth factor) in bullous pemphigoid, dermatitis herpetiformis, and erythema multiforme," J. Invest. Dermatol. 104:744-749.
Cao et al., 2005, "Synthesis and in vitro cytotoxic evaluation of 1,3-disubstituted and 1,3,9-trisubstituted beta-carboline derivatives," European Journal of Medicinal Chemistry; 40(3):249-257.
Cekmen et al., 2003, "Vascular endothelial growth factor levels are increased and associated with disease activity in patients with Behcet's syndrome," Int. J. Dermatol., 42:870-875.
Chan et al., 2008, "Changes in aqueous vascular endothelial growth factor and pigment epithelial-derived factor levels following intravitreal bevacizumab injections for choroidal neovascularization secondary to age-related macular degeneration or patholigic myopia," Retinal, 28:1308-1313.
Cleaveland et al., 1996, "Identification of a Novel Inhibitor (NSC 665564) of Dihydroorotate Dehydrogenase with a Potency Equivalent to Brequinar," Biochemical and Biophysical Research Communications, 223(3):654-659.
Corrected Notice of Allowability dated Nov. 18, 2013 for U.S. Appl. No. 13,321,233; (100 pages).

Database Accession No. 84862, 570837, 578504, 585452, 690268 (XRN) accompanied by Aghbalian et al., 1972, "Synthesis Based on Harmine and Tetrahydroharmine", Armyanskii Khimicheskii Zhurnal 25:689-692; Partial European Search Report for EP11178488 dated May 9, 2012; (8 Pages).
Database REAXYS [Online], Elsevier Information Systems GmbH, Frankfurt/Main; XP002675485, Database Accessior No. 84862,230057, 306267 (XRN), accompanied by Fischer, 1897, "Uber Harmin und Harmalin," Ber. Dtsch. Chem. Ges. 30(3):2481-2489; Fischer, 1901, "Chemische Studien der Alkaloideder Steppenraute (Peganum Harmala)," Chem. Zentralbl. 72(1):957-959; Partial European Search Report for EP11178488 dated May 9, 2012, p. 2.
Database REAXYS [Online], Elsevier Information Systems GmbH, Frankfurt/Main; XP002675486, Database Accessior No. 207280, 3918373 (XRN), accompanied by Fischer, 1914, "Uber Harmin und Harmalin," Ber. Dtsch. Chem. Ges. 47:99-107; Partial Europan Search Report for EP11178488 dated May 9, 2012; (11 Pages).
Database WPI Accession No. 1992-376264, Abstract of JP 4275221, 1992, Taisho Pharm. Co., Ltd; (1 Page).
Fava et al., 1994, "Vascular Permeability Factor/Endothelial Growth Factor (VPF/VEGF): Accumulation and Expression in Human Synovial Fluids and Rheumatoid Synovial Tissue," J. Exp. Med. 180(1):341-346.
Formagio et al., 2009, "Synthesis and antiviral activity of β-carboline derivatives bearing a substituted carbohydrazide at C-3 against poliovirus and herpes simplex virus (HSV-1)," Eur. J. Med. Chem. 44:4695-4701.
Fuhrmann-Benzakein et al., 2000, "Elevated levels of angiogenic cytokines in the plasma of cancer patients," International Journal of Cancer, 85(1):40-45.
Gareth, 2007, "Medicinal Chemistry: An Introduction," Second Edition, John Wiley & Sons Ltd., pp. 75-80.
Goitre (pathology)—Britannica Online Encyclopedia, http://www.britannica.com/EBchecked/topic/237190/goitre (last visited Sep. 13, 2014); (1 Page).
Grisanti et al., 2006, "Intracameral bevacizumab for iris rubeosis," Am. J. Ophthamol., 142:158-160.
Hamada et al. 2005, "Marked pleural and pericardial effusion with elevated vascular endothelial growth factor production: an uncommon complication of Kawasaki disease," Pediatr. Int., 47:112-114.
Hino et al., 1990, "2-Hydroxy-1-substituted-1,2,3,4-tetrahydro-β-carbolines. The Pictet-Spengler Reaction of N-Hydroxytryptamine with Aldehydes," Chem. Pharm. Bull. 38(1):59-64.
Hirawat et al., 2006, "51 Poster Phase 1 single-dose safety, PK, and food-effect study of PTC299, a novel VEGF expression inhibitor for trealment of solid tumors," European Journal of Cancer, Suppl 4(12):19-20.
Hirawat et al., 2007, "Phase 1 studies assessing the safety, PK and VEGF-modulating effects of PTC299, a novel VEGF expression inhibitor," Journal of Clinical Oncology ASCO Annual Meeting Proceedings Part 1; 25(1Ss):Abstract 3562; (1 Page).
Hyperplasia: MedlinePlus Medical Encyclopedia, http://www.nlm.nih.gov/medlineplus/ency/article/003441.htm (last visited Sep. 13, 2014); (1 Page).
Iakhontov et al., 1958, "Reduction of Derivatives of Harmine with Sodium Borohydride to Derivatives of Py-Tetrahydroharmine," Zhurnal Obshchei Khimii, 28(11):3139-3141.
Itaka et al., 1998, "Increased serum vascular endothelial growth factor levels and inlalhyroidal vascular area in patients with Graves' Disease and Hashimoto's Thyroiditis," J. Clin. Endocrinol. Metab., 83:3908-3912.
Inoue et al., 1998, "Vascular endothelial growth factor (VEGF) expression in human coronary atherosclerotic lesions Possible pathophysiological significance of VEGF in progression of atherosclerosis," Circulation 98:2108-2116.
International Search Report dated Aug. 26, 2011 for International Application No. PCT/US11/38067, filed May 26, 2011; (2 Pages).
International Search Report of International Application PCT/US2010/036467, dated Jul. 28, 2010; (2 Pages).
Ishida et al., 1999, "Antitumor Agents 201. Cytotoxicity of harmine and beta-carboline analogs," Bioorganic & Medicinal Chemistry Letters, 9(23):3319-3324.

(56) References Cited

OTHER PUBLICATIONS

Jackson et al., 1997, "Vascular endothelial growth factor (VEGF) expression in prostate cancer and benign prostatic hyperplasia," J. Urology, 157:2323-2328.
Jiang et al., 2003, "Potassium Superoxide as an Alternative Reagent for Winterfeldt Oxidation of β-Carbolines," Organic Letters, 5(1):43-46.
Kawashima et al., 1995, "Synthesis and Pharmacological Evaluation of 1,2,3,4-Tetrahydro-β-Carboline Derivatives," Chem. Pharm. Bull., 43(5):783-787.
Kawate et al., 1999, "Chiral Auxiliary Approach to the Asymmetric Pictet-Spengler Reaction of Tryptamines," Heterocycles 50(2):1033-1039.
Kikuchi et al., 2005, "Angiogenic cytokines in serum and cutaneous lesions of patients with polyarteritis nodosa," J. Am. Acad. Dermatol., 53:57-61.
Kupferminc et al., 1997, "Vascular endothelial growth factor is increased in patients with preeclampsia," Am. J. Reprod. Immunol., 38(4):302-306.
Kuryliszyn-Maskal et al., 2007, "Vascular endothelial growth factor in systemic lupus erythematosus relationship to disease activity, systemic organ manifestation, and nailfold capillaroscopic abnormalities," Arch. Immunol. Ther. Exp., 55:179-185.
Kvanta et al., 1996, "Subfoveal Fibrovascular Membranes in Age-Related Macular Degeneration Express Vascular Endothelial Growth Factor," Invest. Ophthalmol. Vis. Sci. 37(9):1929-1934.
Lashkari et al., 2000, "Vascular Endothelial Growth Factor and Hepatocyte Growth Factor Levels Are Differentially Elevated in Patients With Advanced Retinopathy of Prematurity,"Am. J. Pathol., 156:1337-1344.
Lee et al., 2004, "Vascular Endothelial Growth Factor (VEGF) induces remodeling and enhances TH2-mediated sensitization and inflammation in the lung," Nat. Med, 10:1095-1103.
Lehmann et al., 1987, "Lactamisation of 4.9-Dihydropyrano [3.4-b] indol-1 (3H)-ones.—A New Synthetic Route to the beta-Carboline Ring System," Archiv der Pharmazie 320(1):30-36.
Achen et al., 1998, "The vascular endothelial grown factor family; proteins which guide the development of the vasculature," Int. J. Exp. Pathol. 79:255-265.
Lehnert et al., 1994, "DNA topoisomerase II inhibition by substituted 1,2,3,4-tetrahydro-β-carboline derivatives," Bioorganic & Medicinal Chemistry Letters, 4(20):2411-2416.
Leu et al., 2007, "Choroidal neovascularisation secondary to Best's disease in a 13-year-old boy treated by intravitreal bevacizumab," Graefe's Arch. Clin. Exp. Ophthalmol., 245:1723-1725.
Lip et al., 2000, "Plasma VEGF and Soluble VEGF Receptor FLT-1 in Proliferative Retinopathy: Relationship to Endothelial Dysfunction and Laser Treatment," Invest. Ophthalmol. Vis. Sci. 41 (8):2115-2119.
Lopez et al., 1991, "Immunohistochemistry of Terrien's and Mooren's Corneal Degeneration," Arch. Ophthalmol., 109:988-992.
Macaron et al., 2003, "Cutaneous lesions of secondary syphilis are highly angiogenic," J. Am. Acad. Dermatol., 48:878-881.
Mastyugin et al., 2001, "Corneal epithelial VEGF and cytochrome P450 4BI expression in a rabbit model of closed eye contact lens wear," Curr. Eye Res., 23:1-10.
Matsuda et al., 2004, "Sarcoidosis with high serum levels of vascular endothelial growth factor (VEGF), showing RS3PE-like symptoms in extremities," Clin. Rheumatol., 23:246-248.
McColley et al., 2000, "Serum Vascular Endothelial Growth Factor is Elevated in Cystic Fibrosis and Decreases with Treatment of Acute Pulmonary Exacerbation," Am. J. Respir. Crit. Care Med., 161:1877-1880.
Mcnulty et al., 1991, "Diastereoselective Pictet-Spengler reaction of L-(Boc) prolinal: a biomimetic synthesis of eudistomins H and I, and woodinine," Tetrahedron Letters 32(37):4875-4878.
Miller et al., 2010, "Substituted tetrahydro-β-carbolines as potential agents for the treatment of human papillomavirus infection," Bioorg. Med. Chem. Lett. 20:256-259.

Nicolaus et al., 1983, "Symbiotic approach to drug design", Decision Making in Drug Research; pp. 173-186.
Nishigaki et al., 2006, "Increased serum level of vascular endothelial growth factor in *Mycobacterim aviumcomplex* Infection," Respirology 11:407-413.
Notice of Allowance dated Dec. 6, 2013 for U.S. Appl. No. 13/321,213.
Notice of Allowance dated Nov. 7, 2013 for U.S. Appl. No. 13/321,233.
Office Action dated Apr. 25, 2013 for U.S. Appl. No. 13/321,233, filed Mar. 9, 2012.
Office Action dated Jul. 11, 2014 for U.S. Appl. No. 13/321,242, filed Mar. 9, 2012.
Office Action dated Jul. 16, 2014 for U.S. Appl. No. 13/321,252, filed Mar. 9, 2012.
Office Action dated Mar. 20, 2015 for U.S. Appl. No. 13/321,252, filed Mar. 9, 2012.
Office Action dated Mar. 24, 2015 for U.S. Appl. No. 13/321,242, filed Mar. 9, 2012.
Office Action dated May 9, 2013 for U.S. Appl. No. 13/321,213, filed Mar. 23, 2012.
Office Action dated Nov. 21, 2014 for U.S. Appl. No. 13/321,271, filed Mar. 23, 2012.
Office Action dated Oct. 8, 2013 for U.S. Appl. No. 13/321,271, filed Mar. 23, 2012.
Paroli et al., 2007, "Increased vascular endothelial growth factor levels in aqueous humor and serum of patients with quiescent uveitis," Eur. J. Ophthalmol., 17:938-942.
Pe'er et al., 1998, "Vascular Endothelial Growth Factor Upregulation in Human Cenlral Retinal Vein Occlusion," Ophthalmology, 105:412-416.
Perentes et al., 2002, "Massive vascular endothelium growth factor (VEGF) expression in Eales' disease," Klin. Monatsbl. Augenheilkd., 219:311-314.
Philipp et al., 2002, "Expression of Vascular Endothelial Growth Factors, Vegf-B, Vegf-C, Vegf-D, and of VegfC Receptors, Flt-4 (VEGFR-3) in Inflamed and Vascularized Human Corneas," AVRO Meeting Abstracts, 43:1755.
Plate et al., 1993, "Up-regulation of vascular endothelial growth factor and its cognate receptors in a rat glioma model of tumor angiogenesis," Cancer Res. 53(23):5822-5827.
Polyarteritis Nodosa (PAN): Vasculitis: Merck Manual Professional, http://www.merckmanuals.com/professional/musculoskeletal_and_connective_tissue_disorders/vasculitis/polyarteritis_nodosa_pan.html (last visited Sep. 14, 2014).
Qian et al., 2008, "Combined Use of Superficial Keratectomy and Subcontjunceval Bevacizumab Injection for Corneal Neovascularization," Cornea, 27:1090-1092.
Querques et al., 2008, "Intravitreal ranibizumab (Lucentis) for choroidal neovascularization associated with Stargardt's disease," Graefes Arch. Clin. Exp. Ophthalmol., 246:319-321.
Ray et al., 2004, "Association of the VEGF Gene With Proliferative Diabetic Retinopathy but Not Proteinuria in Diabetes," Diabetes 53:861-864.
Rubtsov et al., 1959, "Synthesis of Py-N-Alkyltetrahydroharmines" Zhurnal Obshchei Khimii 29:3232-3235.
Saaristo et al., 2000, "Mechanisms of angiogenesis and their use in the inhibition of tumor growth and metastasis," Oncogene 19:6122-6129.
Sachanonta et al., 2008, "Host Vascular Endothelial Growth Factor is Trophic for Plasmodium Falciparum-Infected Red Blood Cells," Asian Pac. J. Allergy 26:37-45.
Saiga et al., 1987, "Synthesis of 1,2,3,4-tetrahydro-beta-carboline derivatives as hepatoprotective agents. III. Introduction of substituents onto methyl 1,2,3,4-tetrahydro-beta-carboline-2-carbodithioate," Chem. Pharm. Bull. 35(8): 3284-3291.
Schoenenberger et al., 1986, "Fragmentation of Optically Active (1-Phenylethyl)- and (1-Naphthylethyl) ureas in Refluxing Alcohols: Easy Preparation of Optically Active Amines of High Optical Purity," Helvetica Chimica Acta 69(6):1486-1497.
Schreiber et al., 2003, "Combined Topical Fluconazole and Corticosteroid Treatment for Experimental Candida Albicans Keratomycosis," Invest. Ophthal. Vis. Sci., 44:2634-2643.

(56) References Cited

OTHER PUBLICATIONS

Shah et al., 2007, "Intravitreal bevacizumab (Avastin) for post laser anterior segment ischemia in aggressive posterior retinopathy of prematurity," Indian J. Ophthalmol., 55:75-76.
Siddiqui et al., 1992, "Preparation of Tetrahydroharmine Analogues—Their Antibacterial, Bronchodilator and Cytotoxic Activity and Effect on Cenlral Nervous System," Proc. Pakistan Acad. Sci. 29(4):285-298.
Silha et al., 2005, "Angiogenic factors are elevated in overweight and obese individuals," Int. J. Obes. 29:1308-1314.
Smith et al., 2007, "Expression of vascular endothelial growth factor and its receptors in rosacea," Br. J. Ophthalmol. 91:226-229.
Soe et al., 1995, "Asymmetric Pictet-Spengler Reaction with a Chiral N-(β-3-indolyl)-ethyl-l-methylbenzylamine," Tetrahedron Letters 36(11):1857-1860.
Solomina et al., 1990, "Synthesis and Pharmacological Properties of 1-R-2-[3'-R'-Amino-2-Hydroxypropyl]-1,2,3,4-Tetrahydro-β-Carbolines," Pharmaceutical Chemistry Journal, 24(4):272-275.
Solovey et al., 1999, "Sickel Cell Anemia as a Possible State of Enhanced Anti-Apoptotic Tone: Survival Effect of Vascular Endothelial Growth Factor on Circulating and Unanchored Endothelial Cells," Blood 93:3824-3830.
Stompor et al., 2002, "Selected growth factors in peritoneal dialysis: their relationship to markers of inflammation, dialysis adequacy, residual renal function, and peritoneal membrane transport," Perit. Dial. Int. 22: 670-676.
Taichman et al., 1997, "Human neutrophils secrete vascular endothelial growth factor," J. Leukoc. Biol. 62:397-400.
Takamiya et al., 1993, "Inhibition of angiogenesis and growth of human nerve-sheath tumors by AGM-1470," J. Neurosurg. 78(3):470-476.
Tasman et al., 2006, "Retinopathy of Prematurity: The Life of a Lifetime Disease," Am. J. Ophthalmol. 141:167-174.
Amatangelo, et al., "Enasidenib induces acute myeloid leukemia cell differentiation to promote clinical response," Blood. 2017;130(6):732-741.
Bardeleben, et al., "Metabolomics Identifies Pyrimidine Starvation as the Mechanism of 5-Aminoimidazole-4-Darboxamide-1-β-Riboside-Induced Apoptosis in Multiple Myeloma Cells," Mol Cancer Ther; 12(7); 1310-21 (2013).
Barretina, et al., "The Cancer Cell Line Encyclopedia enables predictive modeling of anticancer drug sensitivity," Nature. 483(7391): 603-607. doi: 10.1038/nature11003 (2012).
Basso, et al., "The two sides of a lipid-protein story," Biophys Rev (2016) 8:179-191. DOI 10.1007/s12551-016-0199-5.
Baumann, et al., "Dihydroorotate dehydrogenase inhibitor A771726 (leflunomide) induces apoptosis and diminishes proliferation of multiple myeloma cells," Mol Cancer Ther 2009;8(2):366-75.
Bender Ignacio, et al., "Brief Report: Clinical Science, A Phase 1 b/Pharmacokinetic Trial of PTC299, a Novel PostTranscriptional VEGF Inhibitor, for AIDS-Related Kaposi's Sarcoma: AIDS Malignancy Consortium Trial 059," J Acquir Immune Defic Syndr 2016;72:52-57.
Berg, et al., "Characterization of compound mechanisms and secondary activities by BioMAP analysis," Journal of Pharmacological and Toxicological Methods 53 (2006) 67-74.
Brand and Nicholls, "Assessing mitochondrial dysfunction in cells," Biochem. J. (2011) 435, 297-312. doi:10.1042/BJ20110162.
Cacciamani, et al., "Purification of Human Cytidine Deaminase: Molecular and Enzymatic Characterization and Inhibition by Synthetic Pyrimidine Analogs," Archives of Biochemistry and Biophysics, vol. 290, No. 2, Nov. 1, pp. 285-292, 1991.
Cao, et al., "PTC299 Is a Novel DHODH Inhibitor That Modulates VEGFA mRNA Translation and Inhibits Proliferation of a Broad Range of Leukemia Cells," Blood (2017) 130 (Supplement 1): 1371. (Abstract) https://doi.org/10.1182/blood.V130.Suppl_1.1371.1371.
Cao, et al., "Targeting of Hematologic Malignancies with PTC299, A Novel Potent Inhibitor of Dihydroorotate Dehydrogenase with Favorable Pharmaceutical Properties," Mol Cancer Ther; 2019;18:3-16. doi:10.1158/1535-7163. MCT-18-0863.
Carlile, et al., "Pseudouridine profiling reveals regulated mRNA pseudouridylation in yeast and human cells," Nature. Nov. 6, 2014; 515(7525): 143-146. doi:10.1038/nature13802.
Chen, et al., "Inhibition of Dihydroorotate Dehydrogenase Activity by Brequinar Sodium," Cancer Research 52, 3521-3527, Jul. 1, 1992.
Clayton and Shadel, "Isolation of Mitochondria from Cells and Tissues" Cold Spring Harb Protoc (2014) 1040-1041. doi:10.1101/pdb.top074542.
Cody, et al., "Multicenter Phase II Study of Brequinar Sodium in Patients with Advanced Breast Cancer," Am J Clin Oncol (CCT) 16(6): 526-528, 1993.
Cunningham, et al., "Protein and nucleotide biosynthesis are coupled through a single rate limiting enzyme, PRPS2, to drive cancer," Cell. May 22, 2014; 157(5): 1088-1103. doi:10.1016/j.cell.2014.03.052.
Deans, et al., "Parallel shRNA and CRISPR-Cas9 screens enable antiviral drug target identification," Nat Chem Biol. May 2016 ; 12(5): 361-366. doi:10.1038/nchembio.2050.
Diedrichs-Möhring, et al., "Intraocular DHODH-inhibitor PP-001 suppresses relapsing experimental uveitis and cytokine production of human lymphocytes, but not of RPE cells," Journal of Neuroinflammation (2018)15:54, 1-11. https://doi.org/10.1186/s12974-018-1088-6.
Dietrich, et al., "IKAP expression levels modulate disease severity in a mouse model of familial dysautonomia," Human Molecular Genetics, 2012, vol. 21, No. 23, 5078-5090. doi:10.1093/hmg/dds354.
Dranka, et al., "Mitochondrial reserve capacity in endothelial cells: the impact of nitric oxide and reactive oxygen species," Free Radic Biol Med. Apr. 1, 2010; 48(7): 905-914. doi:10.1016/j.freeradbiomed.2010.01.015.
Duley, et al., "Elevated plasma dihydroorotate in Miller syndrome: Biochemical, diagnostic and clinical implications, and treatment with uridine," Molecular Genetics and Metabolism 119 (2016) 83-90.
Eakins, et al., "A combined in vitro approach to improve the prediction of mitochondrial toxicants," Toxicology in Vitro, 34 (2016) 161-170.
Mohamad Fairus, et al., "Dihydroorotate dehydrogenase (DHODH) inhibitors affect ATP depletion, endogenous ROS and mediate S-phase arrest in breast cancer cells," Biochimie 135 (2017) 154-163.
Fitzpatrick, et al., "Vidofludimus Inhibits Colonic IL-17 and Improves Hapten-Induced Colitis in Rats by a Unique Dual Mode of Action," JPET Jun. 12, 2012. DOI: 10.1124/jpet.112.192203.
Fox, et al., "Short Analytical Review Mechanism of Action for Leflunomide in Rheumatoid Arthritis," Clinical Immunology, vol. 93, No. 3, December, pp. 198-208, 1999.
Gaborit, et al., "Plea for multitargeted interventions for severe COVID-19," www.thelancet.com/infection, vol. 20, Oct. 2020, 1122-1123. https://doi.org/10.1016/S1473-3099(20)30312-1.
Gong, et al., "Correlation Analysis Between Disease Severity and Inflammation-related Parameters in Patients with DOVID-19 Pneumonia," Feb. 27, 2020 (17 pages). https://doi.org/10.1101/2020.02.25.20025643.
Greene, et al., "Inhibition of Dihydroorotate Dehydrogenase by the Immunosuppressive Agent Leflunomide," Biochemical Pharmacology, vol. 50, No. 6, pp. 861-867, 1995.
Hall, et al., "Liver Hypertrophy: A Review of Adaptive (Adverse and Non-adverse) Changes—Conclusions from the 3rd International ESTP Expert Workshop," Toxicologic Pathology, 40: 971-994, 2012.
Huang, et al., "Clinical features of patients infected with 2019 novel coronavirus in Wuhan, China," Lancet 2020; 395: 497-506. https://doi.org/10.1016/S0140-6736(20)30183-5.
Jain, A.N., "Effects of protein conformation in docking: improved pose prediction through protein pocket adaptation." J Comput Aided Mol Des (2009) 23:355-374.

(56) References Cited

OTHER PUBLICATIONS

Jain, A.N., "Surflex: Fully Automatic Flexible Molecular Docking Using a Molecular Similarity-Based Search Engine," J. Med. Chem. 2003, 46, 499-511.

Kunkel, et al., "An integrative biology approach for analysis of drug action in models of human vascular inflammation," The FASEB Journal, Jun. 18, 2004, 21 pages. https://doi.org/10.1096/fj.04-1538fje.

Kunkel, et al., "Rapid Structure-Activity and Selectivity Analysis of Kinase Inhibitors by BioMAP Analysis in Complex Human Primary Cell-Based Models," ASSAY and Drug Development Technologies, vol. 2, No. 4, 2004, 431-441.

Kut, et al., "Where is VEGF in the body? A meta-analysis of VEGF distribution in cancer," British Journal of Cancer (2007) 97, 978-985.

Lane and Fan, "Survey and Summary Regulation of mammalian nucleotide metabolism and biosynthesis," 2466-2485, Nucleic Acids Research, 2015, vol. 43, No. 4. doi: 10.1093/nar/gkv047.

Lewis, et al., "Development of ML390: A Human DHODH Inhibitor That Induces Differentiation in Acute Myeloid Leukemia," ACS Med. Chem. Lett. 2016, 7, 1112-1117. DOI: 10.1021/acsmedchemlett.6b00316.

Luban, et al., "The DHODH inhibitor PTC299 arrests SARS-CoV-2 replication and suppresses induction of inflammatory cytokines," Virus Research 292 (2021) 198246 (11 pages).

Ma, et al., "Inhibition of hepatic cytochrome P450 enzymes and sodium/bile acid cotransporter exacerbates leflunomide-induced hepatotoxicity," Acta Pharmacologica Sinica (2016) 37: 415-424; doi: 10.1038/aps.2015.157; published online Jan. 25, 2016.

Maronpot, et al., "Hepatic Enzyme Induction: Histopathology," Toxicologic Pathology, 38: 776-795, 2010. DOI: 10.1177/0192623310373778.

McLean, et al., "Discovery of novel inhibitors for DHODH via virtual screening and X-ray crystallographic structures," Bioorganic & Medicinal Chemistry Letters, 20 (2010) 1981-1984.

Moore and June, "Cytokine release syndrome in severe COVID-19," May 1, 2020, Science, 368 (6490), DOI: 10.1126/science.abb8925, 473-474.

Muehler, et al., "Vidofludimus calcium, a next generation DHODH inhibitor for the Treatment of relapsing-remitting multiple sclerosis," Multiple Sclerosis and Related Disorders, 43 (2020) 102129 (8 pages).

Nassereddine, et al., "The role of mutant IDH1 and IDH2 inhibitors in the treatment of acute myeloid leukemia," Ann Hematol (2017) 96:1983-1991. https://doi.org/10.1007/s00277-017-3161-0.

Ohnuma, et al., "Pharmacological and Biochemical Effects of Pyrazofurin in Humans," Cancer Res 1977; 37:2043-2049.

Package Insert for ritonivar (NORVIR®), 2019 (49 pages).

Packer, et al., "Phase I and Pharmacokinetic Trial of PTC299 in Pediatric Patients with Refractory or Recurrent Central Nervous System Tumors: a PBTC Study," J Neurooncol, Jan. 2015; 121(1): 217-224. doi: 10.1007/s11060-014-1665-1.

Perez and Briz, "Bile-acid-induced cell injury and protection," World J Gastroenterol Apr. 14, 2009; 15(14):1677-1689. doi:10.3748/wjg.15.1677.

Peters, et al., "In Vivo Inhibition of the Pyrimidine de Novo Enzyme Dihydroorotic Acid Dehydrogenase by Brequinar Sodium (DUP-785; NSC 368390) in Mice and Patients," Cancer Res 1990;50:4644-4649.

Peters, et al., "Inhibition of pyrimidine de novo synthesis by DUP-785 (NSC 368390)," Investigational New Drugs, 5:235-244, 1987.

Plotkin, et al., "Hearing Improvement after Bevacizumab in Patients with Neurofibromatosis Type 2," N Engl J Med 2009;361:358-67.

Raimondo, et al., "Elevated vascular endothelial growth factor (VEGF) serum levels in idiopathic myelofibrosis," Leukemia (2001) 15, 976-980.

Rawls, et al., "Requirements for the mitochondrial import and localization of dihydroorotate dehydrogenase," Eur. J. Biochem., 267, 2079-2087 (2000).

Saini, et al., "Regulatory elements in eIF1A control the fidelity of start codon selection by modulating tRNA;$^{Met}$ binding to the ribosome," Genes & Development 24:97-110 (2010).

Sekiya and Yoshimura, "Chapter 10: In Vitro Th Differentiation Protocol," Xin-Hua Feng et al. (eds.), TGF-β Signaling: Methods and Protocols, Methods in Molecular Biology, vol. 1344, DOI 10.1007/978-1-4939-2966-5_10 (2016) 183-191.

Sharma, et al., "Targeting mTORC1-Mediated Metabolic Addiction Overcomes Fludarabine Resistance in Malignant B Cells," Mol Cancer Res; 12(9); 1205-15 (2014).

Shen, et al., "Discovery of a new structural class of competitive hDHODH inhibitors with in vitro and in vivo anti-inflammatory, immunosuppressive effects," European Journal of Pharmacology 791 (2016) 205-212.

Sykes, et al., "Inhibition of Dihydroorotate Dehydrogenase Overcomes Differentiation Blockade in Acute Myeloid Leukemia," 2016, Cell 167, 171-186.

Vélez, et al., "Mitochondrial uncoupling and the reprograming of intermediary metabolism in leukemia cells," Frontiers in Oncology, Molecular and Cellular Oncology, Apr. 2013, vol. 3, Article 67, 1-8. doi: 10.3389/fonc.2013.00067.

Wang, et al., "Enhancement of arabinocytosine (AraC) toxicity to AML cells by a differentiation agent combination," Journal of Steroid Biochemistry & Molecular Biology, 164 (2016) 72-78.

Wu and Yang, "TH17 responses in cytokine storm of COVID-19: An emerging target of JAK2 inhibitor Fedratinib," Journal of Microbiology, Immunology and Infection (2020) 53, 368-370.

Xiong, et al., "Novel and potent inhibitors targeting DHODH are broad-spectrum antivirals against RNA viruses including newly-emerged coronavirus SARS-CoV-2," Protein Cell, 2020, 11(10):723-739. https://doi.org/10.1007/s13238-020-00768-w.

Xu, et al., "In Vitro and In Vivo Mechanisms of Action of the Antiproliferative and Immunosuppressive Agent, Brequinar Sodium," The Journal of Immunology, 1998, 160: 846-853.

Xu, et al., "Two Activities of the Immunosuppressive Metabolite of Leflunomide, A77 1726 Inhibition of Pyrimidine Nucleotide Synthesis and Protein Tyrosine Phosphorylation," Biochemical Pharmacology, vol. 52, pp. 527-534, 1996.

Yen, et al., "AG-221, a First-in-Class Therapy Targeting Acute Myeloid Leukemia Harboring Oncogenic IDH2 Mutations," Cancer Discov; 7(5); 478-93 (2017).

Zhang, et al., "Metabolomics profiles delineate uridine deficiency contributes to mitochondria-mediated apoptosis induced by celastrol in human acute promyelocytic leukemia cells," Oncotarget, vol. 7, No. 29 (2016) 46557-46572.

Branstrom, et al., "Emvododstat, a Potent Dihydroorotate Dehydrogenase Inhibitor, is Effective in Preclinical Models of Acute Myeloid Leukemia", Front. Oncol. 12:832816 (2022) 1-13. doi: 10.3389/fonc.2022 832816.

Fiedler, et al., "An open-label, Phase I study of cediranib (RECENTIN™) in patients with acute myeloid leukemia", Leukemia Research 34 (2010) 196-202.

Cao, et al., "PTC299 is a Novel DHODH Inhibitor That Modulates VEGFA mRNA Translation and Inhibits Proliferation of a Broad Range of Leukemia Cells," Poster #1371, ASH (American Society of Hematology) Annual Meeting 2017, Atlanta Georgia, Dec. 9-12, 2017.

Berber and Doluca, "A comprehensive drug repurposing study for COVID19 treatment: novel putative dihydroorotate dehydrogenase inhibitors show association to serotonin-dopamine receptors," Briefings in Bioinformatics, 22(2), 2021, 1023-1037. doi: 10.1093/bib/bbaa379.

Immunic Therapeutics, IMU-838 Targeting DHODH.

Immunic Therapeutics, "IMU-838 Vidofludimus calcium (IMU-838) is a small molecule investigational drug under development as an oral tablet formulation for the treatment of relapsing-remitting multiple sclerosis, or RRMS, inflammatory bowel disease, or IBD, and other chronic inflammatory and autoimmune diseases," Retrieved from the Internet: https://imux.com/pipeline/imu-838/ [retrieved on Mar. 29, 2022].

Xiong, et al., "Novel and potent inhibitors targeting DHODH, a rate-limiting enzyme in de novo pyrimidine biosynthesis, are broad-

(56) References Cited

OTHER PUBLICATIONS spectrum antivirals against RNA viruses including newly emerged coronavirus SARS-CoV-2," Mar. 12, 2020, https://doi.org/10.1101/2020.03.11.983056.

Chen, et al., "Suppression of pyrimidine biosynthesis by targeting DHODH enzyme robustly inhibits rotavirus replication," Antiviral Research 167 (2019) 35-44. https://doi.org/10.1016/j.antiviral.2019.04.005.

Chen, et al., "Diagnosis and treatment recommendations for pediatric respiratory infection caused by the 2019 novel coronavirus," World Journal of Pediatrics, Published online: Feb. 5, 2020 (7 pages). https://doi.org/10.1007/s12519-020-00345-5.

Cheung, et al., "Broad-spectrum inhibition of common respiratory RNA viruses by a pyrimidine synthesis inhibitor with involvement of the host antiviral response," Journal of General Virology 2017;98:946-954. DOI 10.1099/jgv.0.000758.

Chien, et al., "Temporal changes in cytokine/chemokine profiles and pulmonary involvement in severe acute respiratory syndrome," Respirology (2006) 11, 715-722. doi: 10.1111/j.1400-1843.2006.00942.x.

Cox Dunn, et al., "Inhibition of respiratory syncytial virus in vitro and in vivo by the immunosuppressive agent leflunomide," Antiviral Therapy 2011; 16:309-317 (doi: 10.3851/IMP1763).

Danila, et al., "CirculatingTumor Cell No. and Prognosis in Progressive Castration-Resistant Prostate Cancer," Clin Cancer Res 2007;13(23) 7053-7058.

Hoffmann, et al., "Broad-spectrum antiviral that interferes with de novo pyrimidine biosynthesis," PNAS, Apr. 5, 2011, vol. 108, No. 14, 5777-5782. www.pnas.org/cgi/doi/10.1073/pnas.1101143108.

Liu, et al., "Clinical and biochemical indexes from 2019-nCoV infected patients linked to viral loads and lung injury," Sci China Life Sci, Mar. 2020 vol. 63 No. 3, 364-374. https://doi.org/10.1007/s11427-020-1643-8.

Lolli, et al., "Use of human Dihydroorotate Dehydrogenase (hDHODH) Inhibitors in Autoimmune Diseases and New Perspectives in Cancer Therapy," Recent Patents on Anti-Cancer Drug Discovery, 2018, 13, 86-105. DOI: 10.2174/1574892812666171108124218.

Lucas-Hourani, et al., (2013) "Inhibition of Pyrimidine Biosynthesis Pathway Suppresses Viral Growth through Innate Immunity," PLoS Pathog 9(10): e1003678. doi:10.1371/journal.ppat.1003678.

Lucas-Hourani, et al., "Original 2-(3-Alkoxy-1H-pyrazol-1-yl)azines Inhibitors of Human Dihydroorotate Dehydrogenase (DHODH)," J. Med. Chem. 2015, 58, 5579-5598. DOI: 10.1021/acs.medchem.5b00606.

Mei-Jiao Gong, et al., "Antiviral effects of selected IMPDH and DHODH inhibitors against foot and mouth disease virus," Biomedicine & Pharmacotherapy 118 (2019) 109305 (7 pages). https://doi.org/10.1016/j.biopha.2019.109305.

Miller, et al., "Substituted tetrahydro-b-carbolines as potential agents for the treatment of human papillomavirus infection," Bioorganic & Medicinal Chemistry Letters 20 (2010) 256-259. doi:10.1016/j.bmcl.2009.10.123.

Munier-Lehmann, et al., "On Dihydroorotate Dehydrogenases and Their Inhibitors and Uses," J. Med. Chem. 2013, 56, 3148-3167. dx.doi.org/10.1021/jm301848w.

Munier-Lehmann, et al., "Original 2-(3-Alkoxy-1H-pyrazol-1-yl)pyrimidine Derivatives as Inhibitors of Human Dihydroorotate Dehydrogenase (DHODH)," J. Med. Chem. 2015, 58, 860-877. DOI: 10.1021/jm501446r.

Nazari Formagio, et al., "Synthesis and antiviral activity of β-carboline derivatives bearing a substituted carbohydrazide at C-3 against poliovirus and herpes simplex virus (HSV-1)," European Journal of Medicinal Chemistry 44 (2009) 4695-4701. doi:10.1016/j.ejmech.2009.07.005.

Ortiz-Riaño, et al., "Inhibition of Arenavirus by A3, a Pyrimidine Biosynthesis Inhibitor," Journal of Virology p. 878-889, Jan. 2014 vol. 88 No. 2. doi:10.1128/JVI.02275-13.

Shaffer, et al., "CirculatingTumor Cell Analysis in Patients with Progressive Castration-Resistant Prostate Cancer," Clin Cancer Res 2007;13(7) Apr. 1, 2007, 2023-2029. doi:10.1158/1078-0432.CCR-06-2701.

Shanafelt, et al., "Phase II Trials of Single Agent Anti-VEGF Therapy for Patients with Chronic Lymphocytic Leukemia (CLL)," Leuk Lymphoma. Dec. 2010; 51(12): 2222-2229. doi:10.3109/10428194.2010.524327.

Siemeister, et al., "The pivotal role of VEGF in tumor angiogenesis: Molecular facts and therapeutic opportunities," Cancer and Metastasis Reviews 17: 241-248, 1998.

Sykes, David B., (2018) "The emergence of dihydroorotate dehydrogenase (DHODH) as a therapeutic target in acute myeloid leukemia," Expert Opinion on Therapeutic Targets, 22:11, 893-898, DOI: 10.1080/14728222.2018.1536748.

Wang, et al., "Inhibition of Dengue Virus through Suppression of Host Pyrimidine Biosynthesis," Journal of Virology, Jul. 2011, vol. 85, No. 13, p. 6548-6556. doi:10.1128/JVI.02510-10.

Wong, et al., "Plasma inflammatory cytokines and chemokines in severe acute respiratory syndrome," Clin Exp Immunol 2004; 136:95-103. doi:10.1111/j.1365-2249.2004.02415.x.

Yang, et al., "Novel AR-12 derivatives, P12-23 and P12-34, inhibit flavivirus replication by blocking host de novo pyrimidine biosynthesis," Emerging Microbes & Infections (2018) 7:187. DOI 10.1038/s41426-018-0191-1.

Yuen, KY and Wong, SSY, "Human infection by avian influenza A H5N1," Hong Kong Med J 2005;11:189-99.

Zhang, et al., "Analysis of Serum Cytokines in Patients with Severe Acute Respiratory Syndrome," Infection and Immunity, Aug. 2004, vol. 72, No. 8, p. 4410-4415. DOI: 10.1128/IAI.72.8.4410-4415.2004.

Barbosa et al., "Acute Myeloid Leukemia Driven by the CALM-AF10 Fusion Gene is Dependent on BMI1", Jan. 18, 2019, 25 pages.

Liangxian Cao et al., "Targeting of Hematologic Malignancies with PTC299, A Novel Potent Inhibitor of Dihydroorotate Dehydrogenase with Favorable Pharmaceutical Properties", Molecular Cancer Therapeutics, vol. 18, No. 1, pp. 3-16, Oct. 23, 2018.

Lucas-Hourani, et al., "Original Chemical Series of Pyrimidine Biosynthesis Inhibitors That Boost the Antiviral Interferon Response," Antimicrobial Agents and Chemotherapy Oct. 2017 vol. 61 Issue 10 e00383-17. https://doi.org/10.1128/AAC.00383-17.

Nishida et al., "The novel BMI-1 inhibitor PTC596 downregulates MCL-1 and induces p53-independent mitochondrial apoptosis in acute myeloid leukemia progenitor cells", Blood Cancer Journal, (2017) 7, e527, pp. 1-9.

Susha, "PTC299 inhibits SARS-CoV-2 replication and suppresses production of inflammatory cytokines", Dec. 1, 2020, Virus Research, 2020, https://doi.org/10.1016/j.virusres.2020.198246, http://www.sciencedirect.com/science/article/pii/S0168170220311539.

International Search Report for PCT/US2020/013645, dated May 15, 2020.

Written Opinion of the International Searching Authority for PCT/US2020/013645, dated May 15, 2020.

DHODH INHIBITOR FOR USE IN TREATING HEMATOLOGIC CANCERS

CROSS-REFERENCE TO RELATED APPLICATIONS

This application is a National Stage of International Application No. PCT/US2018/044862, filed Aug. 1, 2018, which claims the benefit of United States Provisional Patent Application No. 62/540,051, filed Aug. 1, 2017; and U.S. Provisional Patent Application No. 62/617,180, filed Jan. 13, 2018, each of the foregoing is incorporated by reference herein in its entirety and for all purposes.

INTRODUCTION

Cancer cells drive uncontrolled proliferation by regulating and integrating multiple biosynthetic processes, consequently affecting nucleotide and protein expression [16]. One of the affected biosynthetic processes is the expression of dihydroorotate dehydrogenase (DHODH), a rate-limiting enzyme whose function regulating de novo biosynthesis of pyrimidine nucleotides [1] is affected during uncontrolled cell cycle division. Consistent with such an effect, small molecule inhibition of DHODH function has recently been shown to prevent growth of several hematological cancers [2-4] where the hematological cancer is characterized by reduced expression of uridine salvage enzymes and a higher dependence on de novo pyrimidine nucleotide synthesis.

Another affected biosynthetic process in certain hematological cancers (~13%) is the disregulated expression of a mutant isocitrate dehydrogenase (mIDH) protein. Some inhibitors functioning as antiproliferative agents demonstrate selectivity for mutant IDH1 or mutant IDH2 over wildtype enzyme [29, 30], while other small molecules such as enasidenib have recently been shown to selectively inhibit mutant IDH2 enzyme activity [31].

Accordingly, there remains a great need for useful chemotherapeutic agents having potent inhibition of DHODH functional activity, favorable pharmaceutical properties and extensive clinical experience for use in treating such hematological cancers. In other instances, useful combinations of chemotherapeutic agents having synergistic antiproliferative activity, inhibiting both DHODH functional activity and IDH enzyme activity are desired for treating hematological cancers in subjects having high unmet medical need.

SUMMARY 4-chlorophenyl (S)-6-chloro-1-(4-methoxyphenyl)-1,3,4,9-tetrahydro-2H-pyrido[3,4-b]indole-2-carboxylate is a pharmacologically active enantiomer (hereinafter referred to as "Cpd 1" or "Cpd 1 S-enantiomer"), having the structure:

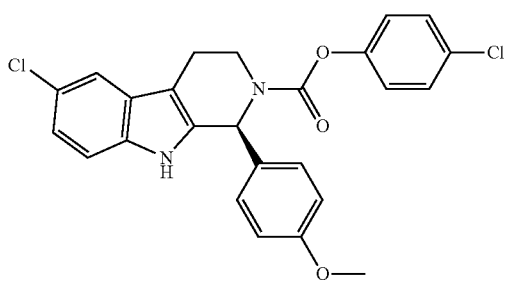 [SMILES: COc1ccc([C@H]2c3[nH]c4ccc(Cl)cc4c3CCN2C(=O)Oc2ccc(Cl)cc2)cc1]

Cpd 1 has demonstrated potent activity as an inhibitor of dihydroorotate dehydrogenase (DHODH) function, showing broad and potent activity against hematological cancers in both in vitro and in vivo preclinical and clinical studies. Moreover, a combination therapy of an inhibitor of mutant isocitrate dehydrogenase (mIDH) function with Cpd 1, an inhibitor of DHODH function, has recently been discovered as a potentiator of the antiproliferative effect of both mutant and wildtype IDH1 and IDH2 cells.

Provided herein is a method of use for Cpd 1 or a form or pharmaceutical composition thereof as an inhibitor of dihydroorotate dehydrogenase (DHODH) function in treating or ameliorating a hematological cancer in a subject in need thereof comprising, administering to the subject an effective amount of Cpd 1. More particularly, the hematological cancer is a leukemia or myelodysplastic syndrome (MDS) characterized by reduced expression of uridine salvage enzymes and dependence on de novo pyrimidine nucleotide synthesis. Also provided herein is a method of use for Cpd 1 or a form or pharmaceutical composition thereof in combination with other chemotherapeutic agents having additive and synergistic activity for inhibiting functional activity of both DHODH and IDH.

BRIEF DESCRIPTION OF THE FIGURES

FIG. 4a compares Cpd 1 overall activity in hematopoietic cell lines with solid cancer cell lines relative to FIG. 5a.

DETAILED DESCRIPTION

Provided herein is a method of use for Cpd 1 or a form or pharmaceutical composition thereof as an inhibitor of dihydroorotate dehydrogenase (DHODH) function in treating or ameliorating a hematological cancer in a subject in need thereof comprising, administering an effective amount of Cpd 1 to the subject, having the structure:

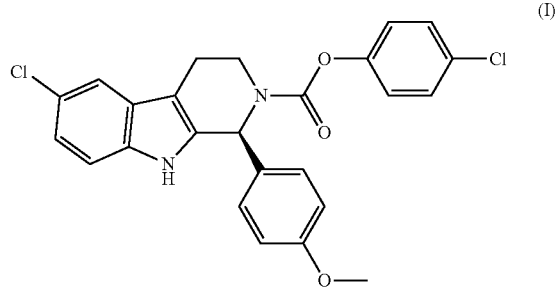 [SMILES: COc1ccc([C@H]2c3[nH]c4ccc(Cl)cc4c3CCN2C(=O)Oc2ccc(Cl)cc2)cc1]

(I)

or a form or pharmaceutical composition thereof.

Comparative Gene Expression Analysis

The identification of Cpd 1 as an inhibitor of DHODH function for selective use in treating or ameliorating a hematological cancer was obtained from a gene expression analysis comparing Cpd 1-resistant HT1080 cells with Cpd 1-sensitive HT1080 cells, as shown in Table 1.

TABLE 1

| Gene | Genbank# | Expression | Fold Change |
|---|---|---|---|
| STOM | M81635 | Ubiquitous membrane protein deficient in high Na+, low K+ stomatocytic erythrocytes | 12.30 |
| CDA | NM_001785 | Cytidine deaminase | 11.15 |
| F8A | NM_012151 | Coagulation factor VIII-associated (intronic transcript) | 6.35 |
| STOM | AI537887 | tp32g06.x1 NCI_CGAP_Ut4 homo sapiens cDNA clone image: 2189530 (having a 3' amino acid terminus similar to the human gb: m81635 erythrocyte band 7 integral membrane protein human mRNA sequence) | 6.24 |
| KLHL1 | AF126749 | SCA8 mRNA, repeat region | 5.13 |
| EIF1AY | BC005248 | Eukaryotic translation initiation factor 1A, Y-linked | 0.07 |
| LOC81569 | BF594459 | Actin like protein | 0.12 |
| SORT1 | BE622952 | Sortilin 1 | 0.16 |
| FLJ21986 | BF724137 | Hypothetical protein FLJ21986 | 0.16 |
| MTMR1 | AI167164 | Myotubularin related protein 1 | 0.17 |

The gene expression analysis was performed with a cDNA microarray (provided by Affymatrix) using Cpd 1-resistant cells generated by culturing HT1080 cells in escalating concentrations of Cpd 1, then doubling Cpd 1 concentration weekly from 1 nM to 1000 nM and isolating total mRNA from the Cpd 1-resistant and wild-type HT1080 cells. Table 1 lists the genes with the greatest increase or decrease in expression in the Cpd 1-resistant HT1080 cell line, when compared to the parent HT1080 cells.

For example, cytidine deaminase (CDA) expression was increased 11-fold in Cpd 1-resistant HT1080 cells when compared with levels in the wild type HT1080 cells.

$^{15}$N-Glutamine Tracing Study

Figure 1A:
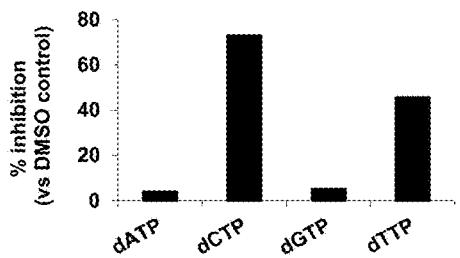
FIG. 1a shows Cpd 1 inhibition of total intracellular pyrimidine nucleotide production in HT1080 cells.
Figure 1B:
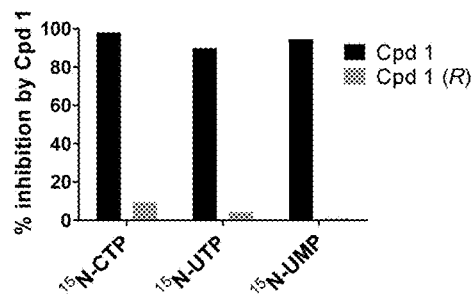
FIG. 1b shows the results of $^{15}$N-glutamine labeling studies comparing inhibition of synthesis of de novo pyrimidine nucleotide production (UMP, CTP and UTP) in HT1080 cells treated with the Cpd 1 active S-enantiomer and Cpd 1 (R), the inactive R-enantiomer, relative to vehicle control.

Since CDA is an enzyme in the pyrimidine nucleotide salvage pathway [5], the effect of Cpd 1 treatment on intracellular nucleotide levels was also evaluated using an $^{15}$N-glutamine tracing study. The study results demonstrate that, compared to $^{15}$N-glutamine (1 µM), Cpd 1 selectively decreased the total levels of deoxy-pyrimidine nucleotides (dCTP and dTTP) but not deoxy-purine nucleotides dATP and dGTP in HT1080 cells treated for 8 hours with Cpd 1 (100 nM) relative to vehicle control (0.5% DMSO), as determined by LC/MS (FIG. 1a). Therefore, Cpd 1 inhibits de novo pyrimidine synthesis, while its inactive R-enantiomer had no effect as determined by LCMS against $^{15}$N-labelled CTP, UTP and UMP (FIG. 1b). Further studies demonstrated that inhibition was dose-dependent and was measurable after only 30 minutes of treatment (data not shown).

Table 2 shows metabolism of $^{15}$N-glutamine in cells treated with Cpd 1 enantiomers (100 nm), brequinar (100 nm) (a known DHODH inhibitor) and pyrazofurin-monophosphate (MP) (100 nm) (a known UMPS inhibitor) or DMSO control for 8 hours in the presence of $^{15}$N-glutamine. The resulting metabolic activity is shown (µM), where BLDL indicates activity Below Detection Limits. The metabolism of $^{15}$N-glutamine in cells treated with Cpd 1 was similar to that in cells treated with brequinar [6], in contrast to the UMP synthase (UMPS) inhibitor pyrazofurin-monophosphate [7], which increased $^{15}$N-orotate levels by almost 160 fold.

TABLE 2

| Treatment | $^{15}$N-DHO (μM) | $^{15}$N-Orotate (μM) | $^{15}$N-UMP (μM) |
|---|---|---|---|
| 0.5% DMSO | BLDL | 6.7 ± 0.3 | 1.4 ± 0.4 |
| Cpd 1 (R) | BLDL | 4.4 ± 0.4 | 0.7 ± 0.2 |
| Cpd 1 | 18.1 ± 5.5 | 44.8 ± 6.1 | BLDL |
| Brequinar | 11.9 ± 3.7 | 50.1 ± 3.1 | BLDL |
| Pyrazofurin-MP | 1.3 ± 1.1 | 974 ± 175 | BLDL |

Comparative Inhibition of De Novo Pyrimidine Nucleotide Synthesis

Figure 1C:
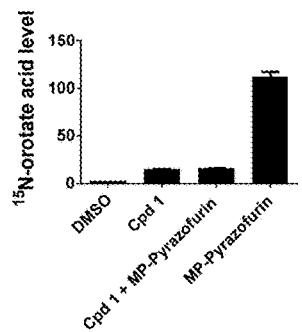
FIG. 1c shows that Cpd 1 acts upstream of UMPS, blocking UMPS inhibitor pyrazofurin induced increase of orotic acid in HT1080 cells.
Figure 1D:
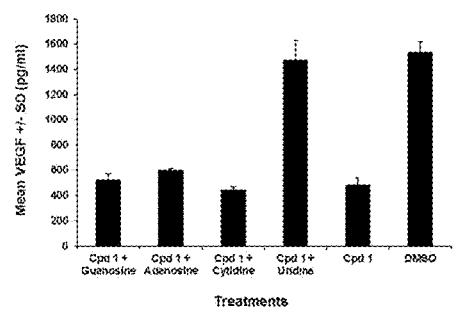
FIG. 1d shows Cpd 1 inhibited production of VEGFA protein (a DHODH surrogate for inhibition of DHODH function) in HT1080 cells was also blocked by addition of exogenous uridine rather than other nucleosides, including adenosine, cytidine and guanosine.
Figure 1E:
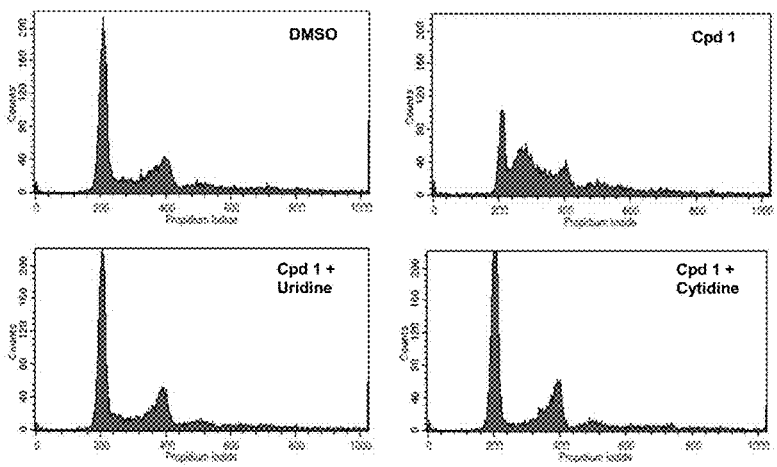
FIG. 1e shows that S-phase cell cycle arrest induced by Cpd 1 was blocked by addition of exogenous uridine or cytidine.

In another study, treatment with pyrazofurin-MP resulted in a greater than 40-fold increase of $^{15}$N-orotate, the substrate of UMPS, compared with vehicle (0.5% DMSO) (FIG. 1c). However, co-treatment with Cpd 1 blocked the pyrazofurin-MP-induced increase of $^{15}$N-orotate, consistent with inhibition of DHODH function, indicating that Cpd 1 acts upstream of UMPS. Having thus shown that Cpd 1 inhibits de novo pyrimidine nucleotide synthesis, subsequent nucleoside rescue studies using inhibition of VEGF protein production as a surrogate for inhibition of DHODH function demonstrated that the addition of uridine to the culture medium blocked Cpd 1 inhibition of VEGFA protein production (FIG. 1d). In contrast, adenosine, cytidine and guanosine did not have a similar effect. Moreover, Cpd 1 induced S phase cell cycle delay in HT1080 cells was prevented by the addition of the pyrimidine nucleosides uridine or cytidine (FIG. 1e), whereas addition of the purine nucleosides adenosine or guanosine had no effect (data not shown).

Comparative DHODH Binding

Figure 2A:
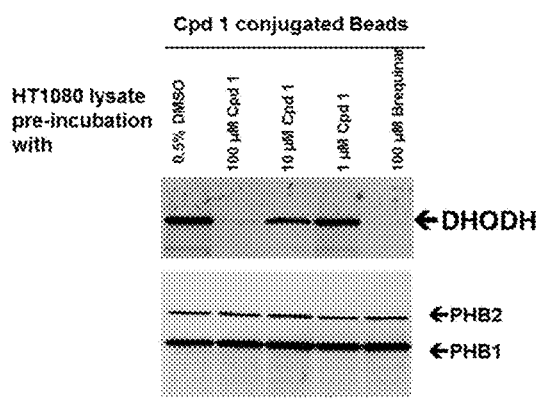
FIG. 2a shows free Cpd 1 and brequinar selectively "Competing On" with DHODH binding to the Cpd 1-beads by Western blot.
Figure 2B:
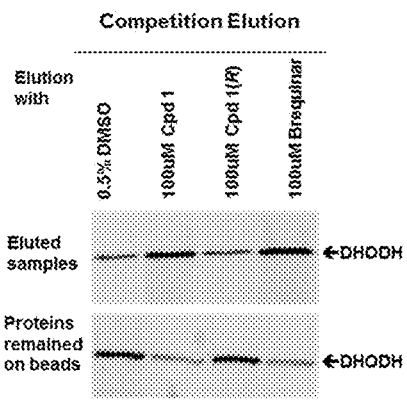
FIG. 2b shows elution of DHODH from selective "Competing Off" by free Cpd 1 and brequinar.
Figure 2C:
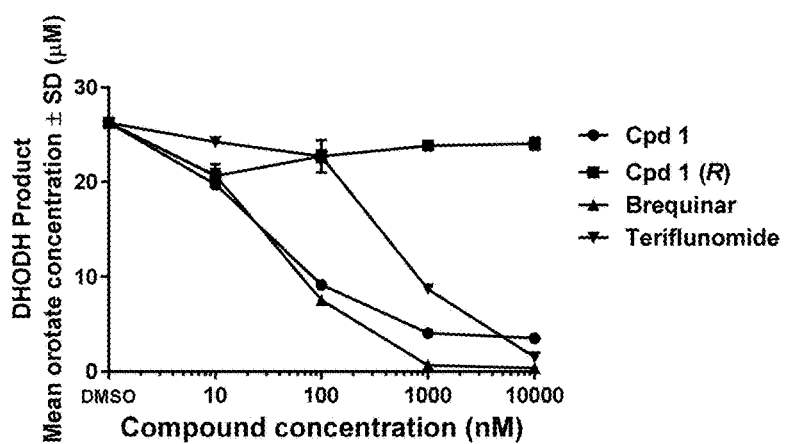
FIG. 2c compares the effect of Cpd 1 on the activity of isolated mitochondrial DHODH with the known DHODH inhibitors brequinar and teriflunomide using Cpd 1 (R), the inactive R-enantiomer as a negative control.
Figure 3A:
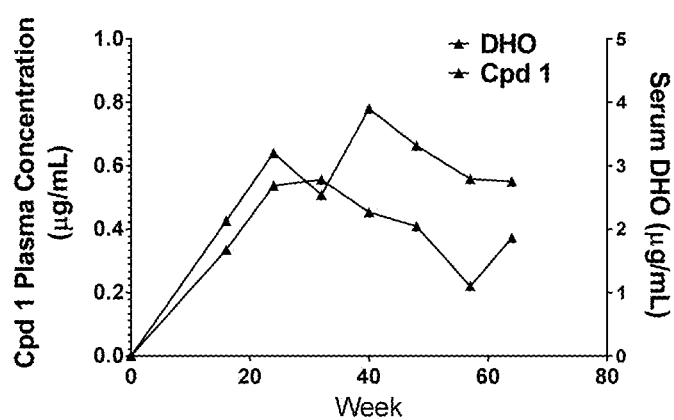
FIG. 3a shows serum levels of DHO correlated with Cpd 1 concentration in a NF2 clinical study subject.
Figure 3B:
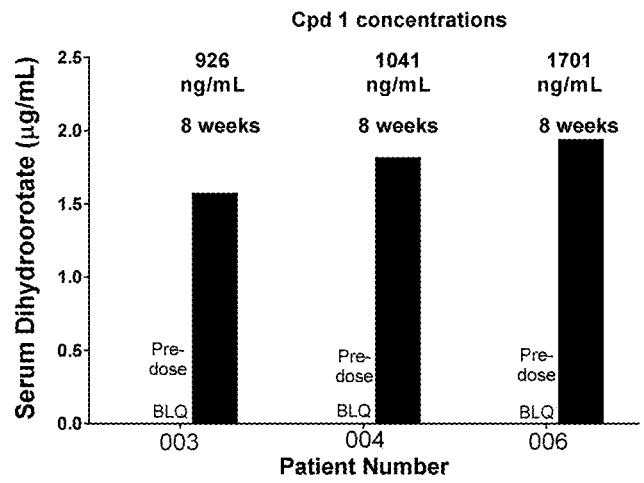
FIG. 3b shows Cpd 1 increased serum DHO in three additional NF2 subjects.

The binding partner of Cpd 1 was identified by pull down studies comparing the active Cpd 1 S-enantiomer and the inactive R-enantiomer linked to epoxy-activated Sepharose beads. Western blot analysis demonstrated that binding of DHODH to the Cpd 1-linked beads was inhibited by pre-incubation with either free Cpd 1 or brequinar (FIG. 2a). In contrast, binding to prohibitin, another mitochondrial protein, was not blocked by either free Cpd 1 or brequinar. Subsequent competitive elution studies demonstrated that DHODH was selectively eluted from the Cpd 1 beads by the free Cpd 1 S-enantiomer or brequinar, but not by the inactive R-enantiomer or the DMSO control (FIG. 2b). These findings demonstrate that Cpd 1 specifically binds DHODH. Computer modelling using the available crystal structure of the human DHODH protein [8] shows that Cpd 1 and brequinar analog C44 bind to the same pocket with similar docking scores [9,10] of 9.55 for C44 compared to 9.27 for Cpd 1, consistent with pull down studies demonstrating DHODH binding competition between brequinar and Cpd 1. When purified mitochondria were used as the source of DHODH, treatment with Cpd 1 inhibited DHODH activity more potently than did teriflunomide and with similar potency as brequinar (orotate production was measured by LC-MS/MS after 30 minutes of treatment, FIG. 2c). These data indicate that Cpd 1 inhibits de novo pyrimidine nucleotide synthesis via directly targeting DHODH.

Tumor Cell Line Panel Analysis

Figure 4A:
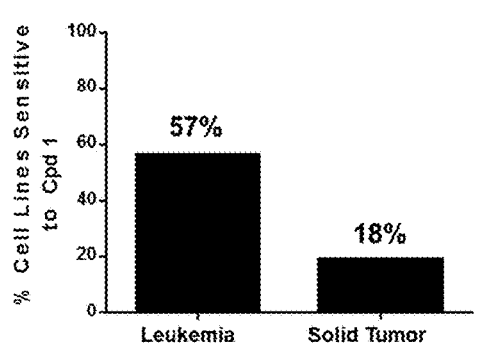
Figure 5A:
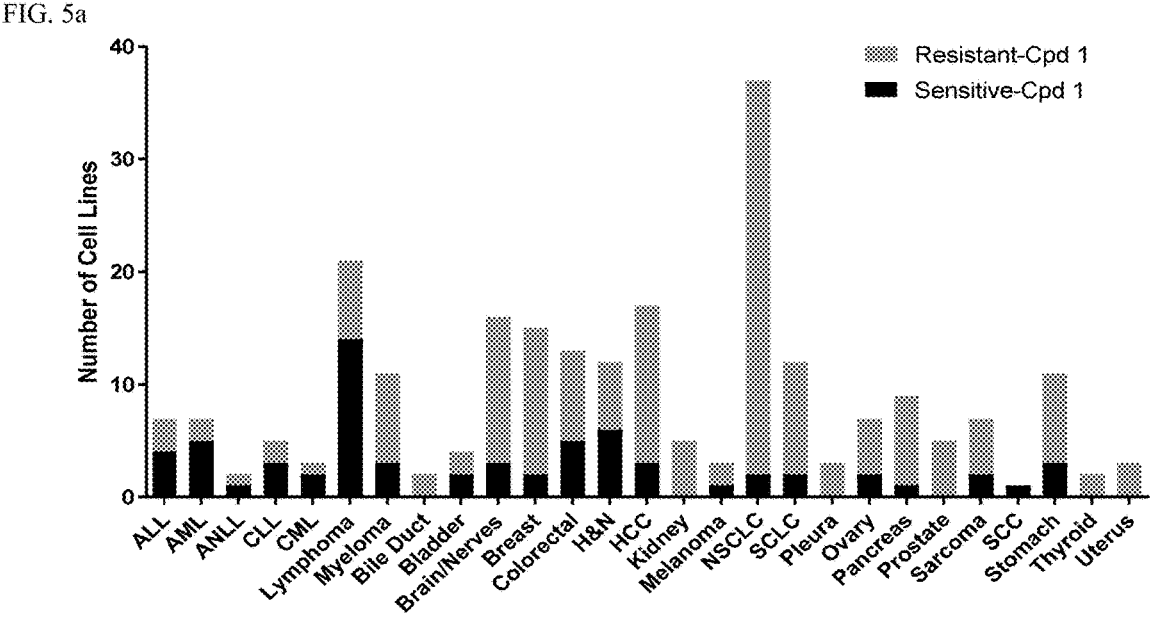
FIG. 5a shows sensitivity to Cpd 1 for a panel of 240 cell lines having various tissue origins.

Since pyrimidine nucleotides can be synthesized by either or both the de novo or the salvage pathway [11], to determine whether some cancer cell lines were insensitive to Cpd 1 due to increased pyrimidine nucleotide salvage activity, thus affecting the selective use of Cpd 1 to certain cancer types, the $IC_{50}$ (concentration that inhibits cell proliferation by 50%) of Cpd 1 was determined against a panel of 240 tumor cell lines. After a 3-day incubation period, the results shown in FIG. 5a indicate that Cpd 1 is an active inhibitor of DHODH function in certain hematologic cancers; where, ALL: acute lymphoblastic leukemia; AML: acute myeloid leukemia; ANLL: acute nonlymphocytic leukemia; CLL: chronic lymphocytic leukemia; CML: chronic myeloid leukemia; H&N: head and neck, HCC: hepatocellular carcinoma; NSCLC: non-small cell lung cancer; SCLC: small cell lung cancer. In FIG. 5a, tumor cells having an $IC_{50}$≤2 μM were classified as a sensitive responder (68 lines) compared with those having an $IC_{50}$>2 μM, considered a resistant non-responder (172 lines). When grouped by hematopoietic cancer vs solid tumor, 57% (32/56) of hematopoietic lines were sensitive to Cpd 1, whereas only 18% (34/184) of the solid tumor lines were sensitive to Cpd 1 (FIG. 4a).

Gene expression of pyrimidine nucleotide synthesis enzymes in these 240 lines was also analyzed using published microarray data in the Cancer Cell Line Encyclopedia (CCLE) database [12]. Of the 240 cell lines, 232 cell lines were found in the CCLE database, including 54 hematopoietic and 178 solid tumor cell lines.

Table 3 compares average expression of certain genes: dihydroorotate dehydrogenase (DHODH), uridine monophosphate synthetase (UMPS), uridine phosphorylase 1 (UPP1), cytidine deaminase (CDA), uridine-cytidine kinase 1 (UCK1), uridine-cytidine kinase 1-like 1 (UCKL1), uridine phosphorylase 2 (UPP2), uridine-cytidine kinase 2 (UCK2), cystolic cytidine monophosphate (UMP-CMP) kinase 1 (CMPK1), providing results for average expression in hematopoietic cancer lines (Hemat$^{Avg}$), solid tumor lines (Solid$^{Avg}$), and standard deviation in hematopoietic cancer lines (Hemat$^{SD}$), solid tumor lines (Solid$^{SD}$) and differential expression in hematopoietic tumor vs. solid tumor (ΔH-S) with t-test p-values comparing hematopoietic cancer (n=54) with solid tumors (n=178).

Figure 4B:
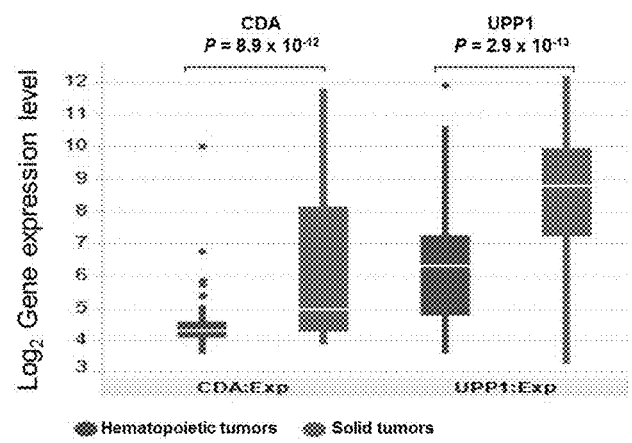
FIG. 4b provides box-plot microarray loge expression levels for CDA and UPP1, two pyrimidine salvage enzymes for producing uridine from cytidine and uracil, respectively.

As shown in Table 3, two salvage enzymes, CDA and UPP1 for converting cytidine and uracil to uridine, respectively, had lower expression (3.2-fold for CDA and 4.6-fold for UPP1) (where fold reduction is based on the Loge value of ΔH-S) in the hematopoietic cancer lines than in the solid tumor lines (see also FIG. 4b).

TABLE 3

| Gene | Hemat$^{Avg}$ | Solid$^{Avg}$ | Hemat$^{SD}$ | Solid$^{SD}$ | Δ H – S | p-value |
|---|---|---|---|---|---|---|
| DHODH[1] | 6.5 | 6.1 | 0.5 | 0.7 | 0.5 | 1 |
| UPMS[1] | 6.6 | 6.5 | 0.3 | 0.4 | 0.0 | 1 |
| UPP1[2] | 6.3 | 8.5 | 1.8 | 2.0 | −2.2 | 8.9E−12 |
| CDA[2] | 4.5 | 6.2 | 1.0 | 2.4 | −1.7 | 2.9E−12 |
| UCK1[2] | 6.8 | 7.0 | 0.4 | 0.5 | −0.2 | 0.0006 |
| UCKL1[2] | 7.7 | 7.7 | 0.4 | 0.6 | 0.0 | 0.39 |
| UPP2[2] | 3.8 | 3.7 | 0.2 | 0.1 | 0.1 | 1 |

TABLE 3-continued

| Gene | Hemat$^{Avg}$ | Solid$^{Avg}$ | Hemat$^{SD}$ | Solid$^{SD}$ | Δ H − S | p-value |
|---|---|---|---|---|---|---|
| UCK2[2] | 9.0 | 8.8 | 0.6 | 0.6 | 0.3 | 1 |
| CMPK1[2] | 10.9 | 10.4 | 0.5 | 0.6 | 0.6 | 1 |

Salvage and De Novo Pathway Panel

Figure 4C:
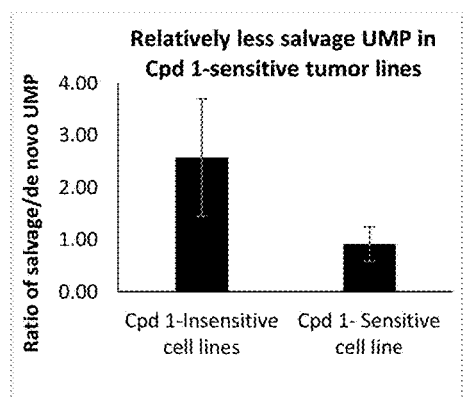
FIG. 4c compares relative UMP production from the salvage pathway in Cpd 1 sensitive and insensitive cell lines.

LC-MS/MS analysis of UMP pools from salvage and de novo pathways in a panel of tumor cell lines was performed, where four sensitive cell lines (HeLa, HT1080, A549 and K562) and four insensitive lines (U87MG, MCF7, PC3 and Huh7) were cultured in the presence of $^{15}$N-glutamine for 8 hours and unlabeled and $^{15}$N-labeled UMP in the cell lysates were measured by LC-MS/MS. In general, Cpd 1 sensitive cells have less salvage UMP production relative to de novo UMP production when compared to the insensitive tumor cells (FIG. 4c). These cumulative data suggest that a hematologic cancer having lower uridine salvage activity enhances the therapeutic effect of Cpd 1.

DHODH Inhibitor Leukemia Cell Line Comparison

Figure 4D:
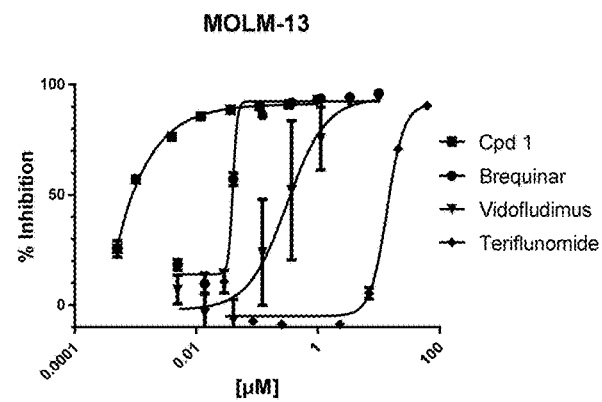
FIG. 4d compares other known DHODH inhibitors with Cpd 1 for inhibiting proliferation of MOLM-13 AML cells.
Figure 4E:
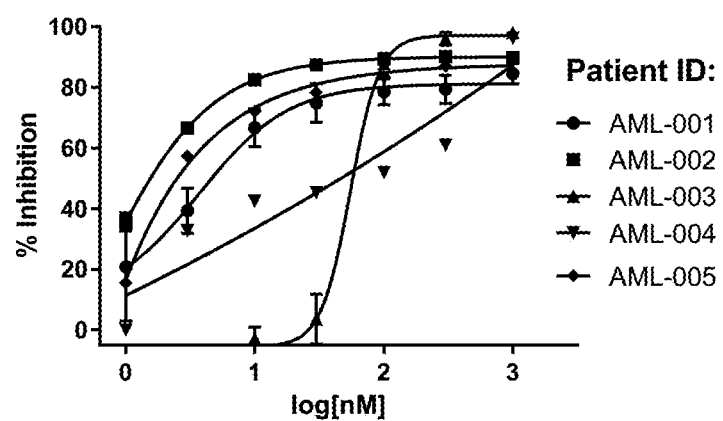
FIG. 4e shows inhibition of in vitro proliferation in various subject derived AML cell lines treated with Cpd 1.

After confirming in vivo DHODH inhibition activity in solid tumor clinical studies and in vitro activity in leukemia cell lines, the potency of Cpd 1 was also compared with that of several well-known DHODH inhibitors [6; 13; 14] in leukemia cells. Cpd 1 was the most potent inhibitor with an IC$_{50}$ of about 1 nM, having 10-1000-fold greater potency than well-known inhibitors of DHODH function, such as brequinar, vidofludimus or teriflunomide (FIG. 4d). Acute myeloid leukemia (AML) subject-derived cells were treated for 72 hours with Cpd 1, teriflunomide and brequinar, where proliferation was measured with Celltiter Glo (Promega), demonstrating inhibition of proliferation in all five AML subject derived cell lines tested (FIG. 4e). Unlike teriflunomide and brequinar, Cpd 1 did not show myeloid suppression in subjects with solid tumors [24].

Figure 5B:
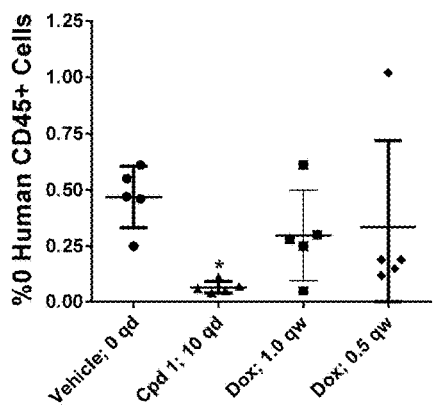
FIG. 5b shows effect of Cpd 1 treatment on the number of human leukemia cells in blood from mice in a systemic leukemia lethality model.
Figure 5C:
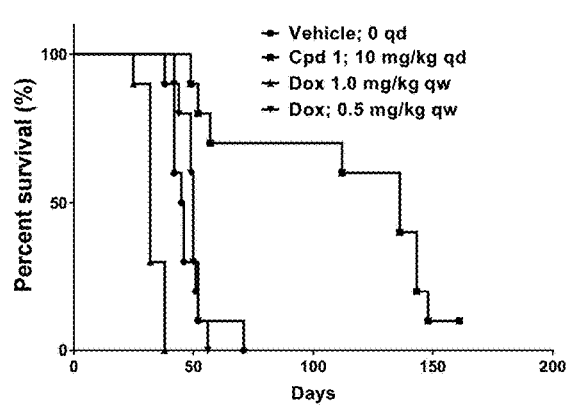
FIG. 5c shows survival of mice in the systemic leukemia lethality model.

MOLT-4 Human Acute Lymphoblastic Leukemia Lethality Model After confirming in vitro activity in leukemia cells, the efficacy of Cpd 1 in two mouse models of leukemia was assessed. In the MOLT-4 human acute lymphoblastic leukemia (ALL) lethality model, NOD/SCID mice were injected intravenously (IV) with MOLT-4 cells (CD45+) then treated with Cpd 1 (10 mg/kg, qd) or doxorubicin (0.5 mg/kg or 1 mg/kg IP once per week) initiated 7 days after tumor inoculation. Cpd 1 treatment significantly reduced the number of circulating MOLT-4 cells in mice compared to doxorubicin (FIG. 5b). Doxorubicin was tested at the highest dose tolerated by NOD/SCID mice. Vehicle-dosed mice had a median survival time (MST) of 46 days and did not survive beyond 71 days. Treatment with doxorubicin did not prolong survival time (FIG. 6a). In contrast, the MST for the Cpd 1 treated mice was 136 days (p<0.05, one way ANOVA, multiple comparisons vs vehicle).

MOLM-13 Human Acute Myeloid Leukemia Model

Figure 6:
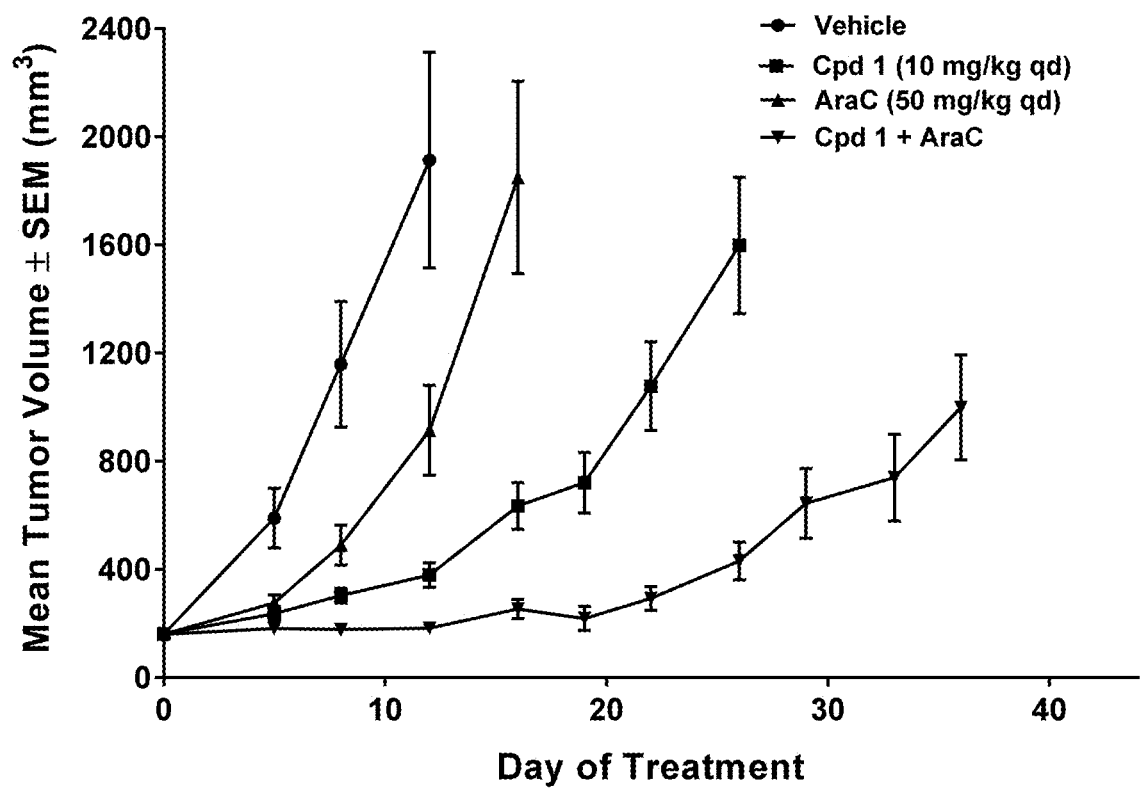
FIG. 6 shows effect on tumor growth progress in a MOLM-13 acute myeloid leukemia (AML) model after treatment with vehicle, Cpd 1, cytarabine (AraC), or a combination of Cpd 1 and AraC over the study period.

In another xenograft study, MOLM-13 AML cells were injected into the flank of nude mice to generate a solid tumor then mice were treated with vehicle, Cpd 1, cytarabine (AraC), a deoxycytidine analog used as standard chemotherapy to treat AML [15], or a combination of Cpd 1 and AraC (FIG. 6). Cpd 1 treatment alone resulted in significant tumor growth delay when compared with vehicle or AraC treatment; the median time to reach a tumor volume of 1000 mm$^3$ was 23 days for Cpd 1 vs 7 and 13 days for vehicle and AraC, respectively. The combination of Cpd 1 with AraC further delayed tumor growth for 39 days. The increased activity of the combination of AraC with Cpd 1 may reflect a more efficient incorporation of AraC into DNA due to a reduction in the levels of competing endogenous pyrimidine nucleotides.

These results suggest that Cpd 1 potently inhibits leukemia cell proliferation dependent on de novo pyrimidine nucleotide synthesis by selectively affecting DHODH function.

Definitions

As used herein, the term "about" means a range around a given value wherein the resulting value is substantially the same as the expressly recited value. In one aspect, "about" means within 25% of a given value or range. For example, the phrase "about 70% by weight" comprises at least all values from 52% to 88% by weight. In another aspect, the term "about" means within 10% of a given value or range. For example, the phrase "about 70% by weight" comprises at least all values from 63% to 77% by weight. In another aspect, the term "about" means within 7% of a given value or range. For example, the phrase "about 70% by weight" comprises at least all values from 65% to 75% by weight.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

As used herein, the terms "therapies" and "therapy" can refer to any protocol(s), method(s), compositions, formulations, and/or agent(s) that can be used in the prevention, treatment, management, or amelioration of a condition or disorder or one or more symptoms thereof (e.g., hematologic cancer or one or more symptoms or one or more conditions associated therewith).

In certain aspects, the terms "therapies" and "therapy" refer to drug therapy such as chemotherapy, adjuvant therapy, radiation, surgery, biological therapy, supportive therapy, antiviral therapy and/or other therapies useful in treatment, management, prevention, or amelioration of a condition or disorder or one or more symptoms thereof (e.g., hematologic cancer or one or more symptoms or one or more conditions associated therewith). In certain aspects, the term "therapy" refers to a therapy other than Cpd 1 or a pharmaceutical composition thereof. In specific aspects, an "additional therapy" and "additional therapies" refer to a therapy other than a treatment using Cpd 1 or a pharmaceutical composition thereof. In a specific aspect, a therapy includes the use of Cpd 1 as an adjuvant therapy. For example, using Cpd 1 in conjunction with a drug therapy such as chemotherapy, biological therapy, surgery, supportive therapy, antiviral therapy and/or other therapies useful in treatment, management, prevention, or amelioration of a condition or disorder or one or more symptoms thereof (e.g., hematologic cancer or one or more symptoms or one or more conditions associated therewith).

As used herein, the term "human infant" refers to a newborn to 1 year old year human.

As used herein, the term "human toddler" refers to a human that is 1 year to 3 years old.

As used herein, the term "human child" refers to a human that is 1 year to 18 years old.

As used herein, the term "human adult" refers to a human that is 18 years or older.

As used herein, the term "middle-aged human" refers to a human between the ages of 30 and 64.

As used herein, the term "elderly human" refers to a human 65 years or older.

As used herein, the term "subject" refers to an individual being administered a therapy as described herein. In a specific aspect, the individual is a human.

As used herein, the term "effective amount" in the context of administering Cpd 1 to a subject having a hematologic cancer refers to the dose of Cpd 1 that results in a beneficial or therapeutic effect. In specific aspects, an "effective amount" of Cpd 1 refers to an amount of Cpd 1 which is sufficient to achieve at least one, two, three, four or more of the following beneficial or therapeutic effects: (i) inhibition of a hematologic cancer; (ii) regression of the hematologic cancer; (iii) eradication, removal, or complete remission of the hematologic cancer; (iv) prevention of the development or onset of one or more symptoms associated with the hematologic cancer; (v) reduction or amelioration of the severity of one or more symptoms associated with the hematologic cancer; (vi) the reduction in the number of one or more symptoms associated with cancer; (vii) amelioration of the severity of one or more symptoms associated with the hematologic cancer; (viii) reduction in the duration of one or more symptoms associated with the hematologic cancer; (ix) prevention in the recurrence of proliferation or one or more symptoms associated with the hematologic cancer; (x) a reduction in mortality; (xi) an increase in survival rate of subjects; (xii) an increase in relapse free survival; (xiii) an increase in the number of hematologic cancer subjects in remission; (xiv) reduction in hospitalization of a subject; (xv) reduction in hospitalization length; (xvi) a decrease in hospitalization rate; (xvii) an increase in the survival of a subject; (xviii) an increase in symptom-free survival of cancer subjects; (xix) an increase in the length of a period of remission of a hematologic cancer in a subject; (xx) improvement in quality of life (QOL) as assessed by methods well known in the art, e.g., QOL questionnaires and the like; (xxi) a reduction in proliferation before treatment with another chemotherapeutic agent; (xxii) a reduction in proliferation before treatment with radiation; (xxiii) a reduction in proliferation before treatment with surgery; (xxiv) enhancement of or improvement of the therapeutic effect of another therapy; (xxv) an additive antiproliferative effect in combination with another therapy; (xxvi) a synergistic antiproliferative effect in combination with another therapy; (xxvii) a decrease in the concentration of plasma DHODH of a subject having a hematologic cancer; (xxviii) a decrease in circulating proliferative cells in the plasma of a subject having a hematologic cancer; (xxix) an alteration (e.g, a decrease) in a biomarker for a hematologic cancer; (xxx) reduction of the concentration of DHODH in a biological specimen (e.g., plasma, serum, cerebral spinal fluid, urine, or any other biofluids) from a subject having a hematologic cancer; (xxxi) a decrease in the concentration of DHODH in a biological specimen (e.g., the plasma, serum, urine or cerebrospinal fluid (CSF)) from a subject having a hematologic cancer; (xxxii) reduction of the concentration of one or more biomarkers in a biological specimen (e.g., plasma, serum, cerebral spinal fluid, urine, or any other biofluids) from a subject having a hematologic cancer; (xxxiii) proliferative cell count is maintained after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan; (xxxiv) white cell count is maintained after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan; (xxxv) proliferative cell count does not increase or increases by less than expected after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan; (xxxvi) white cell count does not increase or increases by less than expected after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan; (xxxvii) proliferative cell count is decreased after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan; or, (xxxviii) white cell count is decreased after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography scan.

As used herein, the term "in a 24 hour period" refers to a period of time over which a condition is maintained; for example, the effective amount of Cpd 1 is identified when the mean plasma concentration of Cpd 1 is achieved and maintained for a plurality of 24 hour periods. In other words, the mean plasma concentration of Cpd 1 may be reached in a suitable time, which may be more or less than 24 hours.

As used herein, the term "a therapy as described herein" refers to a method of use for Cpd 1 or a form or pharmaceutical composition thereof as an inhibitor of DHODH function in treating or ameliorating a hematological cancer in a subject in need thereof comprising, administering to the subject an effective amount of Cpd 1. In one aspect, the hematological cancer is a leukemia. In another aspect, the leukemia is an acute or chronic form of leukemia. In another aspect, the leukemia is characterized by reduced expression of uridine salvage enzymes and dependence on de novo pyrimidine nucleotide synthesis. In another aspect of the therapy described herein, the method of use for Cpd 1 or a form or pharmaceutical composition comprises a combination with other chemotherapeutic agents having synergistic antiproliferative activity. In one aspect, the other chemotherapeutic agent inhibits DHODH functional activity. In another aspect, the other chemotherapeutic agent inhibits IDH expression.

As used herein, the term "pharmaceutically acceptable salt(s)" refers to a salt prepared from a pharmaceutically acceptable non-toxic acid or base including an inorganic acid and base and an organic acid and base; see, for example, *Remington's Pharmaceutical Sciences*, 18th eds., Mack Publishing, Easton Pa. (1990) or *Remington: The Science and Practice of Pharmacy*, 19$^{th}$ eds., Mack Publishing, Easton Pa. (1995).

As used herein, the term "Cpd 1" generally refers to a 4-chlorophenyl (S)-6-chloro-1-(4-methoxyphenyl)-1,3,4,9-tetrahydro-2H-pyrido[3,4-b]indole-2-carboxylate compound and pharmaceutically acceptable salts thereof. "Cpd 1" may be a substantially pure (e.g., about 90%, about 95%, about 98%, about 99%, or about 99.9% pure) single stereoisomer or a mixture of two or more stereoisomers. In various aspects, the term "Cpd 1" refers to Compound #10 disclosed in International Publication Nos. WO2005/089764, WO2006/113703, WO2008/127715 and WO2008/127714, all of which are incorporated by reference herein in their entirety.

Method of Use

As demonstrated herein, Cpd 1 inhibits de novo pyrimidine synthesis by targeting inhibition of DHODH function, a rate-limiting enzyme catalyzing oxidation of DHO to orotate [1]. An inhibitor of DHODH function and other therapeutics affecting DHODH alter the nucleotide balance to induce cell-cycle arrest [17]. Exogenously added uridine prevents both the inhibition of DHODH enzyme function and cell cycle arrest mediated by Cpd 1, while exogenously added cytidine only rescues the cell cycle arrest, suggesting that inhibition of DHODH function and cell cycle arrest may be coincidental.

Low pyrimidine pool levels may affect certain translation factor(s) or mechanisms required for the non-canonical protein synthesis of stress-regulated mRNAs. Treatment of Cpd 1-resistant HT1080 cells with Cpd 1 showed that eIF1AY gene expression decreased over 90% when compared with wild type HT1080 cells (Table 1). EIF1A is an isoform that controls translation start codon recognition [18]. Low uridine levels may also affect the mRNA substrate directly: depletion of pyrimidine nucleotides in cancer cells can cause a starvation-like stress response leading to changes in methylation and pseudouridylation of mRNA modifications [19]. Although Cpd 1 demonstrates less inhibition of DHODH functional activity in purified rhDHODH enzymatic assays, Cpd 1 is a more potent inhibitor of DHODH function in hematologic cancer cells than other well-known DHODH inhibitors. Without being limited by theory, this apparent discrepancy is likely due to the presence of the cell membrane lipid bilayer which may facilitate the entry of the hydrophobic Cpd 1 into the binding pocket of the DHODH enzyme [25].

Figure 7:
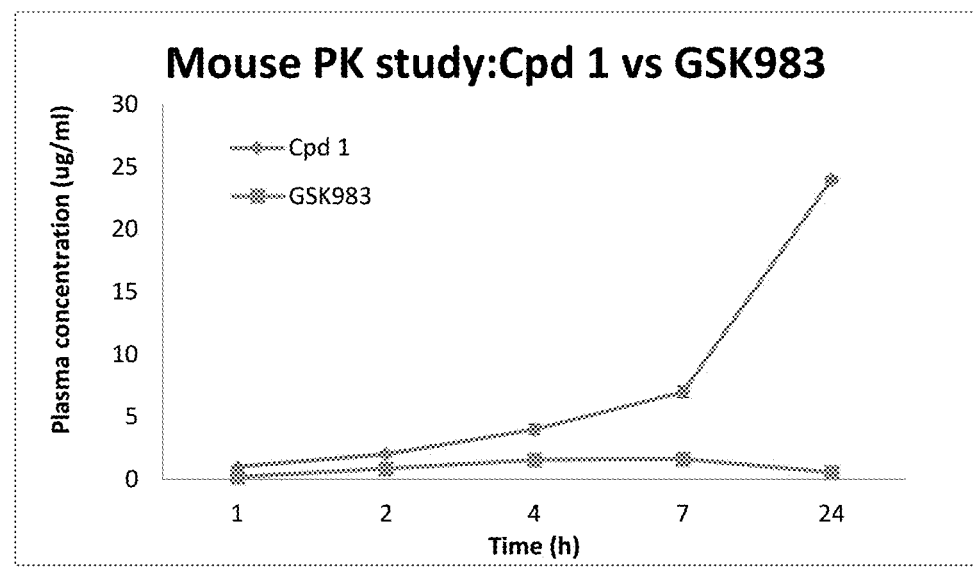
FIG. 7 compares bioavailability of Cpd 1 and GSK983 orally administered to mice.
Figure 8:
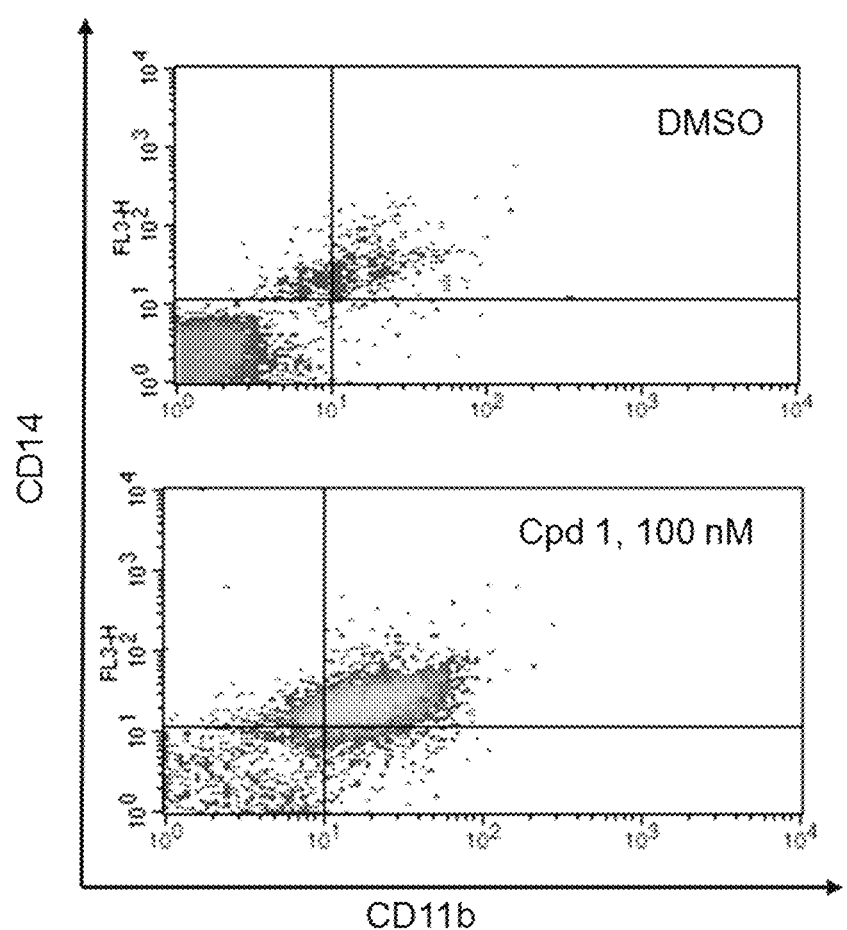
FIG. 8 MOML-13 AML cells were treated with Cpd 1 (100 nM) or DMSO control for 72 hours, then stained with anti-CD14 and CD11b antibodies.

Another potent hDHODH inhibitor brequinar was tested in the 1990s in clinical trials for solid tumors, but was associated with myeloid suppression and has a limited therapeutic window [20; 21]. The side-effects associated with these DHODH inhibitors are believed to be due to off-target activities such as kinase inhibition [21; 22]. Cpd 1 avoids off-target activities having demonstrated lack of inhibition of kinase enzyme activity in a panel of biologically important human kinases. The antiviral compound GSK983 was recently reported as a DHODH inhibitor [23]. When compared with Cpd 1 at a dose of 10 mg/kg, GSK983 demonstrated a lower plasma concentration as determined by HPLC-MS/MS (FIG. 7). In contrast, Cpd 1 (100 nM) induces in vitro differentiation of MOML-13 acute myeloid leukemia (AML) cells relative to DMSO control after 72 hours treatment when stained with anti-CD14 and CD11b antibodies (BD Bioscience). FACS analysis was done on FACSCalibur (FIG. 8).

There are no DHODH inhibitors known or approved for use in treating hematologic cancers. The broad activity of Cpd 1 across various leukemia/lymphoma cells demonstrated herein suggest that de novo pyrimidine synthesis is required in proliferation of leukemia cells. These results are consistent with a recent report on DHODH inhibitors [26]. Accordingly, potent and selective activity, favorable pharmaceutical properties and extensive clinical experience suggest that Cpd 1 is a useful agent for treatment of leukemia.

In one aspect, methods for inhibiting or reducing DHODH function in a proliferating cell or cell line are described herein.

In another aspect, a method for inhibiting or reducing DHODH function in a proliferating cell or cell line comprises, contacting Cpd 1 or a composition thereof with a proliferating cell or cell line, which proliferating cell or cell line may be naïve or has been shown to be affected by the inhibition or a reduction in DHODH function.

In another aspect, non-limiting examples of such cells or cell lines are selected from HL-60, HeLa, HT1080, HCT116, HEK293, NCI H460, U-87MG, ASPC-1, PL-45, HPAF-2, PC-3, MDA-MB-231, MDA-MB-468, A431, SNU-1, AGS, Kato III, A549, Calu-6, A375, SY5Y, SKOV3, Capan-1, sNF96.2, TIVE-L1, TIVE-L2, LNCaP cells and the like. In a more specific aspect, the cell or cell line may be a hematologic cancer cell.

In one aspect, a method for inhibiting or reducing DHODH function in a subject having a hematologic cancer comprises, administering Cpd 1 or a composition thereof to the subject as described herein.

In a specific aspect, the subject is diagnosed with a hematologic cancer capable of being treated by inhibiting or reducing DHODH function.

In a specific aspect, the hematologic cancer capable of being treated by inhibiting or reducing DHODH function demonstrates, prior to administration of Cpd 1, the reduced expression of uridine salvage enzymes, wherein the low expression of uridine salvage enzymes and dependence on de novo pyrimidine nucleotide synthesis in the subject or in a biological sample taken from the subject indicates that the hematological cancer is amendable to treatment with Cpd 1.

In a specific aspect, a method for inhibiting or reducing DHODH function as described herein inhibits or reduces DHODH function by about 5%, 10%, 15%, 20%, 25%, 30%, 35%, 40%, 45%, 50%, 55%, 60%, 65%, 80%, 85%, 90%, 95%, or 100% relative to DHODH function prior to administration of Cpd 1 to the subject, as assessed by methods well known in the art.

In a specific aspect, a method for inhibiting or reducing DHODH function as described herein inhibits or reduces DHODH function in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to DHODH function prior to administration of Cpd 1 to the subject, as assessed by methods well known in the art.

In a specific aspect, a method for inhibiting or reducing DHODH function as described herein inhibits proliferation or reduces an in vitro or in vivo proliferating cell or cell line population by about 5%, 10%, 15%, 20%, 25%, 30%, 35%, 40%, 45%, 50%, 55%, 60%, 65%, 80%, 85%, 90%, 95%, or 100%, relative to the in vitro or in vivo proliferating cell or cell line population prior to administration of Cpd 1 to the subject, as assessed by methods well known in the art.

In a specific aspect, a method for inhibiting or reducing DHODH function as described herein inhibits proliferation or reduces an in vitro or in vivo proliferating cell or cell line population in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the in vitro or in vivo proliferating cell or cell line population prior to administration of Cpd 1 to the subject, as assessed by methods well known in the art.

In various aspects, a method for inhibiting or reducing DHODH function as described herein reduces the concentration of DHODH in a subject as assessed by methods well known in the art, e.g., ELISA.

In one aspect, a method for preventing, treating or ameliorating a hematologic cancer in a subject in need thereof comprises, administering an amount of Cpd 1 effective to inhibit or reduce DHODH function in the subject is described herein.

In a specific aspect, a method for preventing, treating or ameliorating a hematologic cancer in a subject in need thereof as described herein inhibits or reduces DHODH function by about 5%, 10%, 15%, 20%, 25%, 30%, 35%, 40%, 45%, 50%, 55%, 60%, 65%, 80%, 85%, 90%, 95%, or 100% relative to DHODH function of Cpd 1 to the subject, as assessed by methods well known in the art.

In a specific aspect, a method for preventing, treating or ameliorating a hematologic cancer in a subject in need thereof as described herein inhibits or reduces DHODH function in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to DHODH function prior to administration of Cpd 1 to the subject, as assessed by methods well known in the art.

In various aspects, a method for preventing, treating or ameliorating a hematologic cancer in a subject in need thereof as described herein reduces the concentration of DHODH in a subject as assessed by methods well known in the art, e.g., ELISA.

In one aspect, a method for preventing, treating or ameliorating a hematologic cancer in a subject in need thereof comprises, administering an amount of Cpd 1 effective to inhibit proliferation or reduce an in vitro or in vivo proliferating cell or cell line population in the subject is described herein.

In a specific aspect, a method for preventing, treating or ameliorating a hematologic cancer in a subject in need thereof as described herein inhibits proliferation or reduces an in vitro or in vivo proliferating cell or cell line population in the subject by about 5%, 10%, 15%, 20%, 25%, 30%, 35%, 40%, 45%, 50%, 55%, 60%, 65%, 80%, 85%, 90%, 95%, or 100% relative to proliferation or in vitro or in vivo proliferating cell or cell line population in the subject prior to administration of Cpd 1 to the subject, as assessed by methods well known in the art.

In a specific aspect, a method for preventing, treating or ameliorating a hematologic cancer in a subject in need thereof as described herein inhibits proliferation or reduces an in vitro or in vivo proliferating cell or cell line population in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to proliferation or in vitro or in vivo proliferating cell or cell line population in the subject prior to administration of Cpd 1 to the subject, as assessed by methods well known in the art.

In various aspects, a method for preventing, treating or ameliorating a hematologic cancer in a subject in need thereof as described herein inhibits proliferation or reduces an in vitro or in vivo proliferating cell or cell line population in a subject as assessed by methods well known in the art, e.g., ELISA.

In one aspect, a method for preventing, treating or ameliorating a hematologic cancer in a subject in need thereof comprises, administering an amount of Cpd 1 effective to inhibit proliferation or reduce an in vitro or in vivo proliferating cell or cell line population in the subject in combination with another therapy (e.g., one or more additional therapies that do not comprise Cpd 1, or that comprise a different anti-proliferative agent) to a subject in need thereof is described herein.

Such methods may involve administering Cpd 1 prior to, concurrent with, or subsequent to administration of the additional therapy. In certain aspects, such methods have an additive or synergistic effect.

In a specific aspect, presented herein is a method for preventing, treating or ameliorating a hematologic cancer in a subject in need thereof comprising, administering to a subject in need thereof an effective amount of Cpd 1 and an effective amount of another therapy.

Specific examples of cancers that can be prevented, treated or ameliorated in accordance with the methods provided herein include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myclocytic (granulocytic) leukemia, chronic lymphocytic leukemia, hairy cell leukemia; polycythemia vera; plasma cell leukemia and MDS.

In certain aspects, cancers that can be prevented, treated or ameliorated in accordance with the methods provided herein are selected from acute myeloid leukemia, acute lymphocytic leukemia, and MDS.

In one aspect, presented herein is a method for preventing, treating or ameliorating a hematologic cancer, comprising: (a) administering to a subject in need thereof one or more doses of Cpd 1 or a pharmaceutical composition thereof; and (b) monitoring the concentration of certain biomarkers, before and/or after step (a).

In a specific aspect, the monitoring step (b) is carried out before and/or after a certain number of doses (e.g., 1, 2, 4, 6, 8, 10, 12, 14, 15, or 29 doses, or more doses; 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks) of administering Cpd 1 or a pharmaceutical composition thereof.

In a specific aspect, one or more of these monitoring parameters are detected prior to administration of Cpd 1 or pharmaceutical composition thereof to the subject.

In a specific aspect, a decrease in the proliferation of an in vitro or in vivo proliferating cell or cell line population following administration of Cpd 1 or a pharmaceutical composition thereof indicates that the course of treatment is effective for preventing, treating or ameliorating the hematologic cancer.

a specific aspect, a change in the proliferation of an in vitro or in vivo proliferating cell or cell line population following administration of Cpd 1 or a pharmaceutical composition thereof may indicate that the dosage, frequency and/or length of administration of Cpd 1 or a pharmaceutical composition thereof may be adjusted (e.g., increased, reduced or maintained).

In a specific aspect, the concentration of certain biomarkers in biological specimens of a subject is monitored before, during and/or after a course of treatment for a hematologic cancer involving the administration of Cpd 1 or a pharmaceutical composition thereof to the subject.

The dosage, frequency and/or length of administration of Cpd 1 or a pharmaceutical composition thereof to a subject might be modified as a result of the proliferation of an in vitro or in vivo proliferating cell or cell line population. Alternatively, the changes in these monitoring parameters (e.g., concentration of certain biomarkers) might indicate that the course of treatment involving the administration of the Cpd 1 or a pharmaceutical composition thereof is effective in preventing, treating or ameliorating the hematologic cancer.

The concentration of certain biomarkers in a subject may be detected by any technique known to one of skill in the art. In certain aspects, the method for detecting the concentration of certain biomarkers of a subject comprises obtaining a biological sample (e.g., tissue or fluid sample) from the subject and detecting the concentration of the biomarkers in the biological sample (e.g., from plasma, serum, cerebral spinal fluid, urine, or any other biofluids), that has been subjected to certain types of treatment (e.g., centrifugation), and detection by use of immunological techniques, such as ELISA.

In a specific aspect, an ELISA assay, as described herein, may be used to detect the concentration of the biomarkers in a biological sample (e.g., from plasma, serum, cerebral spinal fluid, urine, or any other biofluids) that has been subjected to certain types of treatment (e.g., centrifugation). Other techniques known in the art that may be used to detect the concentration of the biomarkers in a biological sample include multiplex or proteomic assays.

In specific aspects, the methods for preventing, treating or ameliorating a hematologic cancer provided herein alleviate or manage one, two or more symptoms associated with the hematologic cancer. Alleviating or managing one, two or more symptoms of the hematologic cancer may be used as a clinical endpoint for efficacy of Cpd 1 or a pharmaceutical composition thereof for preventing, treating or ameliorating the hematologic cancer. In some aspects, the methods for preventing, treating or ameliorating the hematologic cancer provided herein reduce the duration and/or severity of one or more symptoms associated with the hematologic cancer.

In some aspects, the methods for preventing, treating or ameliorating the hematologic cancer provided herein inhibit the onset, progression and/or recurrence of one or more symptoms associated with the hematologic cancer. In some aspects, the methods for treating the hematologic cancer provided herein reduce the number of symptoms associated with the hematologic cancer.

In one aspect, a method for preventing, treating or ameliorating a hematologic cancer in a subject in need thereof comprises, administering an amount of Cpd 1 or a pharmaceutical composition thereof effective to inhibit or reduce the function of DHODH and IDH in the subject is described herein.

In a specific aspect, the subject is diagnosed with a hematologic cancer capable of being treated by inhibiting or reducing the function of DHODH and IDH in the subject.

In a specific aspect, a method for preventing, treating or ameliorating a hematologic cancer in a subject in need thereof as described herein inhibits or reduces the function of DHODH and IDH in the subject by about 5%, 10%, 15%, 20%, 25%, 30%, 35%, 40%, 45%, 50%, 55%, 60%, 65%, 80%, 85%, 90%, 95%, or 100% relative to the function of DHODH and IDH prior to administration of Cpd 1 or a pharmaceutical composition thereof to the subject, as assessed by methods well known in the art.

In a specific aspect, a method for preventing, treating or ameliorating a hematologic cancer in a subject in need thereof as described herein inhibits or reduces the function of DHODH and IDH in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and IDH prior to administration of Cpd 1 or a pharmaceutical composition thereof, as assessed by methods well known in the art.

In various aspects, a method for preventing, treating or ameliorating a hematologic cancer in a subject in need thereof as described herein inhibits or reduces the function of DHODH and IDH in a subject as assessed by methods well known in the art, e.g., ELISA.

In one aspect, a method for preventing, treating or ameliorating a hematologic cancer in a subject in need thereof comprises, administering an amount of Cpd 1 or a pharmaceutical composition thereof effective to inhibit or reduce the function of DHODH and wild-type IDH or mutant IDH in the subject is described herein.

In another specific aspect, the subject is diagnosed with a hematologic cancer capable of being treated by inhibiting or reducing the function of DHODH and wild-type IDH or mutant IDH in the subject.

In a specific aspect, a method for preventing, treating or ameliorating a hematologic cancer in a subject in need thereof as described herein inhibits or reduces the function of DHODH and wild-type IDH or mutant IDH in the subject by about 5%, 10%, 15%, 20%, 25%, 30%, 35%, 40%, 45%, 50%, 55%, 60%, 65%, 80%, 85%, 90%, 95%, or 100% relative to the function of DHODH and wild-type IDH1, wild-type IDH2, mutant IDH1 or mutant IDH2 prior to administration of Cpd 1 or a pharmaceutical composition thereof, as assessed by methods well known in the art.

In a specific aspect, a method for preventing, treating or ameliorating a hematologic cancer in a subject in need thereof as described herein inhibits or reduces the function of DHODH and wild-type IDH or mutant IDH in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and wild-type IDH1, wild-type IDH2, mutant IDH1 or mutant IDH2 prior to administration of Cpd 1 or a pharmaceutical composition thereof, as assessed by methods well known in the art.

In various aspects, a method for preventing, treating or ameliorating a hematologic cancer in a subject in need thereof as described herein inhibits or reduces the function of DHODH and wild-type IDH or mutant IDH in a subject as assessed by methods well known in the art, e.g., ELISA.

In one aspect, a method for preventing, treating or ameliorating a hematologic cancer in a subject in need thereof comprises, administering an amount of Cpd 1 or a pharmaceutical composition thereof effective to inhibit or reduce the function of DHODH and wild-type IDH1, wild-type IDH2, mutant IDH1 or mutant IDH2 in the subject is described herein.

In a more specific aspect, the subject is diagnosed with a hematologic cancer capable of being treated by inhibiting or reducing the function of DHODH and wild-type IDH1, wild-type IDH2, mutant IDH1 or mutant IDH2 in the subject.

In a specific aspect, a method for preventing, treating or ameliorating a hematologic cancer in a subject in need thereof as described herein inhibits or reduces the function of DHODH and wild-type IDH1, wild-type IDH2, mutant IDH1 or mutant IDH2 in the subject by about 5%, 10%, 15%, 20%, 25%, 30%, 35%, 40%, 45%, 50%, 55%, 60%, 65%, 80%, 85%, 90%, 95%, or 100% relative to the function of DHODH and wild-type IDH1, wild-type IDH2, mutant IDH1 or mutant IDH2 prior to administration of Cpd 1 or a pharmaceutical composition thereof, as assessed by methods well known in the art.

In a specific aspect, a method for preventing, treating or ameliorating a hematologic cancer in a subject in need thereof as described herein inhibits or reduces the function of DHODH and wild-type IDH1, wild-type IDH2, mutant IDH1 or mutant IDH2 in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and wild-type IDH1, wild-type IDH2, mutant IDH1 or mutant IDH2 prior to administration of Cpd 1 or a pharmaceutical composition thereof, as assessed by methods well known in the art.

In various aspects, a method for preventing, treating or ameliorating a hematologic cancer in a subject in need thereof as described herein inhibits or reduces the function of DHODH and wild-type IDH1, wild-type IDH2, mutant IDH1 or mutant IDH2 in a subject as assessed by methods well known in the art, e.g., ELISA.

In one aspect, a method for preventing, treating or ameliorating a hematologic cancer in a subject in need thereof comprises, administering a combination product having an amount of Cpd 1 or a pharmaceutical composition thereof in combination with an amount of an inhibitor of IDH function or a pharmaceutical composition thereof effective to inhibit or reduce the function of DHODH and IDH in the subject is described herein.

In a specific aspect, the subject is diagnosed with a hematologic cancer capable of being treated by inhibiting or reducing the function of DHODH and IDH in the subject.

In a specific aspect, a method for preventing, treating or ameliorating a hematologic cancer in a subject in need thereof as described herein inhibits or reduces the function of DHODH and IDH in the subject by about 5%, 10%, 15%, 20%, 25%, 30%, 35%, 40%, 45%, 50%, 55%, 60%, 65%, 80%, 85%, 90%, 95%, or 100% relative to the function of DHODH and IDH prior to administration of the combination product having Cpd 1 or a pharmaceutical composition thereof in combination with an amount of an inhibitor of IDH function or a pharmaceutical composition thereof, as assessed by methods well known in the art.

In a specific aspect, a method for preventing, treating or ameliorating a hematologic cancer in a subject in need thereof as described herein inhibits or reduces the function of DHODH and IDH in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and IDH prior to administration of the combination product having Cpd 1 or a pharmaceutical composition thereof in combination with an amount of an inhibitor of IDH function or a pharmaceutical composition thereof, as assessed by methods well known in the art.

In various aspects, a method for preventing, treating or ameliorating a hematologic cancer in a subject in need thereof by administering the combination product as described herein inhibits or reduces the function of DHODH and IDH in a subject as assessed by methods well known in the art, e.g., ELISA.

In one aspect, a method for preventing, treating or ameliorating a hematologic cancer in a subject in need thereof comprises, administering a combination product having an amount of Cpd 1 or a pharmaceutical composition thereof in combination with an amount of an inhibitor of IDH function or a pharmaceutical composition thereof effective to inhibit or reduce the function of DHODH and wild-type IDH or mutant IDH in the subject is described herein.

In another specific aspect, the subject is diagnosed with a hematologic cancer capable of being treated by inhibiting or reducing the function of DHODH and wild-type IDH or mutant IDH in the subject.

In a specific aspect, a method for preventing, treating or ameliorating a hematologic cancer in a subject in need thereof as described herein inhibits or reduces the function of DHODH and wild-type IDH or mutant IDH in the subject by about 5%, 10%, 15%, 20%, 25%, 30%, 35%, 40%, 45%, 50%, 55%, 60%, 65%, 80%, 85%, 90%, 95%, or 100% relative to the function of DHODH and wild-type IDH or mutant IDH prior to administration of the combination product having Cpd 1 or a pharmaceutical composition thereof in combination with an amount of an inhibitor of IDH function or a pharmaceutical composition thereof, as assessed by methods well known in the art.

In a specific aspect, a method for preventing, treating or ameliorating a hematologic cancer in a subject in need thereof as described herein inhibits or reduces the function of DHODH and wild-type IDH or mutant IDH in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and wild-type IDH or mutant IDH prior to administration of the combination product having Cpd 1 or a pharmaceutical composition thereof in combination with an amount of an inhibitor of IDH function or a pharmaceutical composition thereof, as assessed by methods well known in the art.

In one aspect, a method for preventing, treating or ameliorating a hematologic cancer in a subject in need thereof comprises, administering a combination product having an amount of Cpd 1 or a pharmaceutical composition thereof in combination with an amount of an inhibitor of IDH function or a pharmaceutical composition thereof effective to inhibit or reduce the function of DHODH and wild-type IDH1, wild-type IDH2, mutant IDH1 or mutant IDH2 in the subject is described herein.

In a more specific aspect, the subject is diagnosed with a hematologic cancer capable of being treated by inhibiting or reducing the function of DHODH and wild-type IDH1, wild-type IDH2, mutant IDH1 or mutant IDH2 in the subject.

In a specific aspect, a method for preventing, treating or ameliorating a hematologic cancer in a subject in need thereof as described herein inhibits or reduces the function of DHODH and wild-type IDH1, wild-type IDH2, mutant IDH1 or mutant IDH2 in the subject by about 5%, 10%, 15%, 20%, 25%, 30%, 35%, 40%, 45%, 50%, 55%, 60%, 65%, 80%, 85%, 90%, 95%, or 100% relative to the function of DHODH and wild-type IDH1, wild-type IDH2, mutant IDH1 or mutant IDH2 prior to administration of the combination product having Cpd 1 or a pharmaceutical composition thereof in combination with an amount of an inhibitor of IDH function or a pharmaceutical composition thereof, as assessed by methods well known in the art.

In a specific aspect, a method for preventing, treating or ameliorating a hematologic cancer in a subject in need thereof as described herein inhibits or reduces the function of DHODH and wild-type IDH1, wild-type IDH2, mutant IDH1 or mutant IDH2 in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the function of DHODH and wild-type IDH1, wild-type IDH2, mutant IDH1 or mutant IDH2 prior to administration of the combination product having Cpd 1 or a pharmaceutical composition thereof in combination with an amount of an inhibitor of IDH function or a pharmaceutical composition thereof, as assessed by methods well known in the art.

In various aspects, a method for preventing, treating or ameliorating a hematologic cancer in a subject in need thereof by administering the combination product as described herein decreases the concentration of DHODH and IDH or certain biomarkers in a subject as assessed by methods well known in the art, e.g., ELISA.

In a specific aspect, a method for preventing, treating or ameliorating a hematologic cancer as described herein decreases the concentrations of one or more biomarkers in the subject by about 5%, 10%, 15%, 20%, 25%, 30%, 35%, 40%, 45%, 50%, 55%, 60%, 65%, 80%, 85%, 90%, 95%, or 100% relative to the respective concentration observed prior to administration of the combination product having Cpd 1 or a pharmaceutical composition thereof in combination with an amount of an inhibitor of IDH function or a pharmaceutical composition thereof, as assessed by methods well known in the art, e.g., ELISA.

In a specific aspect, a method for preventing, treating or ameliorating a hematologic cancer as described herein decreases the concentrations of one or more biomarkers in the blood of a subject in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the respective concentration observed prior to administration of the combination product having Cpd 1 or a pharmaceutical composition thereof in combination with an amount of an inhibitor of IDH function or a pharmaceutical composition thereof, as assessed by methods well known in the art, e.g., ELISA.

In certain aspects, the methods for preventing, treating or ameliorating a hematologic cancer provided herein prolong or delay the G1/S or late G1/S phase of the cell cycle (i.e., the period between the late resting or pre-DNA synthesis phase, and the early DNA synthesis phase).

In some aspects, the methods for preventing, treating or ameliorating a hematologic cancer provided herein reduce, ameliorate, or alleviate the severity of the hematologic cancer and/or one or more symptoms thereof.

In other aspects, the methods for preventing, treating or ameliorating a hematologic cancer provided herein reduce hospitalization (e.g., the frequency or duration of hospitalization) of a subject diagnosed with the hematologic cancer.

In some aspects, the methods for preventing, treating or ameliorating a hematologic cancer provided herein reduce hospitalization length of a subject diagnosed with the hematologic cancer.

In certain aspects, the methods provided herein increase the survival of a subject diagnosed with a hematologic cancer. In specific aspects, the methods provided herein increase the survival of a subject diagnosed with a hematologic cancer by about 6 months or more, about 7 months or more, about 8 months or more, about 9 months or more, or about 12 months or more.

In particular aspects, the methods for preventing, treating or ameliorating a hematologic cancer provided herein inhibit or reduce the progression of the hematologic cancer, or one or more symptoms associated therewith. In specific aspects, the methods for preventing, treating or ameliorating a hematologic cancer provided herein enhance or improve the therapeutic effect of another therapy (e.g., an anti-cancer agent, radiation, drug therapy, such as chemotherapy, antiandrogen therapy, or surgery). In certain aspects, the methods for preventing, treating or ameliorating a hematologic cancer provided herein involve the use of Cpd 1 or a pharmaceutical composition thereof as an adjuvant therapy.

In particular aspects, the methods for preventing, treating or ameliorating a hematologic cancer provided herein reduce the mortality of subjects diagnosed with the hematologic cancer. In certain aspects, the methods for preventing, treating or ameliorating a hematologic cancer provided herein increase the number of subjects in remission or decrease the hospitalization rate. In other aspects, the methods for preventing, treating or ameliorating a hematologic cancer provided herein prevent the development, onset or progression of one or more symptoms associated with the hematologic cancer.

In particular aspects, the methods for preventing, treating or ameliorating a hematologic cancer provided herein increase symptom-free survival of cancer subjects. In some aspects, the methods for preventing, treating or ameliorating a hematologic cancer provided herein do not cure the cancer in subjects, but prevent the progression or worsening of the disease. In some aspects, the methods for preventing, treating or ameliorating a hematologic cancer provided herein improve the subject's quality of life.

In specific aspects, the methods for preventing, treating or ameliorating a hematologic cancer provided herein decrease the number of CTCs in the blood of a subject by at least about 5%, 10%, 15%, 20%, 25%, 30%, 35%, 40%, 45%, 50%, 55%, 60%, 65%, 80%, 85%, 90%, 95%, 99%, or 100%, relative to the number of CTCs observed prior to administration of Cpd 1 or a pharmaceutical composition thereof, as assessed by methods well known in the art.

In particular aspects, the methods for preventing, treating or ameliorating a hematologic cancer provided herein decrease the number of CTCs in the blood of a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the number of CTCs in the blood observed prior to the administration of Cpd 1 or a pharmaceutical composition thereof, as assessed by methods well known in the art, such as CellSearch immunomagnetic-capture.

In certain aspects, the methods for preventing, treating or ameliorating a hematologic cancer provided herein increase the cancer-free survival rate of subjects diagnosed with the cancer. In some aspects, the methods for preventing, treating or ameliorating a hematologic cancer provided herein increase relapse-free survival. In certain aspects, the methods for preventing, treating or ameliorating a hematologic cancer provided herein increase the number of subjects in remission. In other aspects, the methods for preventing, treating or ameliorating a hematologic cancer provided herein increase the length of remission in subjects.

Treatment Population

In some aspects, a subject treated for a hematologic cancer in accordance with the methods provided herein is a human who has or is diagnosed with a hematologic cancer. In other aspects, a subject treated for a hematologic cancer in accordance with the methods provided herein is a human predisposed or susceptible to a hematologic cancer. In some aspects, a subject treated for a hematologic cancer in accordance with the methods provided herein is a human at risk of developing a hematologic cancer.

In one aspect, a subject treated for a hematologic cancer in accordance with the methods provided herein is a human infant. In another aspect, a subject treated for a hematologic cancer in accordance with the methods provided herein is a human toddler. In another aspect, a subject treated for a hematologic cancer in accordance with the methods provided herein is a human child. In another aspect, a subject treated for a hematologic cancer in accordance with the methods provided herein is a human adult. In another aspect, a subject treated for a hematologic cancer in accordance with the methods provided herein is a middle-aged human. In another aspect, a subject treated for a hematologic cancer in accordance with the methods provided herein is an elderly human.

In certain aspects, a subject treated for cancer in accordance with the methods provided herein has a cancer that metastasized to other areas of the body, such as the bones, lung and liver. In certain aspects, a subject treated for cancer in accordance with the methods provided herein is in remission from the cancer. In some aspects, a subject treated for cancer in accordance with the methods provided herein that has a recurrence of the cancer. In certain aspects, a subject treated in accordance with the methods provided herein is experiencing recurrence of one or more leukemias associated with the hematologic cancer.

In certain aspects, a subject treated for a hematologic cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between.

In a specific aspect, a subject treated for a hematologic cancer in accordance with the methods provided herein is a human that is 18 years old or older. In a particular aspect, a subject treated for a hematologic cancer in accordance with the methods provided herein is a human child that is between the age of 1 year old to 18 years old. In a certain aspect, a subject treated for a hematologic cancer in accordance with the methods provided herein is a human that is between the age of 12 years old and 18 years old. In a certain aspect, the subject is a male human. In another aspect, the subject is a female human. In one aspect, the subject is a female human that is not pregnant or is not breastfeeding. In one aspect, the subject is a female that is pregnant or will/might become pregnant, or is breast feeding.

In particular aspects, a subject treated for a hematologic cancer in accordance with the methods provided herein is a human that is in an immunocompromised state or immuno-suppressed state. In certain aspects, a subject treated for a hematologic cancer in accordance with the methods provided herein is a human receiving or recovering from immunosuppressive therapy. In certain aspects, a subject treated for a hematologic cancer in accordance with the methods provided herein is a human that has or is at risk of getting a hematologic cancer. In certain aspects, a subject treated for a hematologic cancer in accordance with the methods provided herein is a human who is, will or has undergone surgery, drug therapy, such as chemotherapy, hormonal therapy and/or radiation therapy.

In some aspects, a subject treated for a hematologic cancer in accordance with the methods provided herein is administered Cpd 1 or a pharmaceutical composition thereof or a pharmaceutical composition thereof, or a combination therapy before any adverse effects or intolerance to therapies other than Cpd 1 develops. In some aspects, a subject treated for a hematologic cancer in accordance with the methods provided herein is a refractory subject. In certain aspects, a refractory subject is a subject refractory to a standard therapy (e.g., surgery, radiation, anti-androgen therapy and/or drug therapy such as chemotherapy). In certain aspects, a subject with a hematologic cancer is refractory to a therapy when the hematologic cancer has not significantly been eradicated and/or the one or more symptoms have not been significantly alleviated. The determination of whether a patient is refractory can be made either in vivo or in vitro by any method known in the art for assaying the effectiveness of a treatment of a hematologic cancer, using art-accepted meanings of "refractory" in such a context.

In some aspects, a subject treated for a hematologic cancer in accordance with the methods provided herein is a human that has proven refractory to therapies other than treatment with Cpd 1 or a pharmaceutical composition thereof, but is no longer on these therapies. In certain aspects, a subject treated for a hematologic cancer in accordance with the methods provided herein is a human already receiving one or more conventional anti-cancer therapies, such as surgery, drug therapy such as chemotherapy, anti-androgen therapy or radiation. Among these subjects are refractory subjects, subjects who are too young for conventional therapies, and subjects with recurring hematologic cancers despite treatment with existing therapies.

In some aspects, a subject treated for a hematologic cancer in accordance with the methods provided herein is a human susceptible to adverse reactions to conventional therapies. In some aspects, a subject treated for a hematologic cancer in accordance with the methods provided herein is a human that has not received a therapy, e.g., drug therapy such as chemotherapy, surgery, anti-androgen therapy or radiation therapy, prior to the administration of Cpd 1 or a pharmaceutical composition thereof. In other aspects, a subject treated for a hematologic cancer in accordance with the methods provided herein is a human that has received a therapy prior to administration of Cpd 1 or a pharmaceutical composition thereof. In some aspects, a subject treated for a hematologic cancer in accordance with the methods provided herein is a human that has experienced adverse side effects to the prior therapy or the prior therapy was discontinued due to unacceptable levels of toxicity to the human.

In some aspects, a subject treated for a hematologic cancer in accordance with the methods provided herein is not, has not and/or will not receive a drug that is primarily metabolized by CYP2D6. In particular aspects, a subject treated for a hematologic cancer in accordance with the methods provided herein has not and will not receive a drug that is primarily metabolized by CYP2D6 1, 2, 3 or 4 weeks before receiving Cpd 1 or a pharmaceutical composition thereof and 1, 2, 3 or 4 weeks after receiving Cpd 1 or a pharmaceutical composition thereof. Examples of such drugs include, without limitation, some antidepressants (e.g., tricyclic antidepressants and selective serotonin uptake inhibitors), some antipsychotics, some beta-adrenergic receptor blockers, certain antiviral agents and certain antiarrhythmic agents. In specific aspects, a subject treated for a hematologic cancer in accordance with the methods provided herein is not, has not and/or will not receive tamoxifen. In particular aspects, a subject treated for a hematologic cancer in accordance with the methods provided herein has not and will not receive tamoxifen 1, 2, 3 or 4 weeks before receiving Cpd 1 or a pharmaceutical composition thereof and 1, 2, 3 or 4 weeks after receiving Cpd 1 or a pharmaceutical composition thereof. In specific aspects, a subject treated for a hematologic cancer in accordance with the methods provided herein has received tamoxifen, e.g., for 1, 2, 3 or 4 weeks before receiving Cpd 1 or a pharmaceutical composition thereof.

Dosage and Administration

In accordance with the methods for preventing, treating or ameliorating a hematologic cancer provided herein, Cpd 1 or a pharmaceutical composition thereof can be administered to a subject in need thereof by a variety of routes in amounts which result in a beneficial or therapeutic effect. Cpd 1 or a pharmaceutical composition thereof may be orally administered to a subject in need thereof in accordance with the methods for preventing, treating or ameliorating a hematologic cancer provided herein. The oral administration of Cpd 1 or a pharmaceutical composition thereof may facilitate subjects in need of such treatment complying with a regimen for taking Cpd 1 or a pharmaceutical composition thereof. Thus, in a specific aspect, Cpd 1 or a pharmaceutical composition thereof is administered orally to a subject in need thereof. In another aspect, Cpd 1 or a pharmaceutical composition thereof provided herein can be administered orally, with or without food or water.

Other routes of administration include, but are not limited to, intravenous, intradermal, intrathecal, intramuscular, subcutaneous, intranasal, inhalation, transdermal, topical, transmucosal, intracranial, epidural and intra-synovial. In one aspect, Cpd 1 or a pharmaceutical composition thereof is administered systemically (e.g., parenterally) to a subject in need thereof. In one aspect, Cpd 1 or a pharmaceutical composition thereof is administered via a route that permits Cpd 1 or a pharmaceutical composition thereof to cross the blood-brain barrier (e.g., orally).

Evaluation has indicated that Cpd 1 penetrates the blood-brain barrier. Table 4 provides brain tissue plasma concentration ratios determined by whole-body autoradiography at specified times after a single oral administration of $^{14}$C-Cpd 1 to rats (50 mg/kg).

TABLE 4

Blood-Brain Barrier Penetration

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Medulla | 1.60 | 1.42 | 1.98 | 3.82 | 1.83 | 1.69 | 1.20 | 2.01 | NA | 1.88 |
| Olfactory lobe | 1.42 | 1.38 | 1.35 | 2.45 | 1.23 | 1.13 | 0.97 | NA | NA | 3.33 |
| Pituitary gland | 4.06 | 4.27 | 3.22 | 5.48 | 2.72 | 2.33 | 0.89 | 3.68 | NA | 1.58 |
| Spinal cord | 1.14 | 0.89 | 1.24 | 1.92 | 1.75 | 1.60 | 1.43 | 1.60 | 1.84 | 2.75 |

In accordance with the methods for preventing, treating or ameliorating a hematologic cancer provided herein that involve administration of Cpd 1 or a pharmaceutical composition thereof in combination with one or more additional therapies, Cpd 1 or a pharmaceutical composition thereof and one or more additional therapies may be administered by the same route or a different route of administration.

The dosage and frequency of administration of Cpd 1 or a pharmaceutical composition thereof is administered to a subject in need thereof in accordance with the methods for preventing, treating or ameliorating a hematologic cancer provided herein will be efficacious while minimizing any side effects. The exact dosage and frequency of administration of Cpd 1 or a pharmaceutical composition thereof can be determined by a practitioner, in light of factors related to the subject that requires treatment.

Factors which may be taken into account include the severity of the disease state, general health of the subject, age, weight, and gender of the subject, diet, time and frequency of administration, drug combination(s), reaction sensitivities, and tolerance/response to therapy. The dosage and frequency of administration of Cpd 1 or a pharmaceutical composition thereof may be adjusted over time to provide an effective amount of Cpd 1 or a pharmaceutical composition thereof or to maintain the desired effect.

As described herein, the methods for preventing, treating or ameliorating a hematologic cancer in a subject in need thereof presented herein comprises, administering to the subject an effective amount of Cpd 1 or a pharmaceutical composition thereof, wherein the effective amount is an initial dose, then a loading dose followed by a maintenance dose thereafter.

In one aspect, a method for preventing, treating or ameliorating a hematologic cancer in a subject in need thereof comprises, administering to the subject an effective amount of Cpd 1 or a pharmaceutical composition thereof, wherein the effective amount is a loading dose followed by a maintenance dose thereafter.

In a specific aspect, the effective amount is an initial dose administered to the subject for one day once per day.

In a specific aspect, the effective amount is a loading dose administered to the subject for seven days once or twice per day.

In a specific aspect, the effective amount is a loading dose administered to the subject for seven days once per day.

In a specific aspect, the effective amount is a maintenance dose administered to the subject once per day.

In another aspect, a method for preventing, treating or ameliorating a hematologic cancer in a subject in need thereof comprises the administration of an effective amount of Cpd 1 or a pharmaceutical composition thereof to the subject wherein the effective amount is an initial dose, then a loading dose followed by a maintenance dose, wherein the dose is selected from a dose in a range of from about 1 mg to about 200 mg, from about 1 mg to about 210 mg, from about 1 mg to about 190 mg, from about 1 mg to about 180 mg, from about 1 mg to about 170 mg, from about 1 mg to about 160 mg, from about 1 mg to about 150 mg, from about 1 mg to about 140 mg, from about 1 mg to about 130 mg, from about 1 mg to about 120 mg, from about 1 mg to about 110 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 1 mg to about 40 mg, from about 1 mg to about 30 mg, from about 1 mg to about 20 mg, from about 1 mg to about 10 mg, from about 10 mg to about 200 mg, from about 20 mg to about 200 mg, from about 30 mg to about 200 mg, from about 40 mg to about 200 mg, from about 50 mg to about 200 mg, from about 60 mg to about 200 mg, from about 70 mg to about 200 mg, from about 80 mg to about 200 mg, from about 90 mg to about 200 mg, from about 100 mg to about 200 mg, from about 110 mg to about 200 mg, from about 120 mg to about 200 mg, from about 130 mg to about 200 mg, from about 140 mg to about 200 mg, from about 150 mg to about 200 mg, from about 160 mg to about 200 mg, from about 170 mg to about 200 mg, from about 180 mg to about 200 mg, from about 190 mg to about 200 mg, from about 200 mg to about 210 mg, from about 10 mg to about 200 mg, from about 10 mg to about 190 mg, from about 10 mg to about 180 mg, from about 10 mg to about 170 mg, from about 10 mg to about 160 mg, from about 10 mg to about 150 mg, from about 10 mg to about 140 mg, from about 10 mg to about 130 mg, from about 10 mg to about 120 mg, from about 10 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, from about 20 mg to about 200 mg, from about 20 mg to about 190 mg, from about 20 mg to about 180 mg, from about 20 mg to about 170 mg, from about 20 mg to about 160 mg, from about 20 mg to about 150 mg, from about 20 mg to about 140 mg, from about 20 mg to about 130 mg, from about 20 mg to about 120 mg, from about 20 mg to about 120 mg, from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, from about 20 mg to about 40 mg, from about 20 mg to about 30 mg, from about 30 mg to about 40 mg, from about 30 mg to about 50 mg, from about 30 mg to about 60 mg, from about 30 mg to about 70 mg, from about 40 mg to about 50 mg, from about 40 mg to about 60 mg, from about 40 mg to about 70 mg, from about 50 mg to about 60 mg, from about 50 mg to about 70 mg, from about 60 mg to about 70 mg, from about 90 mg to about 210 mg, from about 90 mg to about 200 mg, from about 90 mg to about 190 mg, from about 90 mg to about 180 mg, from about 90 mg to about 170 mg, from about 90 mg to about 160 mg, from about 90 mg to about 150 mg, from about 90 mg to about 140 mg, from about 90 mg to about 130 mg, from about 90 mg to about 120 mg, from about 90 mg to about 110 mg, from about 100 mg to about 210 mg, from about 100 mg to about 200 mg, from about 100 mg to about 190 mg, from about 100 mg to about 180 mg, from about 100 mg to about 170 mg, from about 100 mg to about 160 mg, from about 100 mg to about 150 mg, from about 100 mg to about 140 mg, from about 100 mg to about 130 mg, from about 100 mg to about 120 mg, from about 100 mg to about 110 mg, from about 110 mg to about 210 mg, from about 120 mg to about 210 mg, from about 130 mg to about 210 mg, from about 140 mg to about 210 mg, from about 150 mg to about 210 mg, from about 160 mg to about 210 mg, from about 170 mg to about 210 mg, from about 180 mg to about 210 mg, from about 190 mg to about 210 mg, from about 1 mg to about 110 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 1 mg to about 40 mg, from about 1 mg to about 30 mg, from about 1 mg to about 20 mg, from about 1 mg to about 10 mg, from about 10 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject wherein the effective amount is a dose selected from a dose in a range of from about 1 mg to about 200 mg, from about 1 mg to about 210 mg, from about 1 mg to about 190 mg, from about 1 mg to about 180 mg, from about 1 mg to about 170 mg, from about 1 mg to about 160 mg, from about 1 mg to about 150 mg, from about 1 mg to about 140 mg, from about 1 mg to about 130 mg, from about 1 mg to about 120 mg, from about 1 mg to about 110 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 1 mg to about 40 mg, from about 1 mg to about 30 mg, from about 1 mg to about 20 mg, from about 1 mg to about 10 mg, from about 10 mg to about 200 mg, from about 20 mg to about 200 mg, from about 30 mg to about 200 mg, from about 40 mg to about 200 mg, from about 50 mg to about 200 mg, from about 60 mg to about 200 mg, from about 70 mg to about 200 mg, from about 80 mg to about 200 mg, from about 90 mg to about 200 mg, from about 100 mg to about 200 mg, from about 110 mg to about 200 mg, from about 120 mg to about 200 mg, from about 130 mg to about 200 mg, from about 140 mg to about 200 mg, from about 150 mg to about 200 mg, from about 160 mg to about 200 mg, from about 170 mg to about 200 mg, from about 180 mg to about 200 mg, from about 190 mg to about 200 mg, from about 200 mg to about 210 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dose selected from a dose in a range of from about 10 mg to about 200 mg, from about 10 mg to about 190 mg, from about 10 mg to about 180 mg, from about 10 mg to about 170 mg, from about 10 mg to about 160 mg, from about 10 mg to about 150 mg, from about 10 mg to about 140 mg, from about 10 mg to about 130 mg, from about 10 mg to about 120 mg, from about 10 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, from about 20 mg to about 200 mg, from about 20 mg to about 190 mg, from about 20 mg to about 180 mg, from about 20 mg to about 170 mg, from about 20 mg to about 160 mg, from about 20 mg to about 150 mg, from about 20 mg to about 140 mg, from about 20 mg to about 130 mg, from about 20 mg to about 120 mg, from about 20 mg to about 120 mg, from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, from about 20 mg to about 40 mg, from about 20 mg to about 30 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose selected from a dose in a range of from about 30 mg to about 40 mg, from about 30 mg to about 50 mg, from about 30 mg to about 60 mg, from about 30 mg to about 70 mg, from about 40 mg to about 50 mg, from about 40 mg to about 60 mg, from about 40 mg to about 70 mg, from about 50 mg to about 60 mg, from about 50 mg to about 70 mg, from about 60 mg to about 70 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose selected from a dose in a range of from about 40 mg to about 50 mg, from about 40 mg to about 60 mg, from about 50 mg to about 60 mg, from about 50 mg to about 70 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose selected from a dose in a range of from about 40 mg to about 60 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose of about 50 mg administered orally once per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose selected from a dose in a range of from about 90 mg to about 210 mg, from about 90 mg to about 200 mg, from about 90 mg to about 190 mg, from about 90 mg to about 180 mg, from about 90 mg to about 170 mg, from about 90 mg to about 160 mg, from about 90 mg to about 150 mg, from about 90 mg to about 140 mg, from about 90 mg to about 130 mg, from about 90 mg to about 120 mg, from about 90 mg to about 110 mg, from about 100 mg to about 210 mg, from about 100 mg to about 200 mg, from about 100 mg to about 190 mg, from about 100 mg to about 180 mg, from about 100 mg to about 170 mg, from about 100 mg to about 160 mg, from about 100 mg to about 150 mg, from about 100 mg to about 140 mg, from about 100 mg to about 130 mg, from about 100 mg to about 120 mg, from about 100 mg to about 110 mg, from about 110 mg to about 210 mg, from about 120 mg to about 210 mg, from about 130 mg to about 210 mg, from about 140 mg to about 210 mg, from about 150 mg to about 210 mg, from about 160 mg to about 210 mg, from about 170 mg to about 210 mg, from about 180 mg to about 210 mg, from about 190 mg to about 210 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose selected from a dose in a range of from about 90 mg to about 210 mg, from about 90 mg to about 200 mg, from about 90 mg to about 190 mg, from about 100 mg to about 210 mg, from about 100 mg to about 200 mg, from about 100 mg to about 190 mg, from about 110 mg to about 210 mg, from about 120 mg to about 210 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose in a range of from about 100 mg to about 200 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose of about 100 mg administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 1 mg to about 110 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 1 mg to about 40 mg, from about 1 mg to about 30 mg, from about 1 mg to about 20 mg, from about 1 mg to about 10 mg, from about 10 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 1 mg to about 110 mg, from about 1 mg to about 100 mg, from about 1 mg to about 90 mg, from about 10 mg to about 110 mg, from about 10 mg to about 100 mg, from about 10 mg to about 90 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 1 mg to about 100 mg, from about 10 mg to about 100 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 1 mg to about 100 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 10 mg to about 100 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose of about 50 mg administered orally once or twice per day.

In another aspect, a method for preventing, treating or ameliorating a hematologic cancer in a subject in need thereof comprises the administration of an effective amount of Cpd 1 or a pharmaceutical composition thereof to the subject, wherein the effective amount is an initial dose, then a loading dose followed by a maintenance dose, wherein the dose is selected from a dose in a range of from about 4 mg to about 84 mg, from about 4 mg to about 80 mg, from about 4 mg to about 76 mg, from about 4 mg to about 72 mg, from about 4 mg to about 68 mg, from about 4 mg to about 64 mg, from about 4 mg to about 60 mg, from about 4 mg to about 56 mg, from about 4 mg to about 52 mg, from about 4 mg to about 48 mg, from about 4 mg to about 44 mg, from about 4 mg to about 40 mg, from about 4 mg to about 36 mg, from about 4 mg to about 32 mg, from about 4 mg to about 28 mg, from about 4 mg to about 24 mg, from about 4 mg to about 20 mg, from about 4 mg to about 16 mg, from about 4 mg to about 12 mg, from about 4 mg to about 8 mg, from about 8 mg to about 80 mg, from about 12 mg to about 80 mg, from about 16 mg to about 80 mg, from about 20 mg to about 80 mg, from about 24 mg to about 80 mg, from about 28 mg to about 80 mg, from about 32 mg to about 80 mg, from about 36 mg to about 80 mg, from about 40 mg to about 80 mg, from about 44 mg to about 80 mg, from about 48 mg to about 80 mg, from about 52 mg to about 80 mg, from about 56 mg to about 80 mg, from about 60 mg to about 80 mg, from about 64 mg to about 80 mg, from about 68 mg to about 80 mg, from about 72 mg to about 80 mg, from about 76 mg to about 80 mg, from about 8 mg to about 84 mg, from about 12 mg to about 84 mg, from about 16 mg to about 84 mg, from about 20 mg to about 84 mg, from about 24 mg to about 84 mg, from about 28 mg to about 84 mg, from about 32 mg to about 84 mg, from about 36 mg to about 84 mg, from about 40 mg to about 84 mg, from about 44 mg to about 84 mg, from about 48 mg to about 84 mg, from about 52 mg to about 84 mg, from about 56 mg to about 84 mg, from about 60 mg to about 84 mg, from about 64 mg to about 84 mg, from about 68 mg to about 84 mg, from about 72 mg to about 84 mg, from about 76 mg to about 84 mg, from about 12 mg to about 16 mg, from about 12 mg to about 20 mg, from about 12 mg to about 24 mg, from about 12 mg to about 28 mg, from about 12 mg to about 28 mg, from about 16 mg to about 20 mg, from about 16 mg to about 24 mg, from about 20 mg to about 24 mg, from about 20 mg to about 28 mg, from about 24 mg to about 28 mg, from about 32 mg to about 88 mg, 32 mg to about 84 mg, from about 32 mg to about 80 mg, from about 32 mg to about 76 mg, from about 32 mg to about 72 mg, from about 32 mg to about 68 mg, from about 32 mg to about 64 mg, from about 32 mg to about 60 mg, from about 32 mg to about 56 mg, from about 32 mg to about 52 mg, from about 32 mg to about 48 mg, from about 32 mg to about 44 mg, from about 32 mg to about 40 mg, from about 32 mg to about 36 mg, from about 36 mg to about 88 mg, from about 36 mg to about 84 mg, from about 36 mg to about 80 mg, from about 36 mg to about 76 mg, from about 36 mg to about 72 mg, from about 36 mg to about 68 mg, from about 36 mg to about 64 mg, from about 36 mg to about 60 mg, from about 36 mg to about 56 mg, from about 36 mg to about 52 mg, from about 36 mg to about 48 mg, from about 36 mg to about 44 mg, from about 36 mg to about 40 mg, from about 40 mg to about 88 mg, 40 mg to about 84 mg, from about 40 mg to about 80 mg, from about 40 mg to about 76 mg, from about 40 mg to about 72 mg, from about 40 mg to about 68 mg, from about 40 mg to about 64 mg, from about 40 mg to about 60 mg, from about 40 mg to about 56 mg, from about 40 mg to about 52 mg, from about 40 mg to about 48 mg, from about 40 mg to about 44 mg, from about 44 mg to about 88 mg, from about 48 mg to about 88 mg, from about 52 mg to about 88 mg, from about 56 mg to about 88 mg, from about 60 mg to about 88 mg, from about 64 mg to about 88 mg, from about 68 mg to about 88 mg, from about 72 mg to about 88 mg, from about 76 mg to about 88 mg, from about 80 mg to about 88 mg, from about 84 mg to about 88 mg, from about 44 mg to about 84 mg, from about 48 mg to about 84 mg, from about 52 mg to about 84 mg, from about 56 mg to about 84 mg, from about 60 mg to about 84 mg, from about 64 mg to about 84 mg, from about 68 mg to about 84 mg, from about 72 mg to about 84 mg, from about 76 mg to about 84 mg, from about 80 mg to about 84 mg, from about 44 mg to about 80 mg, from about 48 mg to about 80 mg, from about 52 mg to about 80 mg, from about 56 mg to about 80 mg, from about 60 mg to about 80 mg, from about 64 mg to about 80 mg, from about 68 mg to about 80 mg, from about 72 mg to about 80 mg, from about 76 mg to about 80 mg, from about 84 mg to about 80 mg, from about 4 mg to about 48 mg, from about 4 mg to about 44 mg, from about 4 mg to about 40 mg, from about 4 mg to about 36 mg, from about 4 mg to about 32 mg, from about 4 mg to about 28 mg, from about 4 mg to about 24 mg, from about 4 mg to about 20 mg, from about 4 mg to about 16 mg, from about 4 mg to about 12 mg, from about 4 mg to about 8 mg, from about 8 mg to about 48 mg, from about 8 mg to about 44 mg, from about 8 mg to about 40 mg, from about 8 mg to about 36 mg, from about 8 mg to about 32 mg, from about 8 mg to about 28 mg, from about 8 mg to about 24 mg, from about 8 mg to about 20 mg, from about 8 mg to about 16 mg, from about 8 mg to about 12 mg, from about 12 mg to about 48 mg, from about 12 mg to about 44 mg, from about 12 mg to about 40 mg, from about 12 mg to about 36 mg, from about 12 mg to about 32 mg, from about 12 mg to about 28 mg, from about 12 mg to about 24 mg, from about 12 mg to about 20 mg, from about 12 mg to about 16 mg, from about 16 mg to about 48 mg, from about 20 mg to about 48 mg, from about 24 mg to about 48 mg, from about 26 mg to about 48 mg, from about 30 mg to about 48 mg, from about 34 mg to about 48 mg, from about 38 mg to about 48 mg, from about 40 mg to about 48 mg, from about 44 mg to about 48 mg, from about 16 mg to about 44 mg, from about 20 mg to about 44 mg, from about 24 mg to about 44 mg, from about 26 mg to about 44 mg, from about 30 mg to about 44 mg, from about 34 mg to about 44 mg, from about 38 mg to about 44 mg, from about 40 mg to about 44 mg, from about 16 mg to about 40 mg, from about 20 mg to about 40 mg, from about 24 mg to about 40 mg, from about 26 mg to about 40 mg, from about 30 mg to about 40 mg, from about 34 mg to about 40 mg, from about 38 mg to about 40 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dose selected from a dose in a range of from about 4 mg to about 84 mg, from about 4 mg to about 80 mg, from about 4 mg to about 76 mg, from about 4 mg to about 72 mg, from about 4 mg to about 68 mg, from about 4 mg to about 64 mg, from about 4 mg to about 60 mg, from about 4 mg to about 56 mg, from about 4 mg to about 52 mg, from about 4 mg to about 48 mg, from about 4 mg to about 44 mg, from about 4 mg to about 40 mg, from about 4 mg to about 36 mg, from about 4 mg to about 32 mg, from about 4 mg to about 28 mg, from about 4 mg to about 24 mg, from about 4 mg to about 20 mg, from about 4 mg to about 16 mg, from about 4 mg to about 12 mg, from about 4 mg to about 8 mg, from about 8 mg to about 80 mg, from about 12 mg to about 80 mg, from about 16 mg to about 80 mg, from about 20 mg to about 80 mg, from about 24 mg to about 80 mg, from about 28 mg to about 80 mg, from about 32 mg to about 80 mg, from about 36 mg to about 80 mg, from about 40 mg to about 80 mg, from about 44 mg to about 80 mg, from about 48 mg to about 80 mg, from about 52 mg to about 80 mg, from about 56 mg to about 80 mg, from about 60 mg to about 80 mg, from about 64 mg to about 80 mg, from about 68 mg to about 80 mg, from about 72 mg to about 80 mg, from about 76 mg to about 80 mg, from about 8 mg to about 84 mg, from about 12 mg to about 84 mg, from about 16 mg to about 84 mg, from about 20 mg to about 84 mg, from about 24 mg to about 84 mg, from about 28 mg to about 84 mg, from about 32 mg to about 84 mg, from about 36 mg to about 84 mg, from about 40 mg to about 84 mg, from about 44 mg to about 84 mg, from about 48 mg to about 84 mg, from about 52 mg to about 84 mg, from about 56 mg to about 84 mg, from about 60 mg to about 84 mg, from about 64 mg to about 84 mg, from about 68 mg to about 84 mg, from about 72 mg to about 84 mg, from about 76 mg to about 84 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose selected from a dose in a range of from about 12 mg to about 16 mg, from about 12 mg to about 20 mg, from about 12 mg to about 24 mg, from about 12 mg to about 28 mg, from about 12 mg to about 28 mg, from about 16 mg to about 20 mg, from about 16 mg to about 24 mg, from about 20 mg to about 24 mg, from about 20 mg to about 28 mg, from about 24 mg to about 28 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose selected from a dose in a range of from about 16 mg to about 20 mg, from about 16 mg to about 24 mg, from about 20 mg to about 24 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is an initial dose of about 20 mg administered orally once per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose selected from a dose in a range of from about 32 mg to about 88 mg, 32 mg to about 84 mg, from about 32 mg to about 80 mg, from about 32 mg to about 76 mg, from about 32 mg to about 72 mg, from about 32 mg to about 68 mg, from about 32 mg to about 64 mg, from about 32 mg to about 60 mg, from about 32 mg to about 56 mg, from about 32 mg to about 52 mg, from about 32 mg to about 48 mg, from about 32 mg to about 44 mg, from about 32 mg to about 40 mg, from about 32 mg to about 36 mg, from about 36 mg to about 88 mg, from about 36 mg to about 84 mg, from about 36 mg to about 80 mg, from about 36 mg to about 76 mg, from about 36 mg to about 72 mg, from about 36 mg to about 68 mg, from about 36 mg to about 64 mg, from about 36 mg to about 60 mg, from about 36 mg to about 56 mg, from about 36 mg to about 52 mg, from about 36 mg to about 48 mg, from about 36 mg to about 44 mg, from about 36 mg to about 40 mg, from about 40 mg to about 88 mg, 40 mg to about 84 mg, from about 40 mg to about 80 mg, from about 40 mg to about 76 mg, from about 40 mg to about 72 mg, from about 40 mg to about 68 mg, from about 40 mg to about 64 mg, from about 40 mg to about 60 mg, from about 40 mg to about 56 mg, from about 40 mg to about 52 mg, from about 40 mg to about 48 mg, from about 40 mg to about 44 mg, from about 44 mg to about 88 mg, from about 48 mg to about 88 mg, from about 52 mg to about 88 mg, from about 56 mg to about 88 mg, from about 60 mg to about 88 mg, from about 64 mg to about 88 mg, from about 68 mg to about 88 mg, from about 72 mg to about 88 mg, from about 76 mg to about 88 mg, from about 80 mg to about 88 mg, from about 84 mg to about 88 mg, from about 44 mg to about 84 mg, from about 48 mg to about 84 mg, from about 52 mg to about 84 mg, from about 56 mg to about 84 mg, from about 60 mg to about 84 mg, from about 64 mg to about 84 mg, from about 68 mg to about 84 mg, from about 72 mg to about 84 mg, from about 76 mg to about 84 mg, from about 80 mg to about 84 mg, from about 44 mg to about 80 mg, from about 48 mg to about 80 mg, from about 52 mg to about 80 mg, from about 56 mg to about 80 mg, from about 60 mg to about 80 mg, from about 64 mg to about 80 mg, from about 68 mg to about 80 mg, from about 72 mg to about 80 mg, from about 76 mg to about 80 mg, from about 84 mg to about 80 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose selected from a dose in a range of from about 36 mg to about 88 mg, from about 36 mg to about 84 mg, from about 36 mg to about 80 mg, from about 36 mg to about 76 mg, from about 36 mg to about 72 mg, from about 40 mg to about 88 mg, 40 mg to about 84 mg, from about 40 mg to about 80 mg, from about 40 mg to about 76 mg, from about 40 mg to about 72 mg, from about 44 mg to about 88 mg, from about 48 mg to about 88 mg, from about 44 mg to about 84 mg, from about 48 mg to about 84 mg, from about 44 mg to about 80 mg, from about 48 mg to about 80 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose selected from a dose in a range of from about 36 mg to about 84 mg, from about 36 mg to about 80 mg, from about 36 mg to about 76 mg, 40 mg to about 84 mg, from about 40 mg to about 80 mg, from about 40 mg to about 76 mg, from about 44 mg to about 80 mg, from about 48 mg to about 80 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose in a range of from about 40 mg to about 80 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose of about 40 mg administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a loading dose of about 40 mg administered orally once per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 4 mg to about 48 mg, from about 4 mg to about 44 mg, from about 4 mg to about 40 mg, from about 4 mg to about 36 mg, from about 4 mg to about 32 mg, from about 4 mg to about 28 mg, from about 4 mg to about 24 mg, from about 4 mg to about 20 mg, from about 4 mg to about 16 mg, from about 4 mg to about 12 mg, from about 4 mg to about 8 mg, from about 8 mg to about 48 mg, from about 8 mg to about 44 mg, from about 8 mg to about 40 mg, from about 8 mg to about 36 mg, from about 8 mg to about 32 mg, from about 8 mg to about 28 mg, from about 8 mg to about 24 mg, from about 8 mg to about 20 mg, from about 8 mg to about 16 mg, from about 8 mg to about 12 mg, from about 12 mg to about 48 mg, from about 12 mg to about 44 mg, from about 12 mg to about 40 mg, from about 12 mg to about 36 mg, from about 12 mg to about 32 mg, from about 12 mg to about 28 mg, from about 12 mg to about 24 mg, from about 12 mg to about 20 mg, from about 12 mg to about 16 mg, from about 16 mg to about 48 mg, from about 20 mg to about 48 mg, from about 24 mg to about 48 mg, from about 26 mg to about 48 mg, from about 30 mg to about 48 mg, from about 34 mg to about 48 mg, from about 38 mg to about 48 mg, from about 40 mg to about 48 mg, from about 44 mg to about 48 mg, from about 16 mg to about 44 mg, from about 20 mg to about 44 mg, from about 24 mg to about 44 mg, from about 26 mg to about 44 mg, from about 30 mg to about 44 mg, from about 34 mg to about 44 mg, from about 38 mg to about 44 mg, from about 40 mg to about 44 mg, from about 16 mg to about 40 mg, from about 20 mg to about 40 mg, from about 24 mg to about 40 mg, from about 26 mg to about 40 mg, from about 30 mg to about 40 mg, from about 34 mg to about 40 mg, from about 38 mg to about 40 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 4 mg to about 48 mg, from about 4 mg to about 44 mg, from about 4 mg to about 40 mg, from about 4 mg to about 36 mg, from about 4 mg to about 32 mg, from about 8 mg to about 48 mg, from about 8 mg to about 44 mg, from about 8 mg to about 40 mg, from about 8 mg to about 36 mg, from about 8 mg to about 32 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose selected from a dose in a range of from about 4 mg to about 48 mg, from about 4 mg to about 44 mg, from about 4 mg to about 40 mg, from about 4 mg to about 36 mg, from about 4 mg to about 32 mg, from about 8 mg to about 48 mg, from about 8 mg to about 44 mg, from about 8 mg to about 40 mg, from about 8 mg to about 36 mg, from about 8 mg to about 32 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose in a range of from about 4 mg to about 40 mg, and the like, or any range in between, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose of about 20 mg, administered orally once or twice per day.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a maintenance dose of about 20 mg, administered orally once per day.

In some aspects, a method for preventing, treating or ameliorating a hematologic cancer in a subject in need thereof comprises the administration of an effective amount of Cpd 1 or a pharmaceutical composition thereof to the subject, wherein the effective amount is a dosage that is expressed as mg per meter squared ($mg/m^2$). The $mg/m^2$ for Cpd 1 may be determined, for example, by multiplying a conversion factor for an animal by an animal dose in mg per kilogram (mg/kg) to obtain the dose in $mg/m^2$ for human dose equivalent. For regulatory purposes, the following conversion factors may be used: Mouse=3, Hamster=4.1, Rat=6, Guinea Pig=7.7. (based on Freireich et al., Cancer Chemother. Rep. 50(4):219-244 (1966)). The height and weight of a human may be used to calculate a human body surface area applying Boyd's Formula of Body Surface Area. In specific aspects, a method for preventing, treating or ameliorating a hematologic cancer in a subject in need thereof comprises the administration of an effective amount of Cpd 1 or a pharmaceutical composition thereof to the subject, wherein the effective amount is an amount in the range of from about $0.1 mg/m^2$ to about $1000 mg/m^2$, or any range in between.

In one aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a target mean plasma concentration of Cpd 1 in a subject with a hematologic cancer or an animal model (e.g., an animal model with a pre-established hematologic cancer).

In another aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 44 µg·hr/mL, from approximately 8 µg·hr/mL to approximately 44 µg·hr/mL, from approximately 12 µg·hr/mL to approximately 44 µg·hr/mL, from approximately 16 µg·hr/mL to approximately 44 µg·hr/mL, from approximately 20 µg·hr/mL to approximately 44 µg·hr/mL, from approximately 24 µg·hr/mL to approximately 44 µg·hr/mL, from approximately 28 µg·hr/mL to approximately 44 µg·hr/mL, from approximately 32 µg·hr/mL to approximately 44 µg·hr/mL, from approximately 36 µg·hr/mL to approximately 44 µg·hr/mL, from approximately 40 µg·hr/mL to approximately 44 µg·hr/mL, from approximately 4 µg·hr/mL to approximately 40 µg·hr/mL, from approximately 8 µg·hr/mL to approximately 40 µg·hr/mL, from approximately 12 µg·hr/mL to approximately 40 µg·hr/mL, from approximately 16 µg·hr/mL to approximately 40 µg·hr/mL, from approximately 20 µg·hr/mL to approximately 40 µg·hr/mL, from approximately 24 µg·hr/mL to approximately 40 µg·hr/mL, from approximately 28 µg·hr/mL to approximately 40 µg·hr/mL, from approximately 32 µg·hr/mL to approximately 40 µg·hr/mL, from approximately 36 µg·hr/mL to approximately 40 µg·hr/mL, from approximately 4 µg·hr/mL to approximately 36 µg·hr/mL, from approximately 8 µg·hr/mL to approximately 36 µg·hr/mL, from approximately 12 µg·hr/mL to approximately 36 µg·hr/mL, from approximately 16 µg·hr/mL to approximately 36 µg·hr/mL, from approximately 20 µg·hr/mL to approximately 36 µg·hr/mL, from approximately 24 µg·hr/mL to approximately 36 µg·hr/mL, from approximately 28 µg·hr/mL to approximately 36 µg·hr/mL, from approximately 32 µg·hr/mL to approximately 36 µg·hr/mL, from approximately 4 µg·hr/mL to approximately 32 µg·hr/mL, from approximately 4 µg·hr/mL to approximately 28 µg·hr/mL, from approximately 4 µg·hr/mL to approximately 24 µg·hr/mL, from approximately 4 µg·hr/mL to approximately 20 µg·hr/mL, from approximately 4 µg·hr/mL to approximately 16 µg·hr/mL, from approximately 4 µg·hr/mL to approximately 12 µg·hr/mL, from approximately 4 µg·hr/mL to approximately 8 µg·hr/mL, from approximately 8 µg·hr/mL to approximately 32 µg·hr/mL, from approximately 8 µg·hr/mL to approximately 28 µg·hr/mL, from approximately 8 µg·hr/mL to approximately 24 µg·hr/mL, from approximately 8 µg·hr/mL to approximately 20 µg·hr/mL, from approximately 8 µg·hr/mL to approximately 16 µg·hr/mL, from approximately 8 µg·hr/mL to approximately 12 µg·hr/mL, from approximately 12 µg·hr/mL to approximately 32 µg·hr/mL, from approximately 12 µg·hr/mL to approximately 28 µg·hr/mL, from approximately 12 µg·hr/mL to approximately 24 µg·hr/mL, from approximately 12 µg·hr/mL to approximately 20 µg·hr/mL, from approximately 12 µg·hr/mL to approximately 16 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 44 µg·hr/mL, from approximately 8 µg·hr/mL to approximately 44 µg·hr/mL, from approximately 12 µg·hr/mL to approximately 44 µg·hr/mL, from approximately 16 µg·hr/mL to approximately 44 µg·hr/mL, from approximately 20 µg·hr/mL to approximately 44 µg·hr/mL, from approximately 24 µg·hr/mL to approximately 44 µg·hr/mL, from approximately 28 µg·hr/mL to approximately 44 µg·hr/mL, from approximately 32 µg·hr/mL to approximately 44 µg·hr/mL, from approximately 36 µg·hr/mL to approximately 44 µg·hr/mL, from approximately 40 µg·hr/mL to approximately 44 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 40 µg·hr/mL, from approximately 8 µg·hr/mL to approximately 40 µg·hr/mL, from approximately 12 µg·hr/mL to approximately 40 µg·hr/mL, from approximately 16 µg·hr/mL to approximately 40 µg·hr/mL, from approximately 20 µg·hr/mL to approximately 40 µg·hr/mL, from approximately 24 µg·hr/mL to approximately 40 µg·hr/mL, from approximately 28 µg·hr/mL to approximately 40 µg·hr/mL, from approximately 32 µg·hr/mL to approximately 40 µg·hr/mL, from approximately 36 µg·hr/mL to approximately 40 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 36 µg·hr/mL, from approximately 8 µg·hr/mL to approximately 36 µg·hr/mL, from approximately 12 µg·hr/mL to approximately 36 µg·hr/mL, from approximately 16 µg·hr/mL to approximately 36 µg·hr/mL, from approximately 20 µg·hr/mL to approximately 36 µg·hr/mL, from approximately 24 µg·hr/mL to approximately 36 µg·hr/mL, from approximately 28 µg·hr/mL to approximately 36 µg·hr/mL, from approximately 32 µg·hr/mL to approximately 36 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 32 µg·hr/mL, from approximately 4 µg·hr/mL to approximately 28 µg·hr/mL, from approximately 4 µg·hr/mL to approximately 24 µg·hr/mL, from approximately 4 µg·hr/mL to approximately 20 µg·hr/mL, from approximately 4 µg·hr/mL to approximately 16 µg·hr/mL, from approximately 4 µg·hr/mL to approximately 12 µg·hr/mL, from approximately 4 µg·hr/mL to approximately 8 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 8 µg·hr/mL to approximately 32 µg·hr/mL, from approximately 8 µg·hr/mL to approximately 28 µg·hr/mL, from approximately 8 µg·hr/mL to approximately 24 µg·hr/mL, from approximately 8 µg·hr/mL to approximately 20 µg·hr/mL, from approximately 8 µg·hr/mL to approximately 16 µg·hr/mL, from approximately 8 µg·hr/mL to approximately 12 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 12 µg·hr/mL to approximately 32 µg·hr/mL, from approximately 12 µg·hr/mL to approximately 28 µg·hr/mL, from approximately 12 µg·hr/mL to approximately 24 µg·hr/mL, from approximately 12 µg·hr/mL to approximately 20 µg·hr/mL, from approximately 12 µg·hr/mL to approximately 16 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 in a 24 hour period in a range of from approximately 4 µg·hr/mL to approximately 20 µg·hr/mL, and the like, or any range in between, in a subject with the hematologic cancer or an animal model (e.g., an animal model with a pre-established hematologic cancer).

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 4 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 6 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 8 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 10 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 12 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 14 µg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 16 μg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 18 μg·hr/mL in a 24 hour period.

In a specific aspect, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a mean plasma concentration of Cpd 1 of approximately 20 μg·hr/mL in a 24 hour period.

To achieve such plasma concentrations, an initial dose, then a loading dose followed by a maintenance dose of Cpd 1 or a pharmaceutical composition thereof may be administered. In certain aspects, subsequent doses of Cpd 1 or a pharmaceutical composition thereof may be adjusted accordingly based on the mean plasma concentrations of Cpd 1 achieved with initial doses of Cpd 1 or a pharmaceutical composition thereof administered to the subject.

In a specific aspect, a method for preventing, treating or ameliorating a hematologic cancer in a subject in need thereof comprises the administration of an effective amount of Cpd 1 or a pharmaceutical composition thereof to the subject, the effective amount may be adjusted based on the mean Area Under the Curve (AUC) in a 24 hour period ($AUC_{0-24}$), wherein a mean $AUC_{0-24<8}$ μg·hr/mL will allow a dose increase of up to about 100% of the initial dose administered; wherein a mean $AUC_{0-24}$ between and <14 μg·hr/mL will allow a dose increase of up to about 50% of the initial dose administered, wherein a mean $AUC_{0-24 \geq}14$ and <16 μg·hr/mL will allow a dose increase of up to about 33% of the initial dose administered, wherein a mean $AUC_{0-24 \geq}6$ and <18 μg·hr/mL will allow a dose increase of up to about 25% of the initial dose administered.

In specific aspects, a method for preventing, treating or ameliorating a hematologic cancer in a subject in need thereof comprises the administration of an effective amount of Cpd 1 or a pharmaceutical composition thereof to the subject, wherein the effective amount is a dosage that achieves a reduced target mean plasma concentration of one or more biomarkers in a subject with the hematologic cancer or an animal model (e.g., a hematologic cancer animal model).

In particular aspects, a method for preventing, treating or ameliorating a hematologic cancer in a subject in need thereof comprises the administration of an effective amount of Cpd 1 or a pharmaceutical composition thereof to the subject, wherein the effective amount is a dosage that achieves the desired tissue to mean plasma concentration ratios of Cpd 1 or a pharmaceutical composition thereof as determined, e.g., by any imaging techniques known in the art such as whole-body autoradiography, in a subject with the hematologic cancer or an animal model (such as an animal model with a pre-established hematologic cancer).

In some aspects, a method for preventing, treating or ameliorating a hematologic cancer in a subject in need thereof comprises the administration of an effective amount of Cpd 1 or a pharmaceutical composition thereof to the subject, wherein the effective amount may or may not be the same for each dose. In particular aspects, a first (i.e., initial) dose of Cpd 1 or a pharmaceutical composition thereof is administered to a subject in need thereof for a first period of time, followed by a second (i.e., loading) dose of Cpd 1 or a pharmaceutical composition thereof is administered to the subject for a second period of time and, subsequently, a third (i.e., maintenance) dose of Cpd 1 or a pharmaceutical composition thereof is administered to the subject for a second period of time. The first dose may be more than the second dose, or the first dose may be less than the second dose. In similar fashion, the third dose of Cpd 1 or a pharmaceutical composition thereof may be more or less than the second dose and more or less than the first dose.

In some aspects, the dosage amounts described herein refer to total amounts administered; that is, if more than one Compound is administered, then, in some aspects, the dosages correspond to the total amount administered. In a specific aspect, oral compositions contain about 5% to about 95% of Cpd 1 by weight.

The length of time that a subject in need thereof is administered Cpd 1 or a pharmaceutical composition thereof in accordance with a method for preventing, treating or ameliorating a hematologic cancer in a subject in need thereof will be the time period that is determined by cancer free survival or freedom from symptoms. In certain aspects, a method for treating a hematologic cancer presented herein comprises the administration of Cpd 1 or a pharmaceutical composition thereof for a period of time until the severity and/or number of one or more symptoms associated with the hematologic cancer decreases.

In some aspects, a method for preventing, treating or ameliorating a hematologic cancer in a subject in need thereof comprises the administration of Cpd 1 or a pharmaceutical composition thereof for up to 48 weeks. In other aspects, a method for preventing, treating or ameliorating a hematologic cancer in a subject in need thereof comprises the administration of Cpd 1 or a pharmaceutical composition thereof for up to 4 weeks, 8 weeks, 12 weeks, 16 weeks, 20 weeks, 24 weeks, 26 weeks (0.5 year), 52 weeks (1 year), 78 weeks (1.5 years), 104 weeks (2 years), or 130 weeks (2.5 years) or more.

In certain aspects, a method for preventing, treating or ameliorating a hematologic cancer in a subject in need thereof comprises the administration of Cpd 1 or a pharmaceutical composition thereof for an indefinite period of time. In some aspects, a method for treating a hematologic cancer presented herein comprises the administration of Cpd 1 or a pharmaceutical composition thereof for a period of time followed by a period of rest (i.e., a period wherein Cpd 1 or a pharmaceutical composition thereof is not administered) before the administration of Cpd 1 or a pharmaceutical composition thereof is resumed.

In specific aspects, a method for preventing, treating or ameliorating a hematologic cancer in a subject in need thereof comprises the administration of Cpd 1 or a pharmaceutical composition thereof in cycles, e.g., 1 week cycles, 2 week cycles, 3 week cycles, 4 week cycles, 5 week cycles, 6 week cycles, 8 week cycles, 9 week cycles, 10 week cycles, 11 week cycles, or 12 week cycles. In such cycles, Cpd 1 or a pharmaceutical composition thereof may be administered once, twice, three times, or four times daily.

In specific aspects, the period of time of administration of Cpd 1 or a pharmaceutical composition thereof may be dictated by one or more monitoring parameters, e.g., concentration of certain biomarkers.

In particular aspects, the period of time of administration of Cpd 1 or a pharmaceutical composition thereof may be adjusted based on one or more monitoring parameters, e.g., concentration of biomarkers.

In certain aspects, in accordance with a method for preventing, treating or ameliorating a hematologic cancer in a subject in need thereof, Cpd 1 or a pharmaceutical composition thereof is administered to a subject in need thereof prior to, concurrently with, or after a meal (e.g., breakfast, lunch, or dinner). In specific aspects, in accordance with the methods for treating a hematologic cancer presented herein, Cpd 1 or a pharmaceutical composition thereof is administered to a subject in need thereof in the morning (e.g., between 5 am and 12 pm).

In certain aspects, in accordance with a method for preventing, treating or ameliorating a hematologic cancer in a subject in need thereof, Cpd 1 or a pharmaceutical composition thereof is administered to a subject in need thereof at noon (i.e., 12 pm). In particular aspects, in accordance with the methods for treating a hematologic cancer presented herein, Cpd 1 or a pharmaceutical composition thereof is administered to a subject in need thereof in the afternoon (e.g., between 12 pm and 5 pm), evening (e.g., between 5 μm and bedtime), and/or before bedtime.

In specific aspects, a dose of Cpd 1 or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly.

In certain aspects, a dose of Cpd 1 or a pharmaceutical composition thereof is administered to a subject once or twice per day.

In certain aspects, a dose of Cpd 1 or a pharmaceutical composition thereof is administered to a subject once per day.

Combination Therapies

Presented herein are combination therapies for the treatment of a hematologic cancer which involve the administration of Cpd 1 or a pharmaceutical composition thereof in combination with one or more additional therapies to a subject in need thereof. In a specific aspect, presented herein are combination therapies for the treatment of a hematologic cancer which involve the administration of an effective amount of Cpd 1 or a pharmaceutical composition thereof in combination with an effective amount of another therapy to a subject in need thereof.

As used herein, the term "in combination," refers, in the context of the administration of Cpd 1 or a pharmaceutical composition thereof, to the administration of Cpd 1 or a pharmaceutical composition thereof prior to, concurrently with, or subsequent to the administration of one or more additional therapies (e.g., agents, surgery, or radiation) for use in treating a hematologic cancer. The use of the term "in combination" does not restrict the order in which one or more therapeutic agents and one or more additional therapies are administered to a subject. In specific aspects, the interval of time between the administration of Cpd 1 or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain aspects, Cpd 1 or a pharmaceutical composition thereof and one or more additional therapies are administered less than 1 day, 1 week, 2 weeks, 3 weeks, 4 weeks, one month, 2 months, 3 months, 6 months, 1 year, 2 years, or 5 years apart.

In some aspects, the combination therapies provided herein involve administering Cpd 1 or a pharmaceutical composition thereof daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain aspects, Cpd 1 or a pharmaceutical composition thereof and one or more additional therapies are cyclically administered to a subject. Cycling therapy comprises the administration of Cpd 1 or a pharmaceutical composition thereof for a period of time, followed by the administration of one or more additional therapies for a period of time, and repeating this sequential administration. In certain aspects, cycling therapy may also include a period of rest where Cpd 1 or a pharmaceutical composition thereof or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an aspect, the number of cycles administered is from 1 to 12 cycles, from 2 to 10 cycles, or from 2 to 8 cycles.

In some aspects, a method for preventing, treating or ameliorating a hematologic cancer in a subject in need thereof comprises administering Cpd 1 or a pharmaceutical composition thereof as a single agent for a period of time prior to administering Cpd 1 or a pharmaceutical composition thereof in combination with an additional therapy. In certain aspects, the methods for treating a hematologic cancer provided herein comprise administering an additional therapy alone for a period of time prior to administering Cpd 1 or a pharmaceutical composition thereof in combination with the additional therapy.

In some aspects, the administration of Cpd 1 or a pharmaceutical composition thereof and one or more additional therapies in accordance with the methods presented herein have an additive effect relative the administration of Cpd 1 or a pharmaceutical composition thereof or said one or more additional therapies alone. In some aspects, the administration of Cpd 1 or a pharmaceutical composition thereof and one or more additional therapies in accordance with the methods presented herein have a synergistic effect relative to the administration of Cpd 1 or a pharmaceutical composition thereof or said one or more additional therapies alone.

As used herein, the term "synergistic," refers to the effect of the administration of Cpd 1 or a pharmaceutical composition thereof in combination with one or more additional therapies (e.g., agents), which combination is more effective than the additive effects of any two or more single therapies (e.g., agents).

In a specific aspect, a synergistic effect of a combination therapy permits the use of lower dosages (i.e., sub-optimal doses) of Cpd 1 or a pharmaceutical composition thereof or an additional therapy and/or less frequent administration of Cpd 1 or a pharmaceutical composition thereof or an additional therapy to a subject.

In certain aspects, the ability to utilize lower dosages of Cpd 1 or a pharmaceutical composition thereof or of an additional therapy and/or to administer Cpd 1 or a pharmaceutical composition thereof or said additional therapy less frequently reduces the toxicity associated with the administration of Cpd 1 or a pharmaceutical composition thereof or of said additional therapy, respectively, to a subject without reducing the efficacy of Cpd 1 or a pharmaceutical composition thereof or of said additional therapy, respectively, in the treatment of a hematologic cancer.

In some aspects, a synergistic effect results in improved efficacy of Cpd 1 or a pharmaceutical composition thereof and each of said additional therapies in treating a hematologic cancer. In some aspects, a synergistic effect of a combination of Cpd 1 or a pharmaceutical composition thereof and one or more additional therapies avoids or reduces adverse or unwanted side effects associated with the use of any single therapy.

The combination of Cpd 1 or a pharmaceutical composition thereof and one or more additional therapies can be administered to a subject in the same pharmaceutical composition. Alternatively, Cpd 1 or a pharmaceutical composition thereof and one or more additional therapies can be administered concurrently to a subject in separate pharmaceutical compositions. Cpd 1 or a pharmaceutical composition thereof and one or more additional therapies can be administered sequentially to a subject in separate pharmaceutical compositions. Cpd 1 or a pharmaceutical composition thereof and one or more additional therapies may also be administered to a subject by the same or different routes of administration.

The combination therapies provided herein involve administering to a subject to in need thereof Cpd 1 or a pharmaceutical composition thereof in combination with conventional, or known, therapies for treating a hematologic cancer. Other therapies for a hematologic cancer or a condition associated therewith are aimed at controlling or relieving one or more symptoms. Accordingly, in some aspects, the combination therapies provided herein involve administering to a subject to in need thereof a pain reliever, or other therapies aimed at alleviating or controlling one or more symptoms associated with a hematologic cancer or a condition associated therewith.

Specific examples of anti-cancer agents that may be used in combination with Cpd 1 or a pharmaceutical composition thereof for treating a hematologic cancer include: a hormonal agent (e.g., aromatase inhibitor, selective estrogen receptor modulator (SERM), and estrogen receptor antagonist), chemotherapeutic agent (e.g., microtubule dissemby blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with Cpd 1 or a pharmaceutical composition thereof for treating a hematologic cancer include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with Cpd 1 or a pharmaceutical composition thereof for treating cancer include microtubule disasssembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and *vinca* alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of anti-angiogenic agents that may be used in combination with Cpd 1 or a pharmaceutical composition thereof for treating a hematologic cancer include VEGF antagonists, receptor antagonists, integrin antagonists (e.g., vitaxin, cilengitide, and S247), and VTAs/VDAs (e.g., fosbretabulin). VEGF antagonists include, but are not to, anti-VEGF antibodies (e.g., bevacizumab (branded/marketed as AVASTIN®) and ranibizumab (branded/marketed as LUCENTIS®)), VEGF traps (e.g., aflibercept), VEGF antisense or siRNA or miRNA, and aptamers (e.g., pegaptanib (branded/marketed as MACUGEN®)). Anti-angiogenic agents that are receptor antagonists include, but are not limited to, antibodies (e.g., ramucirumab) and kinase inhibitors (e.g., sunitinib, sorafenib, cediranib, panzopanib, vandetanib, axitinib, and AG-013958) such as tyrosine kinase inhibitors. Other non-limiting examples of anti-angiogenic agents include ATN-224, anecortave acetate (branded/marketed as RETAANE®), microtubule depolymerization inhibitor such as combretastatin A4 prodrug, and protein or protein fragment such as collagen 18 (endostatin).

Non-limiting examples of other therapies that may be administered to a subject in combination with Cpd 1 or a pharmaceutical composition thereof for treating a hematologic cancer include:

(1) a statin such as lovostatin (e.g., branded/marketed as MEVACOR®);
(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;
(3) a farnesyltransferase inhibitor agent such as tipifarnib (e.g., branded/marketed as ZARNESTRA®);
(4) an antifibrotic agent such as pirfenidone;
(5) a pegylated interferon such as PEG-interferon alfa-2b;
(6) a CNS stimulant such as methylphenidate (branded/marketed as RITALIN®);
(7) a HER-2 antagonist such as anti-HER-2 antibody (e.g., trastuzumab) and kinase inhibitor (e.g., lapatinib);
(8) an IGF-1 antagonist such as an anti-IGF-1 antibody (e.g., AVE1642 and IMC-A11) or an IGF-1 kinase inhibitor;
(9) EGFR/HER-1 antagonist such as an anti-EGFR antibody (e.g., cetuximab, panitumamab) or EGFR kinase inhibitor (e.g., erlotinib (e.g., branded/marketed as TARCEVA®), gefitinib);
(10) SRC antagonist such as bosutinib;
(11) cyclin dependent kinase (CDK) inhibitor such as seliciclib;
(12) Janus kinase 2 inhibitor such as lestaurtinib;
(13) proteasome inhibitor such as bortezomib;
(14) phosphodiesterase inhibitor such as anagrelide;
(15) inosine monophosphate dehydrogenase inhibitor such as tiazofurine;
(16) lipoxygenase inhibitor such as masoprocol;
(17) endothelin antagonist;
(18) retinoid receptor antagonist such as tretinoin or alitretinoin;
(19) immune modulator such as lenalidomide, pomalidomide, or thalidomide (e.g., branded/marketed as THALIDOMID®);
(20) kinase (eg, tyrosine kinase) inhibitor such as imatinib (e.g., branded/marketed as GLEEVEC®), dasatinib, erlotinib, nilotinib, gefitinib, sorafenib, sunitinib (e.g., branded/marketed as SUTENT®), lapatinib, AEE788, or TG100801;
(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NF-κβ) antagonist such as OT-551, which is also an anti-oxidant;
(26) hedgehog inhibitor such as CUR61414, cyclopamine, GDC-0449, or anti-hedgehog antibody;
(27) histone deacetylase (HDAC) inhibitor such as SAHA (also known as vorinostat (branded/marketed as ZOLINZA®)), PCI-24781, SB939, CHR-3996, CRA-024781, ITF2357, JNJ-26481585, or PCI-24781;
(28) retinoid such as isotretinoin (e.g., branded/marketed as ACCUTANE®);
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic such as rosiglitazone maleate (e.g., branded/marketed as AVANDIA®);
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;
(35) receptor tyrosine kinase inhibitors of Flk-1/KDR/VEGFR2, FGFR1 and PDGFR beta such as SU5416 and SU6668;
(36) anti-inflammatory agent such as sulfasalazine (e.g., branded/marketed as AZULFIDINE®); and
(37) TGF-beta antisense therapy.

Non-limiting examples of other therapies that may be administered to a subject in combination with Cpd 1 or a pharmaceutical composition thereof for treating a hematologic cancer include: a synthetic nonapeptide analog of naturally occurring gonadotropin releasing hormone such as leuprolide acetate (branded/marketed as LUPRON®); a nonsteroidal, anti-androgen such as flutamide (branded/marketed as EULEXIN®) or nilutamide (branded/marketed as NILANDRON®); a non-steroidal androgen receptor inhibitor such as bicalutamide (branded/marketed as CASODEX®); steroid hormone such as progesterone; anti-fungal agent such as Ketoconazole (branded/marketed as NIZORAL®); glucocorticoid such as prednisone; estramustine phosphate sodium (branded/marketed as EMCYT®); and bisphosphonate such as pamidronate, alendronate, and risedronate.

Additional specific examples of therapies that may be used in combination with Cpd 1 or a pharmaceutical composition thereof for treating a hematologic cancer include, but are not limited to, agents associated with cancer immunotherapy (e.g., cytokines, interleukins, and cancer vaccines).

Specific examples of agents alleviating side-effects associated with a hematologic cancer that can be used as therapies in combination with Cpd 1 or a pharmaceutical composition thereof, include, but are not limited to: anti-emetics, e.g., Ondansetron hydrochloride (branded/marketed as Zofran®), Granisetron hydrochloride (branded/marketed as Kytril®), Lorazepam (branded/marketed as Ativan®) and Dexamethasone (branded/marketed as Decadron®).

In certain aspects, combination therapies provided herein for treating a hematologic cancer comprise administering Cpd 1 or a pharmaceutical composition thereof in combination with one or more agents used to treat and/or manage a side effect, such as, bleeding (usually transient, low-grade epistaxis), arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelodysplastic syndromes, myelosuppression, fatigue, hypothyroidism, QT interval prolongation, or heart failure.

In certain aspects, Cpd 1 or a pharmaceutical composition thereof is not used in combination with a drug that is primarily metabolized by CYP2D6 (such as an antidepressant (e.g, a atricyclic antidepressant, a selective serotonin reuptake inhibitor, and the like), an antipsychotic, a beta-adrenergic receptor blocker, or certain types of anti-arrhythmics) to treat a hematologic cancer.

Kits

Provided herein is a pharmaceutical pack or kit comprising one or more containers filled with Cpd 1 or a pharmaceutical composition thereof. Additionally, one or more other therapies useful for the treatment of a hematologic cancer, or other relevant agents can also be included in the pharmaceutical pack or kit. Also provided herein is a pharmaceutical pack or kit comprising one or more containers filled with one or more of the ingredients of the pharmaceutical compositions described herein. Optionally associated with such kits can be a notice in the form prescribed by a governmental agency regulating the manufacture, use or sale of pharmaceuticals or biological products, which notice reflects approval by the agency of manufacture, use or sale for human administration.

EXAMPLES

General Methods. All culture media and supplement agents were purchased from (Gibco BRL, Invitrogen). Tumor cell lines purchased from ATCC were maintained in DMEM (adherent cells) or RPMI-1640 (suspension cells) containing 1 g/L glucose, supplemented with 10% fetal bovine serum (FBS), penicillin (50 IU/mL), and streptomycin (50 μg/mL). Cells were cultured at 37° C. in a humidified atmosphere containing 5% $CO_2$ and 21% $O_2$ in air (normoxia). For hypoxic exposure, cells were placed in a hypoxia incubator (NAPCO 8000 WJ) with a mixture of gas consisting of 1% $O_2$, 5% $CO_2$, and 94% $N_2$. All primary cells were purchased from AllCells, Inc and cultured in RPMI-1640 (for peripheral blood mononuclear cells, PBMC) or DMEM (for adherent cells) supplemented with 10% FBS, penicillin (50 IU/mL), and streptomycin (50 μg/mL).

Western Blot Analysis. Cells were treated with test compounds for 24 to 48 hours as indicated in the Results section. Subsequently, the conditioned medium was harvested by mixing with equal volume of 2×SDS-PAGE sample buffer (Bio-Rad). Whole-cell extracts were obtained by lysing cells either directly in 1×SDS-PAGE sample buffer (Bio-Rad) or in M-PER lysis buffer containing 150 mmol/L NaCl, 2 mmol/L EDTA and 1× Halt protease inhibitors (Pierce, Rockford, Ill.). Proteins in the samples were resolved on a Tris-glycine Criterion gel (Bio-Rad) and transferred onto a 0.45 μm nitrocellulose membrane. The membranes were then immunoblotted with specific antibodies indicated in the Results section. Antibody (C1) specific for VEGFA was purchased from Santa Cruz Biotechnologies, CA (1:200 dilution); Antibody specific for human β-actin was purchased from Abcam (1:10000 dilution); Antibody specific for V5-tag was purchased from Invitrogen (1:5000 dilution). Antibody specific for DHODH was purchased from Proteintech (Cat #: 14877-1-AP, 1:500 dilution); and antibody specific for human prohibitin was purchased from Thermo Scientific (Cat #: PA5-12274 and PA5-14133, 1:1000 dilution). Immunodetection was done using the corresponding secondary antibodies conjugated with infrared dyes or horseradish peroxide. The expression levels of proteins were detected with Odyssey (LI-COR) or using enhanced chemiluminescence (Pierce, Rockford, Ill.).

Determination of ELISA $EC_{50}$ and Cytotoxicity $CC_{50}$: All ELISAs were performed using commercially available ELISA kits (R&D Systems) according to the manufacturer's instructions. The screen of 240 cell lines were performed in Crown Bioscience (Shanghai, China). Cells were treated with Cpd 1 in a serial of doses for 72 hours and the inhibition of cell proliferation was determined using a standard assay, CellTiter-Glo® Luminescent Cell Viability Assay (Promega, Madison, Wis.) that measures total cellular adenosine triphosphate (ATP) concentrations as an indicator of cell viability. Data generated from ELISA or cytotoxicity studies were plotted with Prism software, with the Y-axis typically representing the % inhibition and the X-axis representing log compound concentration. A sigmoid dose response with a variable slope regression curve was generated for each compound. Maximal inhibition was set at 100% and minimal at 0%. $EC_{50}$ and $CC_{50}$ values were automatically calculated after curve fitting using the Prism software.

Human Tumor Xenograft Studies. All studies involving animals were performed in strict accordance with guidelines promulgated by the American Association for Accreditation of Laboratory Animal Care with the oversight of animal use and care committees.

Human Xenograft Model: HT1080 or MOLM-13 tumor cells in log phase growth ($5-10\times10^6$ cells/mouse, depending on cell lines) were implanted subcutaneously in male athymic nude mice. When the average tumor size reached the indicated size, mice were randomly divided into groups (10-15 mice/group) and administered vehicle or test compounds orally, once a day or twice per day as indicated. Tumor size was measured using calipers at periodic intervals during the study and tumor volume was calculated as $L\times W^2/2$, in which L represents the longest and W is the shortest diameter of the tumors. At the end of the experiments, tumors were excised and homogenized on ice in Tris-HCl buffer containing a cocktail of proteinase inhibitors using a Powergen homogenizer fitted with Omni-Tip disposable/reusable probes (both from Fisher Scientific). Intratumoral levels of growth factors and proteins were measured using commercially available ELISA kits (R&D Systems). Protein concentrations of the homogenates were measured (Bio-Rad protein assay kit) and intratumoral growth factor levels normalized to the total protein concentration.

Systemic Leukemia Lethality Model: Male NOD-SCID mice were inoculated with MOLT-4 human ALL tumor cells ($1\times10^7$ cells in 200 μL PBS) by intravenous (IV) injection. Eight days after tumor inoculation, mice were randomized into two groups (10 mice per groups) and treated with either vehicle or Cpd 1 (10 mg/kg qd). The mice were dosed and observed until moribund, at which time they were euthanized. At 2- and 4-weeks post-inoculation, whole blood was obtained from 5 mice per group by retro-orbital bleeding, stained with an antibody against human CD45, and the number of CD45-positive cells was determined by FACs. Data in FIG. 5b represents % of human CD45+ from blood of each mouse; where * indicates p<0.05, one way ANOVA, with multiple comparisons vs vehicle.

Quantification of Pyrimidine Nucleotide Synthesis Metabolites in Cpd 1 Treated Cells. HT1080 cells in log phase growth were seeded in 10 cm dishes ($4\times10^6$ cells/dish) and cultured in regular DMEM supplemented with 10% fetal bovine serum (FBS), penicillin (50 IU/mL), and streptomycin (50 μg/mL). After overnight incubation, the culture medium was replenished with glutamine free DMEM containing 1 g/L glucose, 10% fetal bovine serum (FBS), penicillin (50 IU/mL), streptomycin (50 μg/mL) and 1 mM $^{15}$N-glutamine (Sigma, Cat #: 490024). After culturing for the indicated time in the presence of compounds or vehicle control (0.5% DMSO), the cells were washed once with cold PBS (5 mL) and harvested and lysed in cold distilled H₂O (0.5 mL) with −80° C. methanol (1 mL) using a plastic cell scraper. The cell lysates were then centrifuged at 10,000×g for 15 minutes at 4° C., and supernatant collected for LC-MS/MS analysis of the $^{15}$N-labelled de novo pyrimidine synthesis metabolites.

LC-MS/MS Detection of Metabolites. Quantification of $^{15}$N-labelled de novo pyrimidine synthesis metabolites was carried out on an Accela pump and a PAL auto-sampler coupled to a TSQ Quantum Ultra mass spectrometer. The mass spectrometer was equipped with a heated electrospray ionization source operated in negative-ion mode (Thermo Fisher Scientific, Waltham, Mass.). The ion spray voltage was set at 2500 V, capillary temperature at 350° C., vaporizer temperature at 300° C.; sheath gas pressure at 50 units and auxiliary gas pressure at 5 units. A Thermo Fisher Scientific Hypercab column (3μ, 50×2.1 mm) was used and maintained at 50° C. for metabolite separation. Mobile phase A was 10 mM $NH_4HCO_3$ in water, pH 9.4, and mobile phase B was 10 mM $NH_4HCO_3$ in ACN-water (9:1). The flow rate was set at 0.50 mL/min. Ion transitions monitored were at m/z 156.0→m/z 112.0 for $^{15}$N-orotic acid, m/z 158.0→m/z 114.0 for 15N-dihydrorotic acid, m/z 324.0→m/z 79.0 for $^{15}$N-ump.

Conjugation of Cpd 1 S- and R-Enantiomer to Sephorose-6B beads. Sepharose 6B-Cpd 1: Epoxy-activated Sepharose 6B (GE healthcare cat. #17-0480-01, 1 g) was stirred in water (20 mL) for 2 h at RT, then filtered. The wet Sepharose 6B was diluted with pH 11 phosphate/NaOH buffer (5 mL). To a solution of 4-chlorophenyl (S)-6-chloro-1-(4-methoxyphenyl)-1,3,4,9-tetrahydro-2H-pyrido[3,4-b]indole-2-carboxylate (1 mmole) in DMF (12 mL) at 40° C. was added Sepharose-6B in phosphate/NaOH buffer. The reaction mixture was stirred further 24 hours at 40° C. The Sepharose 6B-Cpd 1 product was filtered and washed with DMF (100 mL), water (100 mL), pH 4 buffer (100 mL), pH 11 buffer (100 mL), water (100 mL), and 0.5M NaCl/water. The Sepharose-6B-Cpd 1 R-enantiomer was prepared using 4-chlorophenyl (R)-6-chloro-1-(4-methoxyphenyl)-1,3,4,9-tetrahydro-2H-pyrido[3,4-b]indole-2-carboxylate and the preceding reaction procedures.

Pull-down of Proteins Bound to Cpd 1-beads. Cells in log phase growth were washed with cold PBS once and then collected by trypsin digestion. After centrifugation at 1200 rpm for 5 minutes, the cells were re-suspended in lysis buffer (PBS+0.5% Triton X100+1× proteinase inhibitors (Halt, Roche, Cat #: 78440) and incubated on ice for 10 minutes; supernatants were collected after passing cells through a 22-gauge needle 10 times and centrifuging at 13,000 rpm for 15 min to remove cell debris. Subsequently, 1 mL of cell lysate solution (2 mg/mL protein) was added to each reaction tube containing 25 μL (packed volume) Cpd 1 S-enantiomer or control R-enantiomer beads and incubated for 2 hours at 4° C. with gentle agitation on a rotator; after three times wash with washing Buffer (1 mL) for 5 minutes each, the protein bound with beads were eluted with indicated buffer as shown in the result section. Proteins in the eluted samples were identified via LC-MS/MS or western blot analysis.

Mitochondria Isolated from Cultured K562 Cells as Source of DHODH for In Vitro Enzyme Inhibition Study. Mitochondria were isolated from K562 cells in log phase growth with a Dounce homogenizer as reported [27]. Briefly, about 2×10⁹ K562 cells were collected by centrifugation, re-suspended in 11 mL of ice-cold RSB hypo buffer (10 mM NaCl, 1.5 mM $MgCl_2$, 10 mM Tris-HCl, pH 7.5) in a 15-mL Dounce homogenizer. After swelling for 5-10 min on ice, the swollen cells were lysed with 10 strokes of the B pestle. A volume of 8 mL of 2.5×MS homogenization buffer (525 mM mannitol, 175 mM sucrose, 12.5 mM Tris-HCl, 2.5 mM EDTA, pH 7.5) was immediately added to the cell lysate and mixed to give a final concentration of 1×MS homogenization buffer. The homogenate was centrifuged at 1300 g for 5 min to remove nuclei, unlysed cells, and large membrane fragments. The mitochondria in the supernatant were pelleted at 12,000 g for 15 min and re-suspended in 1 mL 1×MS homogenization buffer for analysis of downstream DHODH activity as described below.

In Vitro DHODH Activity Assays. The chromogen reduction assay was carried out as previously reported [28]. DHODH activity was determined in the presence of compounds or vehicle control using the standard colorimetric DHODH continuous assay in which the oxidation of dihydroorotic acid (DHO) and subsequent reduction of ubiquinone is coupled with and measured by monitoring the reduction of 2,6-dichlorophenolindophenol (DCPIP). Briefly, full length purified recombinant human DHODH or mitochondria isolated from K562 cells were used as enzyme sources to test compound inhibition of DHODH activity. Enzymatic assays were conducted at 25° C. in a reaction buffer containing HEPES buffer (100 mM, pH 8.0), 150 mM NaCl, 5% glycerol and 0.05% Triton X-100, 200 μM L-dihydroorotate, 20 μM QD, 100 μM DCIP. The total volume of each reaction mixture was 100 μl containing 10 nM DHODH or an amount of isolated mitochondria yielding a similar level of DHODH activity. Compounds were prepared as 200× stock solutions in DMSO and the final concentration of DMSO was 0.5%. The DCIP reduction was monitored by measuring the absorbance at OD610 nm on a BioTek Power Wave XS2 and the enzyme reaction velocity was derived for each reaction using the GENS software.

Statistical Analysis. Data are given as the mean±SD or SEM as indicated for quantitative experiments. For statistical analysis, p-values were derived using unpaired Student's t-tests for any study with only two groups presented. Otherwise, comparisons of groups were performed on log-transformed data using a one way ANOVA test. All analyses were made using GraphPad Prism Software.

In vitro Combination Assay with HL-60 cells. HL-60 cells (human promyelocytic leukemia cells) were treated for 72 hours in the presence of Cpd 1 (DHODH inhibitor) and enasidenib (mutant IDH2 inhibitor IDHIFA®) alone and in combination. HL-60 cells are reported to express the wild-type IDH2 gene/protein. Concentrations of Cpd 1 tested included: 0, 1.4, 4.1, 12.3, 37, 111, 333 and 1000 nM. Concentrations of enasidenib were tested at: 0, 0.1, 0.3, 1.3, 6.4, 32, 160, 800, 4,000 and 20,000 nM. The combinations were evaluated in a full checkerboard titration. The extent of proliferation at 72 hours was determined by addition of Cell Titer Glo, and the percent inhibition calculated as referenced to vehicle/DMSO treated HL-60 cells.

Figure 9:
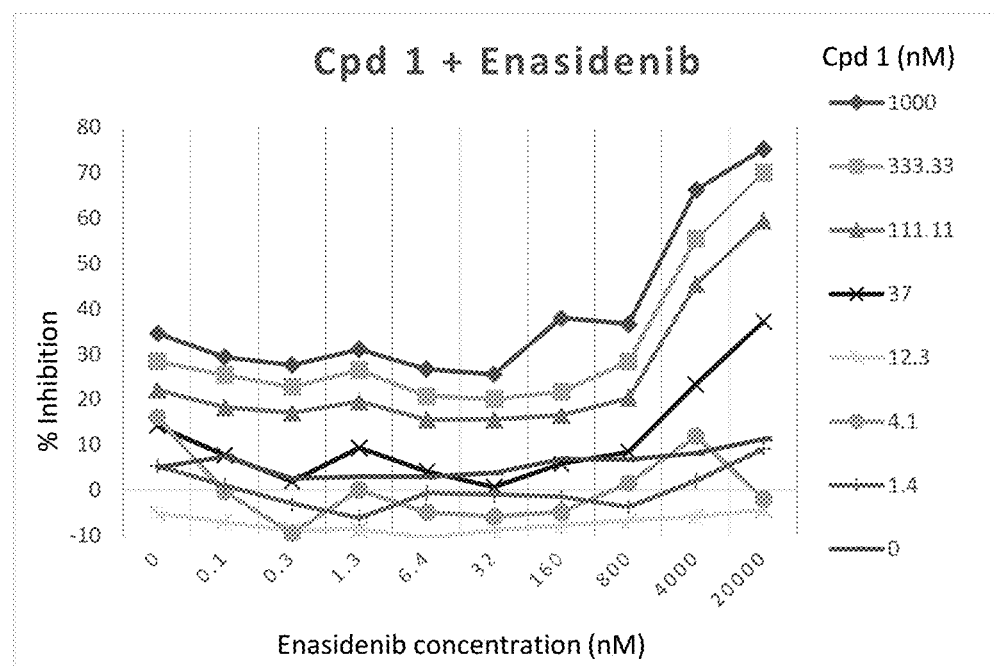
FIG. 9 compares the percent reduction in proliferation by treatment with the combination of Cpd 1 (inhibitor of DHODH function) and enasidenib (mutant IDH2 inhibitor) alone or in combination in HL-60 cells (human promyelocytic leukemia cells) treated for 72 hours.

Results. At all concentrations tested, enasidenib had no significant antiproliferative effect as single agent (see FIG. 9 with Cpd 1 nil concentration). Cpd 1 at a single agent test concentration of 111 nM had approximately 20% proliferative inhibition. However, the combination of enasidenib with Cpd 1, each at the two highest test concentrations of 4000:333 and 20000:1000 nM, respectively, demonstrated significant synergistic activity.

Conclusion. An inhibitor of DHODH function such as Cpd 1 in combination with an inhibitor of mutant IDH2 enzyme activity such as enasidenib may have utility in treating mutant and wild-type IDH2 leukemias.

In Vitro Combination Assays with Primary Leukemia Blood Samples. Blood samples from 11 leukemia subjects (10 AML and one ALL) were shipped overnight from clinical investigation sites. Upon arrival, red blood cells were lysed and the remaining cells counted and resuspended at the appropriate concentration in serum free media supplemented with cytokines. The samples were plated in 384-well microtiter plates and treated with the Cpd 1 S-enantiomer or R-enantiomer in triplicate. After incubation at 37° C. for 72 hours, the samples were stained with antibodies (antibody panel details below) and evaluated using an Intellicyt iQue Plus flow cytometer. A single concentration of Cpd 1 was tested (10 nM for cells from five AML subjects, or 20 nM for cells from the other five AML subjects and one ALL subject). A single concentration of enasidenib was tested (4000 nM) across cells from all 11 subjects.

Leukemia cells were quantified using the following FACS staining cell panel: DAPI, CD33, CD34, c-kit, CD3/CD19, CD66b, CD14, CD38. Live cells were gated using FSC/SSC and DAPI exclusion, and then further defined by cell surface marker expression.

Blood cells from subject 332AML harbored an oncogenic mutant IDH2 allele. Subjects 328AML, 333AML, 342AML, 347AML, and 351AML did not express an oncogenic mutant IDH2 allele. Genotype data was not available for the other 6 subjects.

For each subject an interaction score was calculated as: Measured minus Expected.
Measured=fraction of blasts after treatment with Cpd 1 and enasidenib.
Expected=fraction of blasts after treatment with Cpd 1 multiplied by the fraction of blasts after treatment with enasidenib as monotherapy.

Figure 10A:
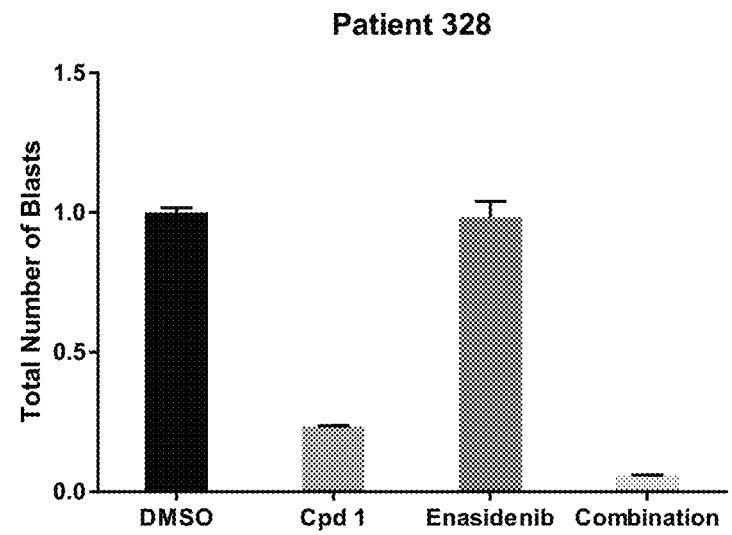
FIG. 10a compares the percent reduction in proliferation of total blasts and immature blasts with the combination of Cpd 1 (inhibitor of DHODH function) and enasidenib (mutant IDH2 inhibitor) alone or in combination in assays utilizing blood samples obtained from AML subjects and treated ex vivo for 72 hours. Enasidenib enhanced the activity of Cpd 1 in both mutant and wildtype IDH1 and IDH2 cells.
Figure 10B:
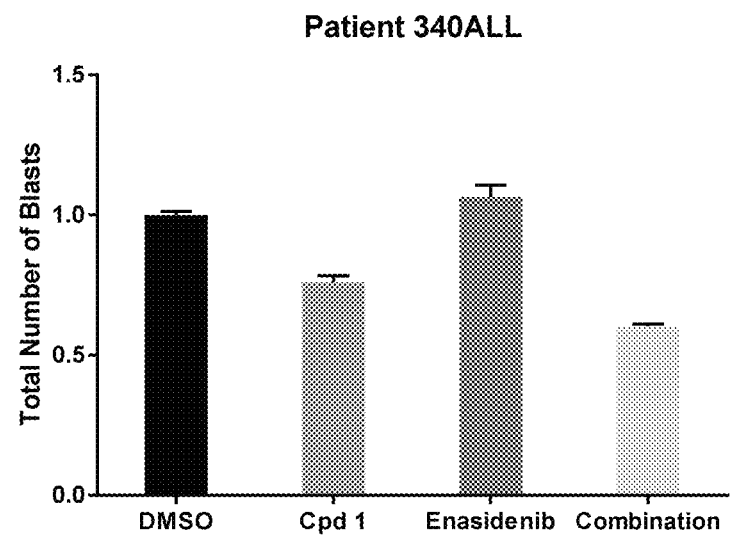
FIG. 10b compares the percent reduction in proliferation of total blasts and immature blasts with the combination of Cpd 1 (inhibitor of DHODH function) and enasidenib (mutant IDH2 inhibitor) alone or in combination in assays utilizing blood samples obtained from ALL subjects and treated ex vivo for 72 hours. Enasidenib enhanced the activity of Cpd 1 in both mutant and wildtype IDH1 and IDH2 cells.
Figure 11:
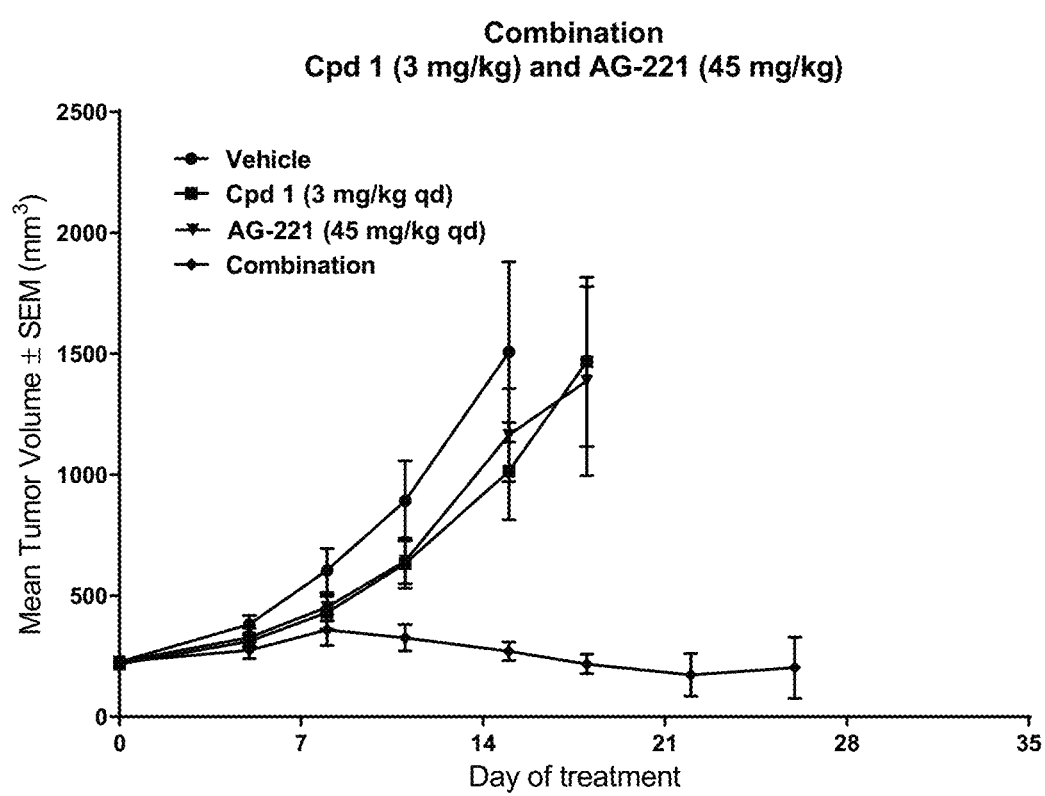
FIG. 11 compares the mean tumor volume in IDH2 wild-type cells after treatment with Cpd 1 alone, Agios Compound AG-221 alone and in combination. The use of the combination of a Cpd 1 DHODH functional inhibitor and a AG-221 IDH2 functional inhibitor demonstrates synergistic activity.

Results. Table 5 summarizes the effect of Cpd 1, enasidenib, and the combination against 11 leukemia subject samples. At 4000 nM, enasidenib did not have activity as a monotherapy against any of the subject samples. Cpd 1 significantly reduced proliferation in 10/11 samples (AML347 did not respond to Cpd 1). Further, the addition of enasidenib enhanced the activity of Cpd 1 in 10/11 samples (no further increase in inhibition was seen with the addition of enasidenib in sample 356). In some samples, the additional of enasidenib only marginally increased the anti-proliferative effect of Cpd 1 but in other samples a more pronounced effect was seen (for example, in subject sample 369). All samples were from AML subjects except sample 340 from an ALL subject. Abbreviations: ND=no data; mut=mutant; wt=wildtype FIG. 10 shows data from two representative samples, demonstrating that enasidenib enhanced the anti-proliferative effect of Cpd 1 in an AML subject (FIG. 10a) and an ALL subject (FIG. 10b).

Conclusion. An inhibitor of DHODH function such as Cpd 1 in combination with an inhibitor of mutant IDH2 function such as enasidenib has demonstrated synergistic activity which may have utility in treating mutant and wild-type IDH2 leukemia.

REFERENCE LIST

[1] Rawls J, Knecht W, Diekert K, Lill R, Loffler M. Requirements for the mitochondrial import and localization of dihydroorotate dehydrogenase. Eur J Biochem 2000 April; 267(7):2079-87.

[2] Zhang X, Yang J, Chen M, Li L, Huan F, Li A, et al. Metabolomics profiles delineate uridine deficiency contributes to mitochondria-mediated apoptosis induced by celastrol in human acute promyelocytic leukemia cells. Oncotarget 2016 Jul. 19; 7(29):46557-72.

[3] Baumann P, Mandl-Weber S, Volkl A, Adam C, Bumeder I, Oduncu F, et al. Dihydroorotate dehydrogenase inhibitor A771726 (leflunomide) induces apoptosis and diminishes proliferation of multiple myeloma cells. Mol Cancer Ther 2009 February; 8(2):366-75.

[4] Sykes D B, Kfoury Y S, Mercier F E, Wawer M J, Law J M, Haynes M K, et al. Inhibition of Dihydroorotate Dehydrogenase Overcomes Differentiation Blockade in Acute Myeloid Leukemia. Cell 2016 Sep. 22; 167(1):171-86.

[5] Cacciamani T, Vita A, Cristalli G, Vincenzetti S, Natalini P, Ruggieri S, et al. Purification of human cytidine deaminase: molecular and enzymatic characterization and inhibition by synthetic pyrimidine analogs. Arch Biochem Biophys 1991 Nov. 1; 290(2):285-92.

[6] Peters G J, Schwartsmann G, Nadal J C, Laurensse E J, van Groeningen C J, van der Vijgh W J, et al. In vivo inhibition of the pyrimidine de novo enzyme dihydroorotic acid dehydrogenase by brequinar sodium (DUP-785; NSC 368390) in mice and patients. Cancer Res 1990 Aug. 1; 50(15):4644-9.

[7] Ohnuma T, Roboz J, Shapiro M L, Holland J F. Pharmacological and biochemical effects of pyrazofurin in humans. Cancer Res 1977 July; 37(7 Pt 1):2043-9.

[8] McLean L R, Zhang Y, Degnen W, Peppard J, Cabel D, Zou C, et al. Discovery of novel inhibitors for DHODH via virtual screening and X-ray crystallographic structures. Bioorg Med Chem Lett 2010 Mar. 15; 20(6):1981-4.

[9] Jain A N. Effects of protein conformation in docking: improved pose prediction through protein pocket adaptation. J Comput Aided Mol Des 2009 June; 23(6):355-74.

TABLE 5

% Inhibition of Total Blasts; Effect of Cpd 1, enasidenib, or the Combination on Primary Leukemia Samples

| Sample ID | 328 | 332 | 333 | 340 | 342 | 347 | 351 | 356 | 359 | 369 | 371 |
|---|---|---|---|---|---|---|---|---|---|---|---|
| IDH2 mutational status | wt | mut | wt | ND | wt | wt | Wt | ND | ND | ND | ND |
| Cpd 1 | 76.6 | 41.5 | 70 | 24 | 91.9 | −11.6 | 28.9 | 47 | 75.7 | 49.7 | 52.9 |
| Enasidenib | 1.7 | −10.9 | −36.6 | −6.5 | 6.4 | −8.9 | 8.8 | 26.1 | −24.1 | −0.4 | −7.2 |
| Combination | 94.4 | 58 | 82.9 | 39.7 | 93.8 | 11.3 | 41.1 | 44.1 | 81.6 | 70.7 | 64.4 |
| Interaction Coefficient | −0.17 | −0.23 | −0.24 | −0.21 | −0.01 | −0.33 | −0.06 | 0.17 | −0.12 | −0.21 | −0.15 |

[10] Jain A N. Surflex: fully automatic flexible molecular docking using a molecular similarity-based search engine. J Med Chem 2003 Feb. 13; 46(4):499-511.
[11] Lane A N, Fan T W. Regulation of mammalian nucleotide metabolism and biosynthesis. Nucleic Acids Res 2015 Feb. 27; 43(4):2466-85.
[12] Barretina J, Caponigro G, Stransky N, Venkatesan K, Margolin A A, Kim S, et al. The Cancer Cell Line Encyclopedia enables predictive modelling of anticancer drug sensitivity. Nature 2012 Mar. 28; 483(7391):603-7.
[13] Baumann P, Mandl-Weber S, Volkl A, Adam C, Bumeder I, Oduncu F, et al. Dihydroorotate dehydrogenase inhibitor A771726 (leflunomide) induces apoptosis and diminishes proliferation of multiple myeloma cells. Mol Cancer Ther 2009 February; 8(2):366-75.
[14] Fitzpatrick L R, Small J S, Doblhofer R, Ammendola A. Vidofludimus inhibits colonic interleukin-17 and improves hapten-induced colitis in rats by a unique dual mode of action. J Pharmacol Exp Ther 2012 September; 342(3):850-60.
[15] Wang X, Harrison J S, Studzinski G P. Enhancement of arabinocytosine (AraC) toxicity to AML cells by a differentiation agent combination. J Steroid Biochem Mol Biol 2016 November; 164:72-8.
[16] Cunningham J T, Moreno M V, Lodi A, Ronen S M, Ruggero D. Protein and nucleotide biosynthesis are coupled by a single rate-limiting enzyme, PRPS2, to drive cancer. Cell 2014 May 22; 157(5):1088-103.
[17] Mohamad Fairus A K, Choudhary B, Hosahalli S, Kavitha N, Shatrah O. Dihydroorotate dehydrogenase (DHODH) inhibitors affect ATP depletion, endogenous ROS and mediate S-phase arrest in breast cancer cells. Biochimie 2017 April; 135:154-63.
[18] Saini A K, Nanda J S, Lorsch J R, Hinnebusch A G. Regulatory elements in eIF1A control the fidelity of start codon selection by modulating tRNA(i)(Met) binding to the ribosome. Genes Dev 2010 Jan. 1; 24(1):97-110.
[19] Carlile T M, Rojas-Duran M F, Zinshteyn B, Shin H, Bartoli K M, Gilbert W V. Pseudouridine profiling reveals regulated mRNA pseudouridylation in yeast and human cells. Nature 2014 Nov. 6; 515(7525):143-6.
[20] Cody R, Stewart D, DeForni M, Moore M, Dallaire B, Azarnia N, et al. Multicenter phase II study of brequinar sodium in patients with advanced breast cancer. Am J Clin Oncol 1993 December; 16(6):526-8.
[21] Xu X, Williams J W, Shen J, Gong H, Yin D P, Blinder L, et al. In vitro and in vivo mechanisms of action of the antiproliferative and immunosuppressive agent, brequinar sodium. J Immunol 1998 Jan. 15; 160(2):846-53.
[22] Xu X, Williams J W, Gong H, Finnegan A, Chong A S. Two activities of the immunosuppressive metabolite of leflunomide, A77 1726. Inhibition of pyrimidine nucleotide synthesis and protein tyrosine phosphorylation. Biochem Pharmacol 1996 Aug. 23; 52(4):527-34.
[23] Deans R M, Morgens D W, Okesli A, Pillay S, Horlbeck M A, Kampmann M, et al. Parallel shRNA and CRISPR-Cas9 screens enable antiviral drug target identification. Nat Chem Biol 2016 May; 12(5):361-6.
[24] Packer R J, Rood B R, Turner D C, Stewart C F, Fisher M, Smith C, et al. Phase I and pharmacokinetic trial of PTC299 in pediatric patients with refractory or recurrent central nervous system tumors: a PBTC study. J Neurooncol 2015 January; 121(1):217-24.
[25] Basso L G M, Mendes L F S, Costa-Filho A J. The two sides of a lipid-protein story. Biophys Rev 2016 June; 8(2):179-91.
[26] Lewis T A, Sykes D B, Law J M, Munoz B, Rustiguel J K, Nonato M C, et al. Development of ML390: A Human DHODH Inhibitor That Induces Differentiation in Acute Myeloid Leukemia. ACS Med Chem Lett 2016 Dec. 8; 7(12):1112-7.
[27] Clayton D A, Shadel G S. Isolation of mitochondria from cells and tissues. Cold Spring Harb Protoc 2014 Oct. 1; 2014(10):db.
[28] Chen S F, Perrella F W, Behrens D L, Papp L M. Inhibition of dihydroorotate dehydrogenase activity by brequinar sodium. Cancer Res 1992 Jul. 1; 52(13):3521-7.
[29] Yen K, Travins J, Wang F, David M D, Artin E, Straley K, Padyana A, Gross S, DeLaBarre B, Tobin E, Chen Y, Nagaraja R, Choe S, Jin L, Konteatis Z, Cianchetta G, Saunders J O, Salituro F G, Quivoron C, Opolon P, Bawa O, Saada V, Paci A, Broutin S, Bernard O A, de Botton S, Marteyn B S, Pilichowska M, Xu Y, Fang C, Jiang F, Wei W, Jin S, Silverman L, Liu W, Yang H, Dang L, Dorsch M, Penard-Lacronique V, Biller S A, Su S M. AG-221, a First-in-Class Therapy Targeting Acute Myeloid Leukemia Harboring Oncogenic IDH2 Mutations. Cancer Discov. 2017 May; 7(5):478-493.
[30] Nassereddine S, Lap C J, Haroun F, Tabbara I. The role of mutant IDH1 and IDH2 inhibitors in the treatment of acute myeloid leukemia. Ann Hematol. 2017 December; 96(12):1983-1991.
[31] Amatangelo M D, Quek L, Shih A, Stein E M, Roshal M, David M D, Marteyn B, Famoud N R, de Botton S, Bernard O A, Wu B, Yen K E, Tallman M S, Papaemmanuil E, Penard-Lacronique V, Thakurta A, Vyas P, Levine R L; Enasidenib induces acute myeloid leukemia cell differentiation to promote clinical response; Blood, 10 Aug. 2017, 130:732-741.

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or aspects described herein. It is intended that the appended claims be interpreted to include all such equivalents.

What is claimed is:

1. A method of treating a hematologic cancer in a subject comprising administering a combination of an effective amount of a compound and enasidenib to a subject in need thereof, wherein said effective amount of said compound is an amount sufficient to achieve a decrease in the concentration of plasma dihydroorotate dehydrogenase in said subject, and wherein the compound is 4-chlorophenyl (S)-6-chloro-1-(4-methoxyphenyl)-1,3,4,9-tetrahydro-2H-pyrido[3,4-b]indole-2-carboxylate having the structure:

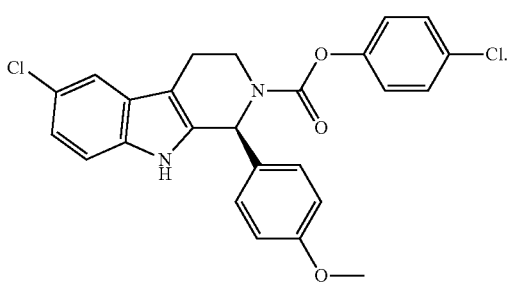 [SMILES: COc1ccc([C@H]2c3[nH]c4ccc(Cl)cc4c3CCN2C(=O)Oc2ccc(Cl)cc2)cc1]

2. The method of claim 1, wherein the hematologic cancer is a leukemia.

3. The method of claim 2, wherein the leukemia is selected from acute lymphoblastic leukemia, acute myeloid leukemia, acute nonlymphocytic leukemia, chronic lymphocytic leukemia or chronic myeloid leukemia.

4. The method of claim 1, wherein the amount of the compound and enasidenib administered inhibits or reduces the function of dihydroorotate dehydrogenase and isocitrate dehydrogenase in the subject.

5. A method of treating acute myeloid leukemia in a subject comprising administering a combination of an effective amount of a compound and cytarabine to a subject in need thereof, wherein said effective amount of said compound is an amount sufficient to achieve a decrease in the concentration of plasma dihydroorotate dehydrogenase in said subject, and wherein the compound is 4-chlorophenyl (S)-6-chloro-1-(4-methoxyphenyl)-1,3,4,9-tetrahydro-2H-pyrido[3,4-b]indole-2-carboxylate having the structure:

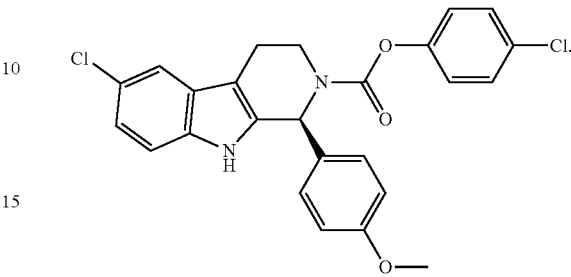

6. The method of claim 1, comprising administering a pharmaceutical composition comprising the compound to a subject.

7. The method of claim 5, comprising administering a pharmaceutical composition comprising the compound to a subject.

* * * * *